US012661503B2

(12) United States Patent
Kern et al.

(10) Patent No.: US 12,661,503 B2
(45) Date of Patent: Jun. 23, 2026

(54) MICROCURRENT-BASED SKIN TREATMENT AND PRETREATMENT TECHNIQUES

(71) Applicant: NSE Products, Inc., Provo, UT (US)

(72) Inventors: Dale G. Kern, Hyde Park, UT (US); Ganesh Diwakar, Draper, UT (US)

(73) Assignee: NSE Products, Inc., Provo, UT (US)

( * ) Notice: Subject to any disclaimer, the term of this patent is extended or adjusted under 35 U.S.C. 154(b) by 592 days.

(21) Appl. No.: 18/111,353

(22) Filed: Feb. 17, 2023

(65) Prior Publication Data

US 2023/0293886 A1     Sep. 21, 2023

Related U.S. Application Data

(60) Provisional application No. 63/336,573, filed on Apr. 29, 2022, provisional application No. 63/311,900, filed on Feb. 18, 2022.

(51) Int. Cl.
A61N 1/04          (2006.01)
A61N 1/32          (2006.01)

(52) U.S. Cl.
CPC ........... A61N 1/325 (2013.01); A61N 1/0428 (2013.01); A61N 1/0476 (2013.01)

(58) Field of Classification Search
CPC .. A61N 1/0412; A61N 1/0428; A61N 1/0476; A61N 1/325; A61N 1/327
See application file for complete search history.

(56) References Cited

U.S. PATENT DOCUMENTS

| | | | |
|---|---|---|---|
| RE42,835 E | 10/2011 | Chornenky et al. | |
| 9,968,773 B1 | 5/2018 | Hocking | |
| 2008/0275468 A1 | 11/2008 | Chuang et al. | |
| 2013/0345661 A1 | 12/2013 | Chang | |
| 2014/0330196 A1 | 11/2014 | Ingman et al. | |
| 2016/0089545 A1 | 3/2016 | Juluri et al. | |
| 2017/0239454 A1* | 8/2017 | Heath .................... A61N 1/327 |
| 2020/0197696 A1 | 6/2020 | Nagel et al. | |

(Continued)

FOREIGN PATENT DOCUMENTS

| | | |
|---|---|---|
| EP | 4166190 A1 | 4/2023 |
| WO | 2004107995 A2 | 12/2004 |
| WO | 2015044636 A1 | 4/2015 |

OTHER PUBLICATIONS

International Search Report and Written Opinion dated May 17, 2023 in connection with International Patent Application No. PCT/US2023/013338, 8 pages.

(Continued)

*Primary Examiner* — Deanna K Hall
(74) *Attorney, Agent, or Firm* — Dorsey & Whitney LLP

(57)          ABSTRACT
A method includes applying one or more electrodes to the skin or skin surface of a subject, applying a voltage or current signal to the skin surface via one or more of the electrodes, and modulating the signal to maintain treatment efficacy, or so that the power output can be charge balanced, or both. An agent can be applied to the skin surface during a treatment period defined after the voltage or current signal is applied. Permeability of the skin to one or more components of the agent is enhanced or increased during the treatment period, responsive to the modulated power output. A device for performing the method is also provided.

34 Claims, 36 Drawing Sheets

(56)                    References Cited

U.S. PATENT DOCUMENTS

| | | |
|---|---|---|
| 2020/0222687 A1 | 7/2020 | Skiba et al. |
| 2020/0323769 A1 | 10/2020 | Cazares Delgadillo et al. |
| 2021/0228863 A1 | 7/2021 | Del Rossi et al. |
| 2021/0308452 A1 | 10/2021 | Kern et al. |

OTHER PUBLICATIONS

Diwakar, Ganesh et al. "Clinical assessment of low level microcurrent of short duration treatment system in enhancing allantoin penetration and improving the appearance of skin cellulite, radiance, texture, and firmness," May 18, 2022.

Gupta, Rakesh , et al., Gupta, Rakesh, "Effect of Chemical Permeation Enhancers on Skin Permeability: In silico screening using Molecular Dynamics simulations," Scientific Reports, Feb. 6, 2019, 11 pages.

Ita, Kevin B., Ita, Kevin B. "Chemical Penetration Enhancers for Transdermal Drug Delivery—Success and Challenges," Current Drug Delivery, 12, 2015, pp. 645-651.

Lopes, Luciana B., et al., Lopes et al. "Chemical Penetration Enhancers," Therapeutic Delivery, 6(9), 2015, pp. 1053-1061.

Smith, Roger , Smith, Roger "Skin deep: overcoming barriers for effective transdermal drug delivery," Trainer Magazine, Jul. 13, 2019, 5 pages.

Turner, Norris G., et al., "The Effect of Current on Skin Barrier Function In Vivo: Recovery Kinetics Post-Iontophoresis".

Extended European Search Report dated Jan. 21, 2026 in connection with European patent application No. 23756923.1, 11 pages.

* cited by examiner

Galvanic Electrical Waveform
(GEWF)

Program Random Pulse Width Modulation Electrical Waveform
(PRPWMEWF)

Trinity NuFace Electrical Waveform
(TNFEW)

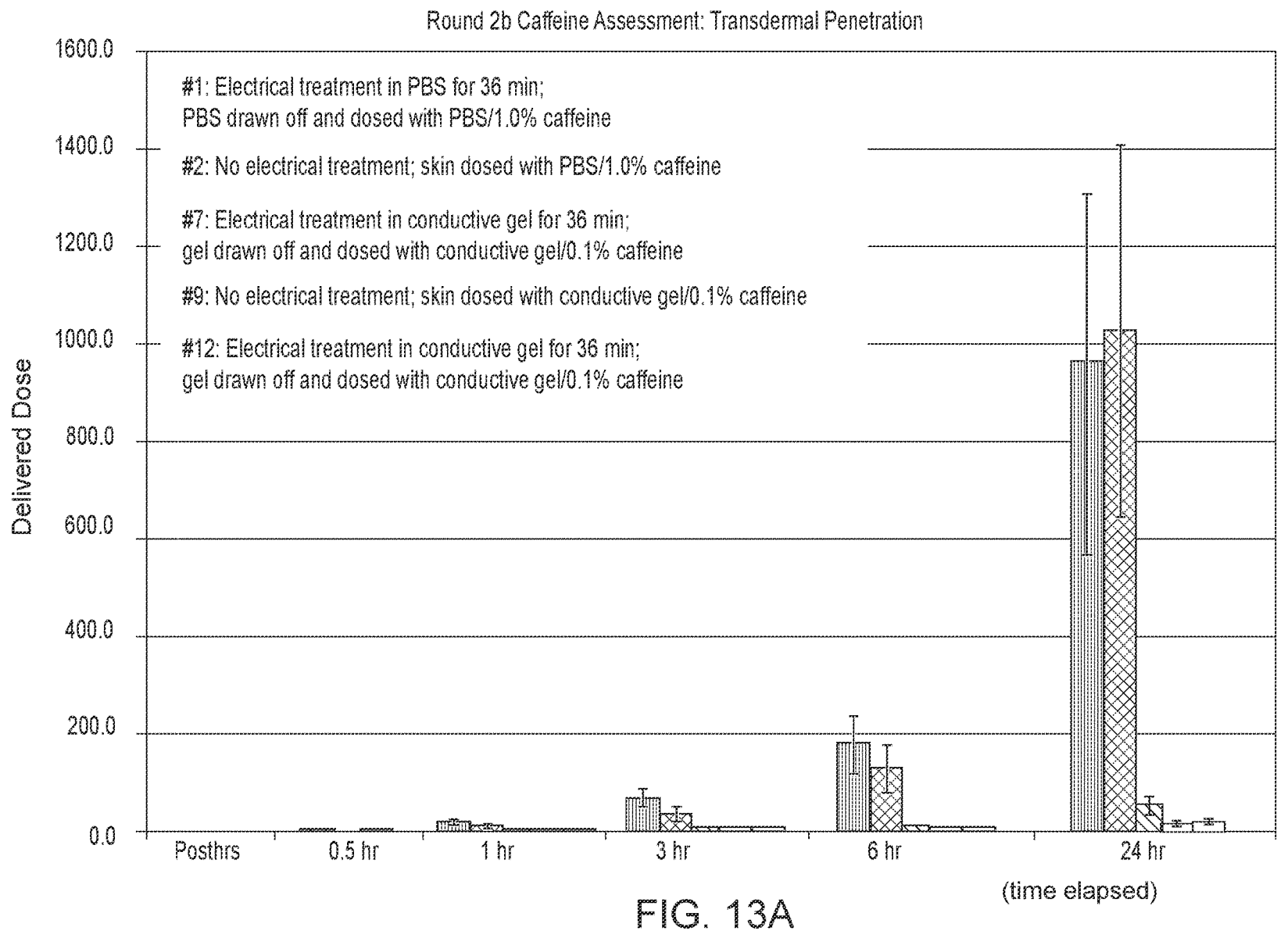

Round 2b Caffeine Assessment: Transdermal Penetration

1: Electrical treatment in PBS for 36 min;
PBS drawn off and dosed with PBS/1.0% caffeine

2: No electrical treatment; skin dosed with PBS/1.0% caffeine

7: Electrical treatment in conductive gel for 36 min;
gel drawn off and dosed with conductive gel/0.1% caffeine

9: No electrical treatment; skin dosed with conductive gel/0.1% caffeine

12: Electrical treatment in conductive gel for 36 min;
gel drawn off and dosed with conductive gel/0.1% caffeine

FIG. 13A

MICROCURRENT-BASED SKIN TREATMENT AND PRETREATMENT TECHNIQUES

CROSS-REFERENCE TO RELATED APPLICATIONS

This application claims priority to U.S. Provisional Application Ser. No. 63/311,900, "Microcurrent-Based Skin Treatment and Pretreatment Techniques," filed Feb. 18, 2022, and U.S. Provisional Application Ser. No. 63/336,573, "Microcurrent-Based Skin Treatment and Pretreatment Techniques," filed Apr. 29, 2022, each of which is incorporated by reference herein, in the entirety and for all purposes.

FIELD

This application relates to current-based skin treatment and pretreatment techniques. More generally, the application relates to microcurrent treatments adapted for enhanced transport to, from, and across selected layers of the skin tissue. Applications include, but are not limited to, delivery of topical agents, skin treatments, and other beneficial products.

BACKGROUND

Skin covers the body's surface, forming a physical, insulating barrier against the outside environment, and protecting the body from excess heat, cold, dryness, humidity, solar radiation, dirt and foreign objects, as well and insects and other invasive organisms. The skin also helps maintain body temperature and forms an important part of the immune system, while regulating the passage of water, electrolytes and other materials, and providing a network of nerves adapted for touch, heat sensitivity, and other forms of physical sensation.

Skin is the major component of the integumentary system, which also includes the hair, nails, and (in some animals) other features such as feathers, scales and hooves. The outermost layer of the skin is the epidermis, which includes cells called keratinocytes that form an environmental barrier and synthesize vitamin D. The epidermis also includes melanocytes, which produce melanin to protect against harmful UV radiation, Merkel cells, which provide sensitivity to touch, and Langerhans cells, a type of white blood cell or macrophage that protects the body against infection as part of the immune system.

The epidermis surrounds the dermis. The structure of the dermis is provided by fibroblasts, which synthesize collagen and elastin proteins to form the extracellular matrix, with collagen fibers to provide strength and toughness, and elastin threads or filaments to provide elasticity and flexibility. The fibroblasts also produce proteoglycans, viscous proteins that provide hydration and lubrication, and regulate ionic binding and molecular transport. The dermis also includes macrophages and mast cells, additional components of the immune system, as well as hair follicles, sweat and oil glands, nerve cells, and a network of blood vessels.

The epidermis and dermis make up the cutis. The subcutis underlies the cutis, including adipose (fat) cells, elastin and other subcutaneous tissues connecting the cutis to the underlying muscles, fascia and other connective tissue such as the periosteum (covering the bones).

In addition to its protective barrier functions, the skin also includes a system of pores to help regulate the passage of fluids across the different skin layers, and underlying tissues.

Little, however, is well understood about the effect of current on skin permeability, and there remains a significant need for improved techniques adapted to enhance delivery of topical agents, treatment products, and other beneficial substances across selected skin layers.

SUMMARY

A method for skin treatment includes applying one or more electrodes to a skin surface of a subject, applying a voltage or current signal to the skin surface via one or more of the electrodes, and modulating the power output to the skin surface, via the voltage or current signal. A latency period can be defined following modulating the power output; e.g., during which no further voltage or current signal is applied via the one or more electrodes. An agent can be applied to the skin surface after signal, or after the latency period, where permeability of the skin to one or more components of the agent is enhanced or increased, responsive to the modulated power output.

BRIEF DESCRIPTION OF THE DRAWINGS

FIGS. 13A, 13B and 13C are bar charts illustrating transdermal caffeine penetration, retention and flux, following selected current treatments.

Figure 1:
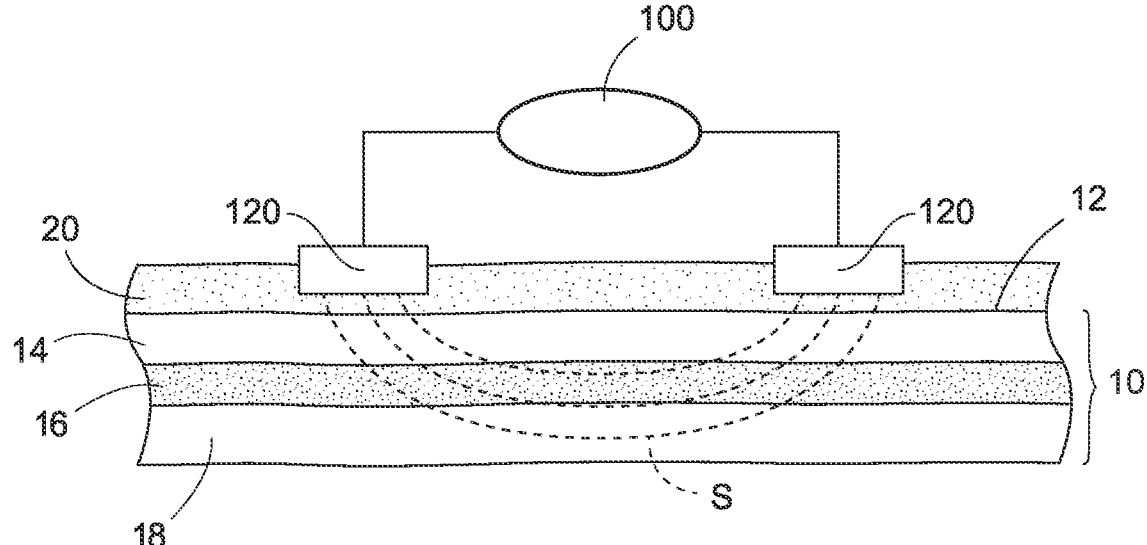
FIG. 1 is a sectional diagram illustrating application of a current treatment to a skin surface.

This application describes the disclosed technology with reference to the drawings and associated written description, in which like numerals may represent similar structural and functional components. These examples and embodiments are merely representative, and do not limit practice of the invention as claimed. Persons of skill in the art will recognize that equivalents can be substituted and changes may be made in form and detail while remaining within the scope of coverage, as defined by the language of the appended claims.

DETAILED DESCRIPTION

In addition to the barrier properties provided by the stratum corneum, epidermis, dermis, and other layers, the skin also includes sudoriferous (sweat) glands to help regulate temperature by secreting water, electrolytes, and (e.g., nitrogenous) waste products. Eccrine sweat glands open onto the skin surface via the pores, while apocrine sweat glands open into the hair follicles, in selected areas of the skin. Sebaceous glands also open into the follicles, secreting lipids and other natural oils (sebum) to lubricate the hair and adjacent skin surfaces.

The pores, follicles and associated glandular structures can also provide an avenue for transdermal absorption and delivery, as well as secretion. The skin is also permeable on a cellular level, with permeability depending on the structure of the respective layer. When keratinocytes are formed in the lower layers of the epidermis, for example, they have relatively permeable phospholipid cell membranes. As the keratinocytes migrate outward toward the stratum corneum, however, they transform into corneocytes, which are flattened, differentiated, anucleate (dead) cells with a durable, insoluble envelope made of cross-linked proteins, embedded in a lipid matrix and linked together by protein complexes called desmosomes. Fluid transport can also occur via the extracellular matrix and associated interstitial fluid, which surrounds the cells individual cells, and supports the transport of salts, sugars, lipids, fatty acids, amino acids, proteins, enzymes, hormones, neurotransmitters, and other cellular products including genetic materials.

This disclosure is directed to the effects of current-based (e.g., microcurrent) skin treatments on skin transport processes, including both cellular and intercellular transport, as well as the pores, follicles, and associated glandular structures. These techniques are not limited to the current treatment itself, but also encompass latent, enhanced permeability effects observed following a given treatment. Applications include, but are not limited to, enhanced delivery of topical agents, skin treatments, and other beneficial products to and across selected skin layers, in a treatment period extending for minutes, hours or up to days following the current treatment.

A range of suitable voltage and current signals can be generated to improve delivery of a topical agent, via enhanced transmission, adsorption or absorption of the agent by, to or through one or more layers of the skin surface. Suitable modulated waveforms are described, for example, in U.S. Publication No. 2021/0308452 A1, "Modulated Waveform Treatment Device and Method," and in U.S. Provisional Patent Application No. 63/256,106, "Current Control System for Skin Treatment Device," filed Oct. 15, 2021, each of which is incorporated by reference herein, in the entirety and for all purposes.

These techniques are distinguished from iontophoresis, electromigration, electroosmosis, electroporation and similar traditional approaches, where transport of an ionic or polar agent may be enhanced by application of a concurrent (e.g., DC) current signal. Instead, a carefully modulated microcurrent stimulus is applied during a pretreatment phase, with or without a conducting gel or similar topical. Permeability is improved or enhanced following the pretreatment phase, for selected, beneficial components of a treatment agent, which can be applied before, during or after the pretreatment phase. The improved permeability is responsive to the power applied by the current stimulus during the pretreatment phase, and is exhibited without further application of the stimulus, even when the pretreatment is performed before application of the agent, and the agent is applied after the pretreatment is completed.

These microcurrent pretreatment techniques also distinguish from laser, needle, and micro-mechanical methods, where small holes or apertures are physically formed in the skin surface, rather than applying a carefully modulated waveform to enhance the skin's natural permeability processes. In contrast to the use of chemical penetration enhancers (CPEs) and other chemical methods, moreover, no reactive chemicals, sorption promotors or accelerants are necessary to breach the skin's natural barrier properties. Rather, skin permeability is enhanced by the carefully modulated microcurrent pretreatment, increasing transdermal flux for selected components of a topical agent or skin treatment formula without applying reactive chemical agents to the skin.

FIG. 1 is a sectional diagram illustrating the application of a current treatment device 100 configured to deliver an electrical stimulus S to the skin 10 or skin surface 11 of a subject, for example by user of the device 100, or by a skin scare technician, treatment specialist, or other person by whom the device 100 is applied to the skin 10 or skin surface 11.

As shown in FIG. 1, the skin care device 100 includes one or more electrodes 120 adapted for applying the current treatment S to the surface 12 of the subject's skin 10, for example in combination with a topical agent 20 as shown, or applied directly onto the skin surface 12. The skin (or "cutis") 10 extends from the skin surface 12 through an epidermal layer (or epidermis) 14, to a lower dermal layer (dermis) 16. The subcutis (or hypodermis) 18 comprises the subcutaneous tissues, underlying the cutis 16.

The dermis 16 includes an upper papillary layer and a lower reticular layer, formed of more loosely arranged and denser collagen fibers, respectively. The collagen fibers extend from the dermis 16 through the subcutis 18, forming connective tissues (fascia) that attach the skin (cutis) 10 to the underlying muscle, and other connective tissue. The subcutis 18 also includes adipose tissues, for example in the form of lipocytes (fat cells) and intracellular or intercellular lipids, which form between the collagen fibers. A network of small blood vessels or capillaries provides circulation, extending from the subcutis 18 into the dermis 16.

Depending on application, the current stimulus S can be generated by one or more electrodes 120 disposed along the skin surface 12. A topical skin treatment 20 can be applied to the skin surface 12 to improve conductivity, and to provide the skin 10 with nutrients and other beneficial agents.

As shown in FIG. 1, the current stimulus S propagates through the skin surface 12 to the epidermal layer 14, and through the epidermal layer 14 to one or both of the dermis 16 and subcutis 18. The stimulus S can thus promote a range of beneficial responses in the epidermal, dermal (cutaneous) and subcutaneous tissues.

The current treatment S can be applied as a steady-state (constant or alternating) voltage signal; e.g., using a modulated waveform, for example a charge-balanced microcurrent waveform generated by two or more electrodes 120 spaced along the skin surface 12. Alternatively the current treatment may be galvanic or polarized (not charge balanced). One or more of the electrodes 120 can be disposed on or adjacent the skin surface 12 in a selected treatment location, for example on the face, arm, torso or leg. Another electrode could be disposed adjacent the first electrode, or coupled through the skin surface via the subject's hand, or other body portion.

Device 100 can be configured to generate a current or voltage signal to the electrodes 120, with output characteristics adapted to deliver a selected current or voltage to the skin surface 12, and to accommodate variations in the skin resistance (that is, in the resistive load between electrodes 120). Practical output performance is limited by the voltage used to supply the current, and according to the resistive load according to Ohm's Law:

$$V = I \times R, \qquad (1)$$

The output power associated with a given current or voltage signal may thus vary, depending on the electrical resistance of the load. This relationship is defined by the following power equation:

$$P = I^2 \times R, \qquad (2)$$

where I is the current output, R is the resistance, and P is the electrical power delivered to the load (e.g., the user's skin). Alternatively, $$P = I \times V. \qquad (3)$$

The resistance R may also vary depending on skin thickness, moisture level, and the presence (or absence) of facial and body hair, as well as the characteristics of any topical agent or skin treatment 20 that is applied.

More generally, for real-time modulation of pulsed microcurrent, pulsed DC and DC current treatments, and other, time-varying, modulated power applications, the complex impedance Z should be used; that is, the complex combination of resistance R and reactance, which has both and inductive component $X_L$, and a capacitive component $X_C$:

$$Z^2 = R^2 + (X_L - X_C)^2. \qquad (4)$$

The inductive and capacitive components of the reactance may vary as a function of frequency, and the current and voltage may be out of phase.

In some cases, the changes in skin resistance R or impedance Z may be substantial, and can occur over a relatively short time period; e.g., depending on the speed at which the device 100 moves across the skin 10, the treatment area of the skin surface 12 and applied pressure at the electrodes 120, the dryness, moisture level and thickness of the skin 10, and other operational parameters. The changes can result in rapid voltage, current and power transients, which have been associated with stinging or prickling sensations, and (in some cases) potential user discomfort. There may also be tradeoffs between user comfort and treatment efficacy, based on the applied current level.

Control circuitry can be adapted to help address these concerns, by regulating the applied current I and voltage V in order to maintain a substantially constant power output P, which is selected to maintain treatment efficacy and user comfort, while reducing transients. A feedback loop can be included, in order to adapt the power regulation technique for a range of devices 100 adapted for pulsed, modulated, current-balanced microcurrent skin treatments, or for modulated DC, pulsed DC (single or dual polarity) or galvanic treatments, as described herein.

Device Applications

Figure 2:
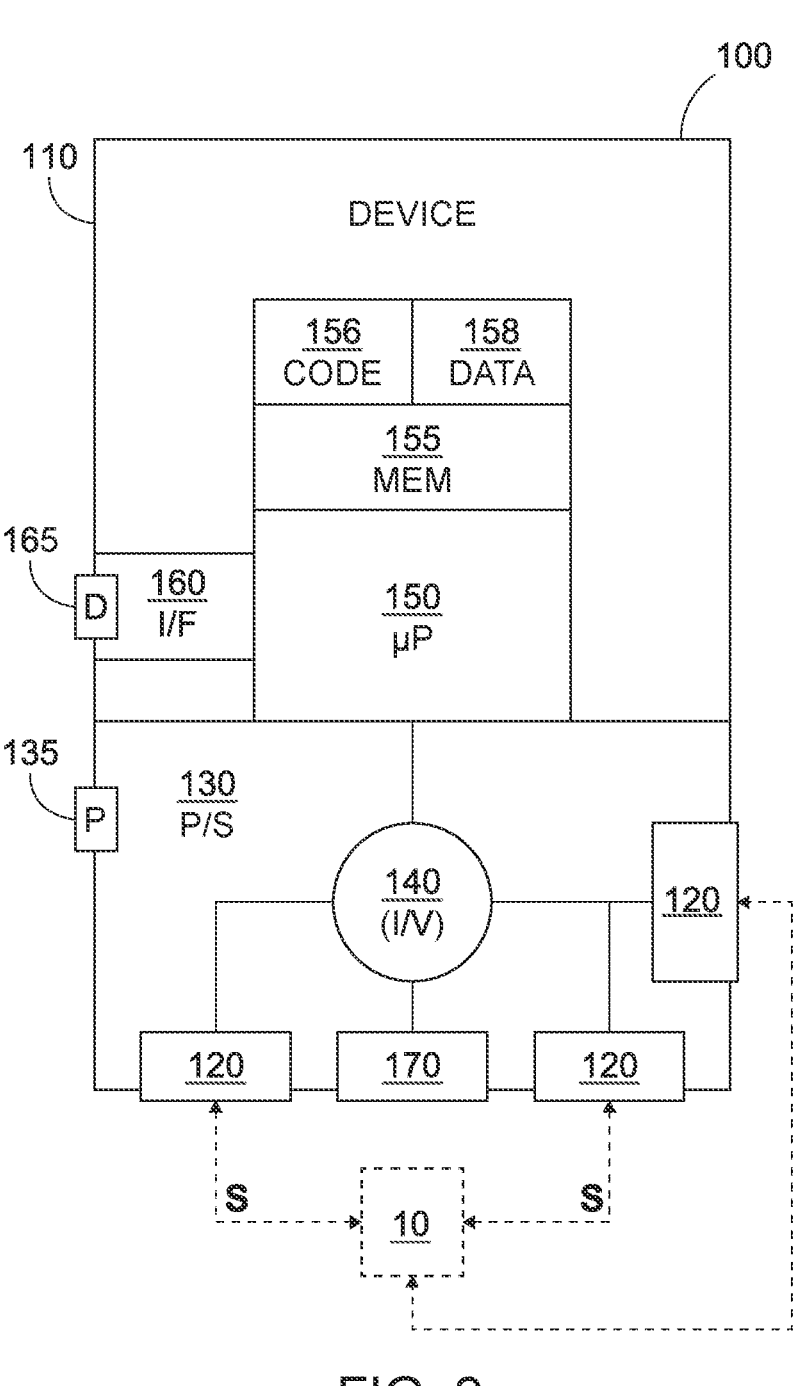
FIG. 2 is a block diagram of a device for application of the current treatment to the skin surface.

FIG. 2 is a block diagram of a representative skin treatment device 100 having a housing 110 with one or more electrodes or emitters 120. Electrodes 120 are adapted to provide an electrical stimulus S to the skin 10 of a subject, for example according to a device 100 as shown in FIG. 1.

As shown in FIG. 2, microcurrent device 100 also includes a power supply (P/S) 130, a current or voltage source (IV) 140 electrically connected to one or more of the electrodes 120, a microprocessor (P) based controller 150 with memory 155 and an external communications interface (I/F) 160.

Power supply 130 can be provided in the form of a rechargeable capacitor or battery system, for example with a wireless charger 135 adapted inductive charging, or another wired or wireless charger port (P) 135. The microprocessor controller 150 is provided in data communication with the memory 155, which provides storage for control code 156 and operational data 158. The communications interface (I/F) 160 can be adapted for both data and control communications with the controller 150, for example using a hard-wired communication port or wireless communications device (D) 165. One or more sensors 170 can also be included, for example as configured to determine skin and environmental or operational conditions such as resistivity, surface temperature, hydration, ambient temperature, humidity, etc.

Depending on embodiment, the device 100 can include a plurality of at least two electrodes 120 adapted for application of a current signal to a skin surface of a subject, and a voltage or current source (or waveform generator) 140 configured to generate the current signal for application via the at least two electrodes, where power is output to the surface of the skin 10. In operation of device 100, power supply 130 provides power to the voltage or current source 140, as well as the microprocessor controller 150, memory 155 and interface 160.

Controller 150 is configured regulate the potential (V) or current (I) signal generated by source 140, for example by executing control code 156 stored in memory 155. Control parameters and other operational data 158 can be used for modulating the signal provided to each selected electrode or emitter 120, in order to deliver the desired microcurrent pulse waveform (e.g., using voltage and current feedback from the electrodes 120 and sensor data from sensors 170).

In particular applications, the controller/microprocessor 150 can to modulate the power output to the surface of the skin 10 using a monitor circuit to generate a feedback signal responsive to changes in the current signal (or the power output to the surface of the skin 100), in order to maintain the comfort level of the subject, based on the power output. The control circuit 150 can include a level controller configured to modulate the current within a predefined range (e.g., a predefined comfort range), based on the feedback signal. The level controller can be coupled to a current control device configured to modulate the current, for example to the gate of a three-terminal current control device coupled between the monitor circuit and one or more of the electrodes. The level control can thus define a response curve of the current control device, within the predefined range.

The control circuit 150 can be configured to modulate or adjust the current signal to an adjusted, lower or minimum value within the predefined comfort range, responsive to a predefined change in the current signal, or a change in the power output to the surface of the skin 10. The change can be associated with a decrease in the comfort level, or a likelihood of discomfort. Thereafter, control circuit 150 can be responsive to detecting, from an average of samples of the voltage sensed or detected by the monitor circuit, at, adjacent or across one or more of the electrodes 120, and after modulation to the adjusted, lower current signal value, such that the then-current signal or the power output to the skin surface is no longer associated with a likelihood of discomfort, in which case the control circuit 150 can be configured to modulate the current to an adjusted, higher or maximum current value within the predefined comfort range, if such a value is available within the comfort range.

Methods of Application

Figure 3:
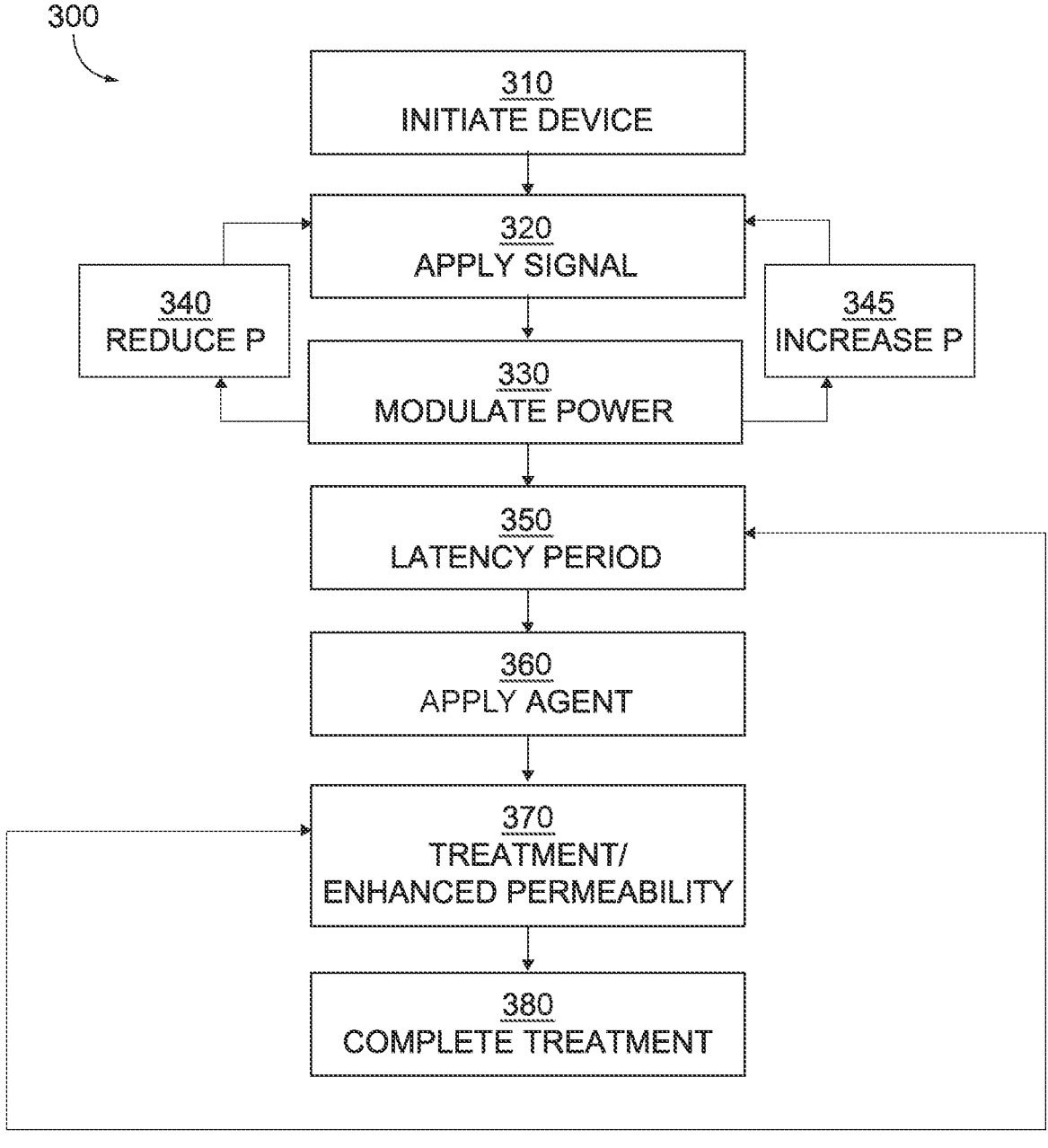
FIG. 3 is a block diagram of a method for applying the current treatment to the skin surface.

FIG. 3 is a block diagram of a method 300 for enhancing permeability to one or more components of a topical agent applied to a skin surface. The method can include initiating (turning on) a device with one or more electrodes onto or adjacent the skin surface (step 310), applying a voltage or current signal to the skin surface via one or more of the electrodes (step 320), and modulating the power output (step 330) to the skin surface; e.g., so that the power output provides a charge-balanced, pulsed DC, modulated DC, or otherwise modulated power output adapted to enhance user comfort while maintaining treatment efficacy. The power can be modulated to reduce the power output (step 340), or to increase the power output (345), in order to maintain treatment efficacy while reducing transients, as described herein.

Depending on application, the method can also include defining a latency period (step 350), following application of the voltage or current signal (step 320); e.g., during which no further voltage or current is applied to the skin surface via the one or more electrodes. The method can include applying an agent to the skin surface (step 360), either directly after applying the signal or following the latency period (step 350). The agent is applied during a treatment period (step 370), where permeability of the skin to one or more components of the agent is enhanced or increased, responsive to the modulated power output (step 330). The treatment can be completed (step 380) at any suitable time; e.g., by removing the agent. Note, however, that enhanced permeability may still be exhibited after the treatment period, for components that have already penetrated one or more layers of the skin surface, or are not removed.

In any of these examples, the enhanced or increased permeability can be expressed as enhanced or increased absorption, adsorption, diffusion or transmissibility of the one or more components of the agent, into or through one or more of layers of the skin surface to which the voltage or current signal is applied. The enhanced or increased effect can extend during all or any part of the treatment period, as compared to said absorption, adsorption, diffusion or transmissibility that would be expressed absent (without) application of the voltage or current signal.

The layers of the skin surface can include any one or more of the stratum corneum, the outer epidermis, the lower epidermis, and/or the dermis. The one or more layers of the skin surface can also include vasculature or fibroblasts.

In any of these examples, modulating the power output to the skin surface (step 330) may be based on a feedback signal responsive to change in the applied voltage or current signal. The change can be based at least in part on the voltage or current signal; e.g., as sensed proximate one or more of the electrodes. The power can be regulated to modulate transients, for example by defining a response curve for the power output, wherein the response curve defines the power output between predetermined minimum and maximum power levels, based on the feedback signal.

Depending on application, a threshold can be defined for change in the feedback signal; and the power output can be reduced (step 340), based on a change in the feedback signal meeting or exceeding the threshold; e.g., by lowering the response curve to or toward the predetermined minimum power level. Alternatively, the power output can be increased (step 345), based on the change in the feedback signal not meeting or exceeding the threshold; e.g., by lowering the response curve to or toward the predetermined maximum power level. In particular examples, modulating the power output to the skin surface (step 330) can be achieved with a three-terminal device having a first terminal coupled to a voltage sensor adjacent one or more of the electrodes, a second terminal coupled to the feedback signal, and a gate adapted to control the power output.

A waveform can be defined for applying the voltage or current signal to the skin surface (step 320), where modulating the power output (step 330) comprises modulating the waveform such that the power output is charge-balanced, modulated DC or pulsed DC, and to maintain user comfort and treatment efficacy (or both). The waveform can include alternating sequences of positive and negative polarities; e.g., where the positive and negative polarities of the alternating sequences are charge balanced, or a series of pulses having the same polarity. The alternating sequences of positive and negative polarities may be symmetric, or the waveform can include pulses of positive and negative polarities having randomized or pseudorandom pulse width or pulse height, or both.

The positive and negative components of the waveform can be modulated (step 330) so that the voltage or current waveform is charge balanced over a period of about 0.1-0.2 s, or less, a period of about 0.2-0.5 s, or less, a period of about 0.5-1.0 s, or less, a period of about 1.0-1.5 s, or less, or a period of about 1.4 s. Alternatively, the period may be more about 0.1-0.2 s or more, about 0.2-0.5 s or more, about 0.5-1.0 s or more, about 1.0-1.5 s or more, or more than 1.5 s.

The voltage or current signal applied to the skin surface (step 320) can include voltage or current pulses with amplitudes up to about 100 μA, about 100-150 μA, or less, about 150-200 μA, or less, about 200-250 μA, or less, or up to about 375 μA. Other suitable amplitudes range up to about 100 μA or more, about 100-150 μA or more, about 150-200 μA or more, about 200-250 μA or more, or more than about 375 μA.

The voltage or current signals applied to the skin surface (step 320) can be formed of or comprise voltage or current pulses have individual pulse widths between about 1-10 ms, or less, between about 10-20 ms, or less, between about 20-50 ms, or less, between about 50-100 ms, or less, or about 100 ms or less. Alternatively, other suitable pulse widths may be about 1-10 ms or more, between about 10-20 ms or more, between about 20-50 ms or more, between about 50-100 ms or more, or more than about 100 ms.

The voltage or current signals applied to the skin surface (step 320) can include alternating sequences of voltage or current pulses, where the alternating sequences each comprise between two and six individual pulses, or less, between five and ten individual pulses, or less, between six and twelve individual pulses, or less, between ten and twenty individual pulses, or less, between twenty and fifty individual pulses, or less, or fifty individual pulses or less. Alternatively, other suitable alternating sequences can include two to six pulses or more, five to ten pulses or more, six to twelve pulses or more, ten to twenty pulses or more, twenty to fifty pulses or more, or more than fifty pulses.

Applying the voltage or current signal (step 320) and modulating the power output to the skin surface (step 330) can be performed for a predetermined period (or "pretreatment" period) before applying the agent (step 360), after any latency period (step 350). The pretreatment period can be selected to achieve enhanced or increased permeability of the skin following the latency period, for the one or more components of the agent. For example, the pretreatment period can be selected for enhanced or increased absorption, adsorption, diffusion or transmissibility of the one or more components of the agent into or through one or more of layers of the skin surface during the treatment period, as compared to said absorption, adsorption, diffusion or transmissibility absent applying the voltage or current signal to the skin surface.

Suitable pretreatment periods include, but are not limited to, between about one to two minutes, or less, between about two to three minutes, or less, between about three to five minutes, or less, between about five to ten minutes, or less, or about ten minutes or less. Other suitable pretreatment periods include, but are not limited to, between about one to two minutes or more, between about two to three minutes or more, between about three to five minutes or more, between about five to ten minutes or more, or more than about ten minutes.

The components of the agent for which permeability is enhanced or increased upon application to the skin surface (step 360) and during the treatment period (step 370) can include ions and ionic or polar molecules. Alternatively, the components exhibiting enhanced or increased permeability may include nonionic and/or nonpolar molecules. Additional suitable components include, but are not limited to, proteins, amino acids, genetic material, genetic markers, allantoin, and caffeine.

The treatment period (step 370) can extend one to two hours or more after application of the voltage or current signal to the skin surface, two to four hours or more after application, four to eight hours or more after application, six to twelve hours or more after application, twelve to twenty-four hours or more after application, or twenty-four hours or more after application. Other suitable latency periods can commence one to two hours or less after application of the voltage or current signal to the skin surface, two to four hours or less after application, four to eight hours or less after application, six to twelve hours or less after application, twelve to twenty-four hours or less after application, or twenty-four hours or less after the application.

The latency period (Step 350) can extend for one to two hours or more following application of the voltage or current signal, two to four hours or more following application, four to eight hours or more following application, six to twelve hours or more after application, twelve to twenty-four hours or more after application, or twenty-four hours or more after application. Other suitable latency periods can extend for one to two hours or less following application of the voltage or current signal, two to four hours or less following application, four to eight hours or less following application, six to twelve hours or less after application, twelve to twenty-four hours or less after application, or twenty-four hours or less after application.

A topical can also be applied to the skin surface; e.g., either before or after initiating the device (step 310), or while applying the voltage or current signal (step 320) and modulating the power output (step 330), or together with the agent (step 360), The topical can thus be applied before applying the voltage or current signal, while applying the voltage or current signal, or during the latency period. For example, the topical may include a conducting gel, serum, moisturize, or base. The topical may also include allantoin, caffeine, collagen, moisturizes, or other skin treatment products.

A conducting gel or conducting fluid can also be applied to the skin surface during or prior to applying the voltage or current signal. For example, the conducting gel or conducting fluid forms an electrically conducting path for the voltage or current signal between the one or more electrodes and the skin surface.

Suitable skin treatment methods can include any or all of these steps and techniques, performed in any order or combination, with or without additional treatment steps, as described herein, and as known in the art. A skin treatment system can also be provided with one or more electrodes adapted to apply a voltage or current signal to a skin surface accordingly. For example, the system can include a voltage or current source adapted to generate the voltage or current signal, and control circuitry adapted to modulate the power output to the skin surface. A non-transitory computer-readable medium can be provided with program code stored thereon, where the program code is executable on a computer processor or controller to perform such a method, or to operate such a system.

Power Modulation

Figure 4:
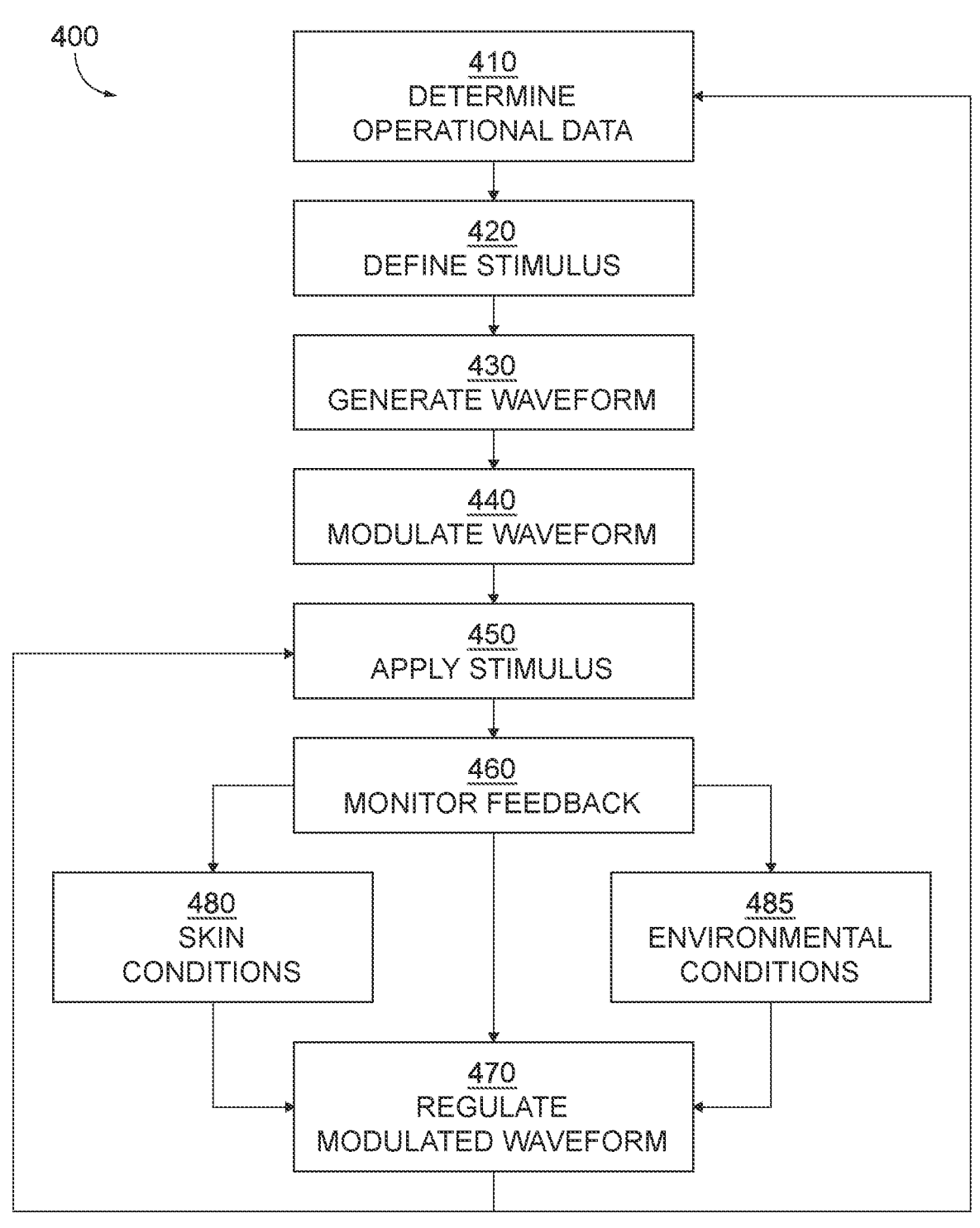
FIG. 4 is a block diagram of a method for modulating power delivered by the current treatment.

FIG. 4 is a block diagram illustrating a representative method or process 400 for modulating power delivered by the current treatment, for example using the device 200 of FIG. 2, or according to the method 300 as shown in FIG. 3. In the particular example of FIG. 4, method 400 comprises one or more steps of determining operational data (step 410), defining a stimulus (step 420), generating a waveform (step 430), modulating the waveform (step 440), and applying a stimulus to the user's skin (step 450), based on the modulated waveform.

Depending on application, method 400 may also include monitoring feedback (step 460), and regulating the modulated waveform (step 470); e.g. in order to reduce differences between the defined and applied stimuli. These steps can be performed in any order or combination, with or without additional procedures. For example, monitoring feedback (step 460) can also include monitoring sensor data, for example to determine skin conditions (step 480) and environmental conditions (step 485).

Determining operational data (step 410) can be performed as an initiation or start operation for method 400, for example by reading the operational data from memory. The operational data can include a set of operational parameters for performing the steps of method 400, or data used to generate such a parameter set. For example, the operational data may include stimulus data or parameters from which a desired stimulus can be selected or defined (step 420), and waveform data or parameters from which a desired voltage or current waveform can be generated (step 430).

The waveform data can also include a set of selected pulse parameters for modulating the waveform (step 440), so that the desired stimulus can be delivered or applied to the skin of a subject (step 450). The pulse parameters can be selected to characterize one or more pulse widths for "on" and "off" portions of the cycle, as well as pulse periods, frequencies and amplitudes.

The applied waveform may be either unipolar or bipolar; for example as defined based on the sign of the amplitude parameter, or by defining an absolute (non-negative) amplitude with a separate polarity parameter to determine the sign. The pulse modulation can be randomized by assigning selected parameters to consecutive pulses in a random or pseudorandom sequence, or by including a random or pseudorandom component in the modulated pulse parameters themselves, in order to generate a non-repeating or aperiodic sequence of modulated pulses.

For example, the pulse width, period, frequency, amplitude or other modulated pulse parameter may be aperiodic or non-repeating over a given set of pulses, so that the modulated parameter does not repeat at all, or does not repeat with any identifiable pattern or sequence, within the given subset or set. The aperiodic or non-repeating pulse parameter can be modulated over a set of consecutive pulses defining a treatment cycle with one or more treatment phases, or over a subset of consecutive pulses defining one or more of the phases.

The applied stimulus (step 450) can be monitored (step 460) by measuring the applied voltage or current flow through the electrodes or other emitters. Feedback parameters can be used to regulate the modulated waveform (step 470), for example by applying a hardware or software-based gain parameter to reduce any difference between the stimulus that is defined (at step 420), and the stimulus that is actually applied (at step 450). Feedback monitoring (step 460) can also include receiving sensor data used to determine skin and environmental conditions such as resistivity, surface temperature, hydration, ambient temperature, humidity, etc. (steps 480 and 485).

The operational data (step 410) can also include historical log data for prior operation of a suitable microcurrent device 300 according to method 400. For example, the log data can be recorded to characterize previously defined stimuli (step 420), and to record the parameters used for waveform generation (step 430) and modulation (step 440). Additional log data can provide records of stimuli that were actually delivered or applied in previous treatments (at step 450), as well as the electrode or emitter and sensor feedback (step 460), and additional parameters used to regulate the modulated waveform (step 470), to determine resistivity and other skin conditions (step 480), and to describe relevant environmental conditions (step 485).

Waveform modulation (step 440) can apply a variety of different pulse modification techniques. In the radio-frequency (RF) range, for example, amplitude modulation (AM) and frequency modulation (FM) are commonly used. In these techniques, the modulated waveform is typically a sinusoidal carrier wave generated at a particular carrier frequency, for example in the kilohertz (kHz), megahertz (MHz), or gigahertz (GHz) range.

In amplitude modulation (AM), the amplitude of the carrier wave can be varied according to an analog (e.g., audio-frequency) signal. The modulated carrier signal is demodulated at the receiver, separating the information-carrying modulation frequencies from the carrier wave. For analog modulations in the audio-frequency range of about 1-10 kHz, typical carrier frequencies extend from the tens of kilohertz (kHz) into the tens of megahertz (MHz) and above.

In frequency modulated (FM) techniques, the instantaneous frequency of the carrier wave is varied, rather than the amplitude. For audio-range applications, FM carrier frequencies traditionally extend from about ten megahertz (10 MHz) and above into the gigahertz (GHz) range. Frequency shift keying (FSK) can also be applied across a range of both lower and higher frequencies, for example to encode digital signals by shifting the carrier frequency among a selected set of discrete adjacent frequencies.

In skin treatment applications, the stimulus is not limited to a narrow-band carrier wave, and can also be defined (step 420) in terms of a pulsed waveform (step 430), to which programmed, randomized pulsed waveform modulation (PRPWM) can be applied (at step 440) in order to deliver the desired stimulus (step 450) to the subject's skin. Programmed, randomized pulsed waveform modulation can also be adapted to provide charge and power balancing, and to incorporate a more advanced understanding of the body's underlying biological mechanisms, including the effects of randomized pulse width modulation on the body's homeostatic response. A pulsed DC or modulated DC treatment can also be applied, either with single polarity or using a dual polarity, modulated signal switching at periodic or aperiodic intervals.

Power Regulation

Figure 5:
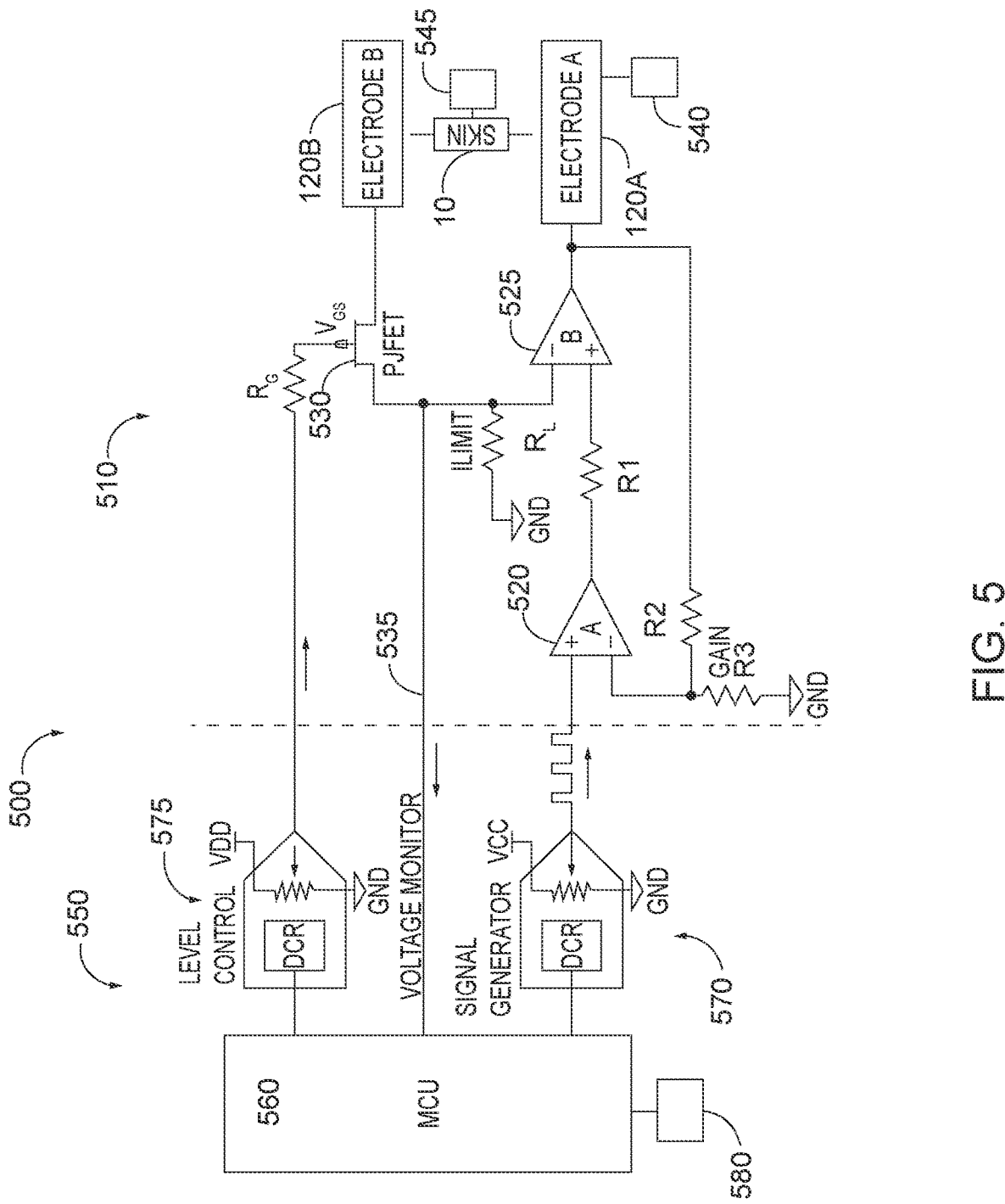
FIG. 5 is an electronic schematic illustrating a circuit for modulating the power.

FIG. 5 is electronic schematic illustrating a representative power modulation circuit 500; e.g., for regulating the power output of a skin treatment device 100 according to FIG. 2, or according to method 300 of FIG. 3. As shown in FIG. 4, control circuit 500 is divided into a front-end (hardware) section 510, and a back-end (software) section 550.

Front-end section 510 of control circuit 500 includes a sequence of operational amplifiers (op amps) 520, 525 coupled to a first electrode 120A (electrode A), and a current control device 530 coupled to a second electrode 120B (electrode B). Electrodes 120A, 120B are adapted to provide a current stimulus to a subject's skin 10. The power output is regulated using a feedback circuit 535, in order to modulate power transients and improve user comfort, while maintaining treatment efficacy.

Back-end section 550 of control circuit 500 includes a programmable microprocessor or microcontroller (MCU) 560, a signal generator 570 and level control 575, and a voltage monitor or feedback circuit 535. Front-end section 510 includes a sequence of operational amplifiers (op amps) 520, 525 coupled to a first electrode 120A (electrode A), and a current control device 530 coupled to a second electrode 120B (electrode B). Electrodes 120A, 120B are adapted to provide a current stimulus to a subject's skin 10, which is modulated by control circuit 500 to reduce power transients and increase user comfort while maintaining treatment efficacy, as described herein.

The front-end section 510 of control circuit 500 operates continuously, in an analog configuration. The back-end section 550 operates sequentially, in a digital configuration based on a digital sampling rate of the signal generator 570, which is coupled to electrode A via the op amps 520, 525, utilizing a series of resistors R1, R2, R3 to control feedback and determine the gain. The signal itself can be generated as a modulated waveform for applying a microcurrent treatment, or a galvanic signal, as described above.

The level control 575 is coupled to the current control device 530 via a resistor RG, generating gate voltage $V_{GS}$. The feedback circuit 535 is connected between the (second) op amp 525 and the current control device 530, with a current-limiting resistor (ILIMIT) $R_L$ connected to ground (GND). The MCU 560 in control circuit 500 can be adapted to measure the voltage drop across the current limiting resistor $R_L$ in FIG. 5); e.g. a fixed value resistor. The software routines coded into (or for operation of) the MCU 560 can be adapted to translate this voltage reading into a current level using Ohm's law, for example a microampere ($\mu$A) or milliamp (mA) reading, or other suitable scale. These readings are then digitized and fed into moving average filters with short and long-term averaging rates, which contain the running average of the respective samples (e.g., the last nine and thirty samples, respectively, or at other suitable sampling rates such as the last two to ten samples and the last ten to fifty samples, or more or less). See FIG. 7.

In order to maintain a more constant power control while preventing or avoiding skin sensations associated with discomfort due to transients, control circuit 500 is adapted to provide a power control parameter or signal to the current control device 530; e.g., ranging from a minimum value (MIN) to a maximum value (MAX), as described above. In operation of the circuit 500, the parameter value or level can be shifted up or down based on the voltage monitor (or other feedback signal) from circuit 535.

While the control circuit 500 may not directly measure power per se, power has a mathematical relationship that is defined by the skin resistance (or impedance) and the amount of current applied. While the impedance of the skin 10 can be determined independently of operation of the control circuit 500, the front-end section 510 actively regulates the power applied to the skin 10. The hardware power regulation is further enhanced through the software-controlled back-end section 550; e.g., by measuring the voltage and/or skin current via the feedback circuit 535, and conditionally controlling the power levels applied to the skin 10 based on the feedback signal, via the gate voltage $V_GS$ provided to the control device 530.

The output shifting is done by manipulating the gate input voltage $V_{GS}$ of the current control device 530. For example, if the gate voltage $V_{GS}$ is set at −V3 according to FIG. 4, the current level output by device 530 will be lower than when the gate voltage $V_{GS}$ is set at VO. This shifting of control parameter values corresponds to the shifting of current and power levels between the minimum (MIN) and maximum (MAX) curves, as shown in FIGS. 3A and 3B. In other words, by manipulating the gate voltage $V_{GS}$ at device 530, the power levels can be established and shifted to reduce transient effects, and to increase the dynamic range of the current output.

To address transients, one or more of the following features can also be included, either in the constant power supply modulation circuit 500, or elsewhere on the device, and coupled in data communication with the MCU 560, e.g., via the feedback circuit 535.

An accelerometer or velocity sensor/detector 580 could also be employed as part of the feedback circuit 535. When the user moves the device too quickly, poor electrode contact can occur, causing a hyperpolarization event. In this case (e.g., when a preselected velocity or acceleration value is reached or exceeded), the power modulation circuit 500 can be adapted to alert the user, and to throttle back (reduce) the power output until the movement returns to a regular, recommended range for velocity and/or acceleration.

A pressure sensor 540 can be adapted to sense proper contact between one or more of the electrodes 120A, 120B and surface of the skin 10, for example based on a predefined range for force or loading on the electrode surface. In the case of improper contact (force or loading outside the predefined range), the system can alert the user and/or throttle back (reduce) the power output, until such time recommended pressure is re-established (force or loading within the predefined range).

A skin sensor 545 can be employed to accomplish additional feedback for the power modulation circuit 500, in order to help prevent or reduce hyperpolarization events. In these examples, the skin sensor could also be adapted to measure skin temperature, roughness, resistivity, or other operational parameter related to the skin surface 10, and used to modulate the feedback voltage according to a predefined function relating the measured skin parameter to the load or impedance, or to skin sensitivity.

Waveform Modulation

Figure 6:
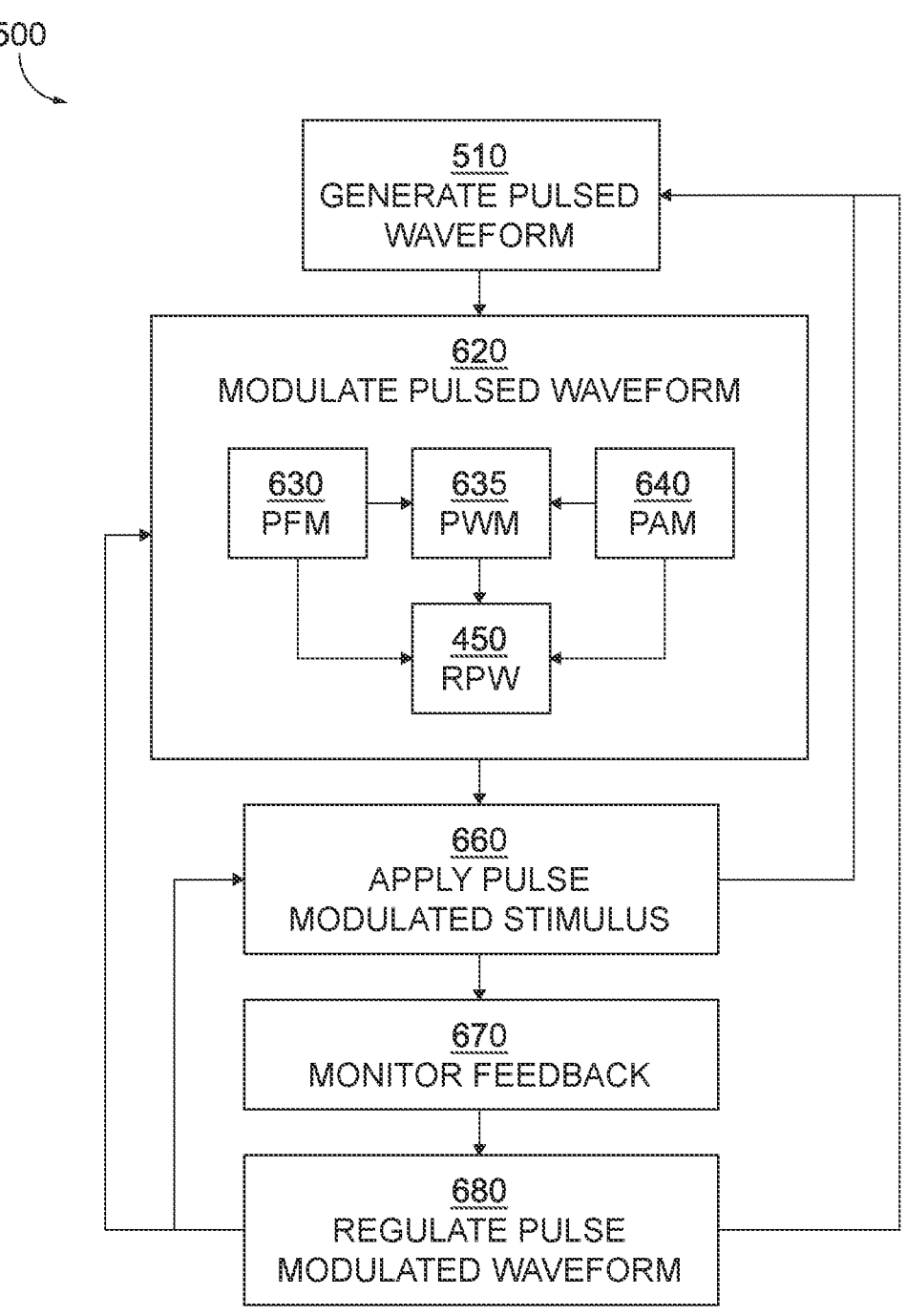
FIG. 6 is a block diagram illustrating a method for waveform modulation.

FIG. 6 is a block diagram of a method or process 600 for waveform modulation. For example, method 600 may be used to operate a device 100 having one or more electrodes or emitters 120, as shown in FIG. 2, and adapted to apply a pulse modulated electrical stimulus to a subject's skin, according to either of FIGS. 3 and 4. Similarly, method 500 can also be adapted to modulate a waveform for microcurrent-based skin treatment, for example according to the circuit 500 as shown in FIG. 5.

In the example of FIG. 6, method 600 includes generating a waveform (step 610), modulating the waveform (step 620), and applying a pulse modulated stimulus (step 660). These steps can be performed in any order or combination, with or without additional processes. For example, method 400 may also include monitoring a combination of sensor and electrical feedback (step 670), and regulating the modulated waveform (step 680) based on the feedback; e.g., in order to match the predefined and applied stimuli according to method 300 or method 400.

Generating a waveform (step 610) comprises providing an electrical signal, for example using a voltage or current generator as shown in FIG. 5. The waveform can be sinusoidal or non-sinusoidal, for example a square wave, rectangular wave, saw-tooth, or triangular waveform, or other periodic or aperiodic function, or a modulated DC waveform can be used. The waveform can also be generated with either positive or negative polarity, or in bipolar form, and may be referenced to ground or superposed on a DC signal with either positive or negative bias.

Waveform modulation (step 620) encompasses a range of modulation techniques including pulse frequency modulation (PFM; step 630), pulse width modulation (PWM; step 635), pulse amplitude modulation (PAM; step 640), and combinations thereof. In particular examples, random or pseudorandom pulse width modulation (RPW) 650 can be applied to enhance biological response when the stimulus is applied to a subject's skin, (step 660), and to reduce the tendency for homeostasis.

In pulse frequency modulation (PFM) 630, the frequency of the pulsed waveform can be varied either independently of the pulse width and amplitude, or in combination. Variations in the frequency are reflected by changes the period between consecutive pulses, and can be performed according to either an analog or digital modulation signal, for example by frequency-shift keying (FSK), in which the pulse-to-pulse frequency is varied among a selected set of discrete digital frequency changes.

Pulse width modulation (PWM; step 635) is a technique for selectively distributing power over the individual pulses in a pulsed waveform or carrier wave, according to a desired (e.g., analog or digital) modulation function. The average value of the power delivered is determined according to the time integral of the modulated voltage and current waveforms, while the instantaneous power is determined by the respective amplitudes at a particular time. Since the pulse width is also reflected in the length or duration of the signal, pulse width modulation can also be described as pulse duration modulation (PDM).

In pulse amplitude modulation (PAM) 640, the amplitude of the pulsed waveform (or carrier wave) can be varied from pulse to pulse, either independently of or in combination with one or more the pulse width, pulse period and carrier frequency. Pulse amplitude modulation (PAM) can also be applied as an analog or digital modulation technique, for example by amplitude-shift keying (ASK), in which the pulses are modulated according to a selected set of discrete amplitudes, each assigned to a different digital value.

In randomized pulse width modulation (RPW; step 650), the widths of individual waveform pulses are modulated according to a randomized or pseudo-random scheme. The pulse width and duty cycle of the waveform can be randomized independently of the pulse frequency and amplitude, or the techniques can be combined, as described below.

The modulated waveform can be applied (step 660) in the form of an electrical voltage or current, for example as delivered to a subject's skin by one or more electrodes or emitters 120, as shown in FIG. 2. Feedback from the electrodes 120 and one or more sensors 170 can also be monitored (step 670), in order to determine differences between the defined stimulus and the stimulus that is actually applied.

The modulated pulse width can be regulated (step 680) according the feedback, in order to match the applied stimulus to the desired effect. For example, the amplitude of a given voltage stimulus can be regulated according to the skin's resistivity, in order to deliver a desired current stimulus. Alternatively, any combination of the pulse width, frequency and amplitude of the applied stimulus can be regulated according temperature, hydration level, and other skin and environmental conditions, or based on the presence or absence of a topical treatment between the treatment electrodes (or other emitters) and the skin surface.

Randomized pulse width modulation (RPW) 650 can also encompass any combination of pulse frequency modulation (PWM) 635, pulse width modulation (PFM) 630, and pulse amplitude modulation (PAM) 640, as described above. For example, a set of individual "on" and "off" pulse widths can be defined within a particular range, and then randomly sequenced for application to consecutive pulses in the waveform, using a machine-based pseudorandom number generator (PRNG), or a hardware-based ("true") random number generator (HRNG).

Alternatively, the pulse widths can be defined with a randomized or pseudorandom component, and applied sequentially to the consecutive pulses, with or without an additional sequential randomization step. Similar randomization techniques can also be used to modulate of the pulse amplitude, pulse period and frequency, producing a modulated waveform with any suitable combination of constant, deterministic and random or pseudorandom pulse amplitude, frequency and width.

If the total pulse period ("on" plus "off") period is fixed, for example, the pulse width can nominally be modulated independently of the instantaneous (pulse-to-pulse) carrier frequency, although the changing pulse width will still be reflected in the Fourier transform. If the total period ("on" plus "off") is not fixed, both the pulse width and the instantaneous carrier frequency will change from pulse to pulse. Similarly, while the pulse amplitude can nominally be modulated independently of the pulse width and instantaneous carrier frequency (based on the pulse-to-pulse period), the frequency of any amplitude modulation will be reflected as sidebands in the Fourier transform. All of these randomized modulations of the applied stimulus can enhance the skin's response, and provide additional benefits for skin treatment, as described according to the various examples herein.

Testing

Figure 7A:
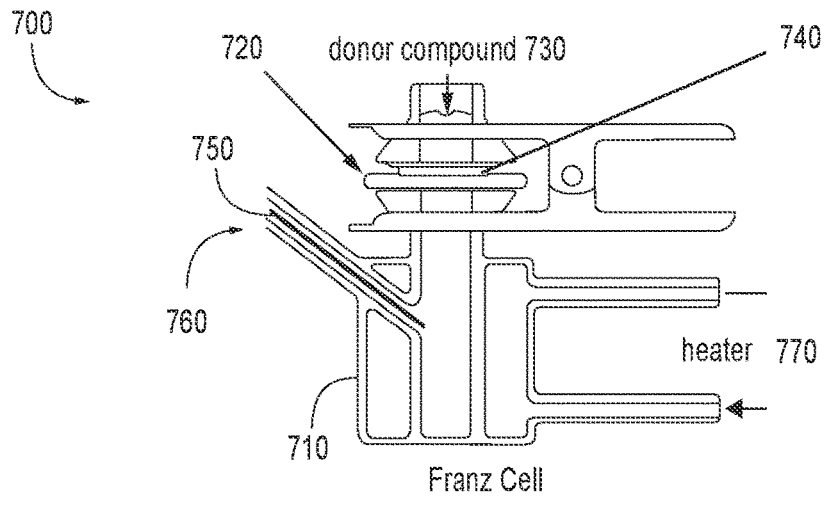
FIG. 7A is a schematic diagram of a Franz cell adapted for testing permeability of a skin sample.

FIG. 7A is a schematic diagram of a Franz cell (or cell system) 700 adapted for testing permeability of a skin sample 710. As shown in FIG. 7A, system 700 includes a Franz cell 710 adapted to support a skin sample 720 (e.g., human or mammalian skin) to which an agent or donor compound 730 is applied.

An electrical voltage can be applied to or across the sample 720 via an electrode 740 in contact with the skin sample 730, and a conducting lead 750 disposed in a sampling port 760. Suitable materials for electrode 740 and lead 750 include platinum, silver, copper, and other conducting metals, in porous mesh, wafer, plate, or wire form. A heater 770 can be provided to maintain temperature of the Franz cell 710, sample 720 and donor compound 730, during operation of the system 700.

Figure 7B:
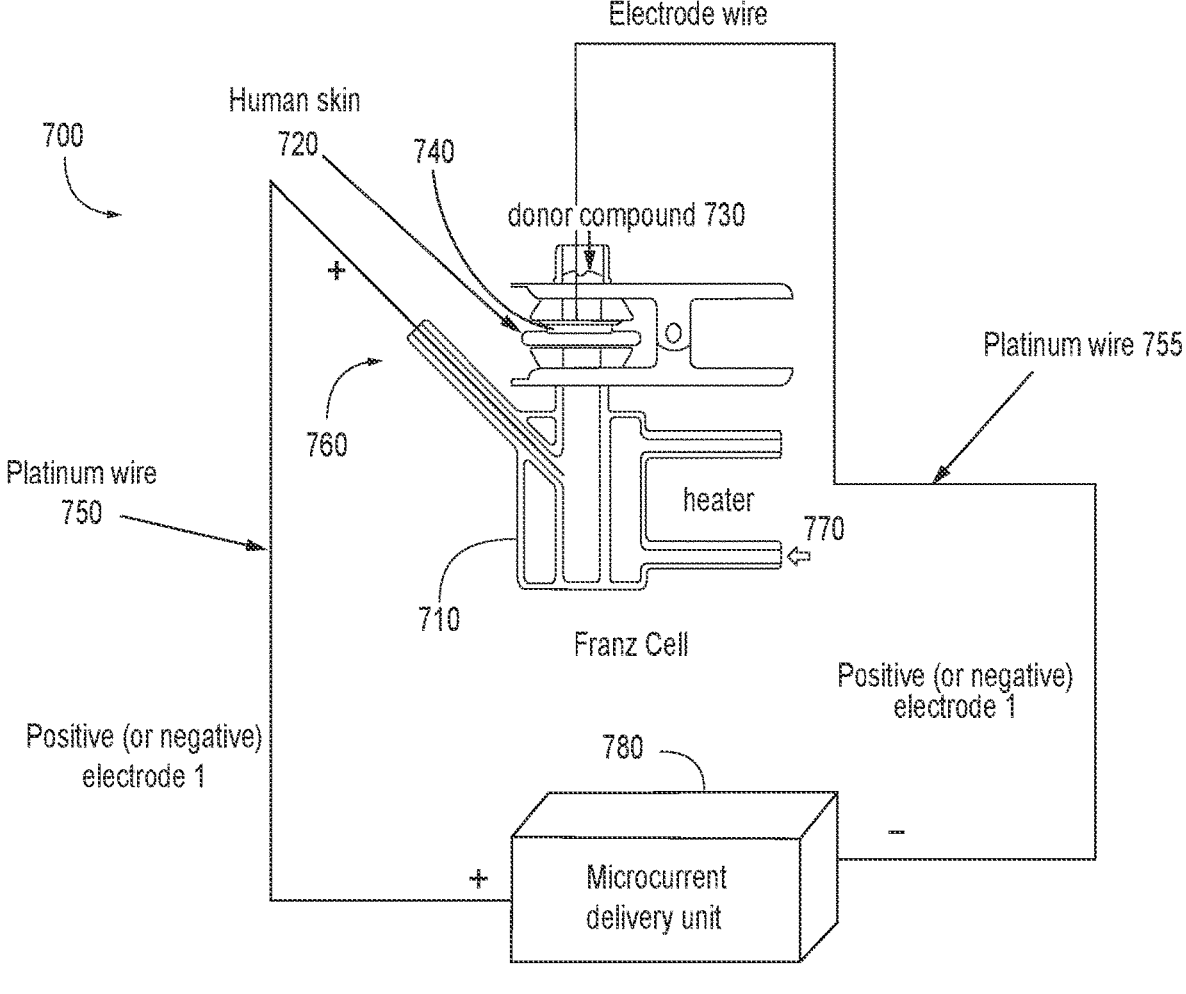
FIG. 7B is a schematic diagram of a Franz cell system adapted for application of a microcurrent treatment to the skin sample.

FIG. 7B is a schematic diagram of a Franz cell system 700 adapted for application of a microcurrent treatment to the skin sample 710. In this example, a galvanic unit or waveform generator 780 can be provided to apply a microcurrent waveform to the skin sample 720; e.g., via a negative polarity platinum wire 755 connected to a porous mesh or wafer electrode 740 on the skin surface, with opposite polarity (+) defined by a platinum lead wire or wire electrode 755. Different metals such as copper or silver can also be used, or other suitable conductors. The polarity can also be reversed, or the lead wire 750 can be used to define a ground potential for the Franz cell 710.

Figure 8A:
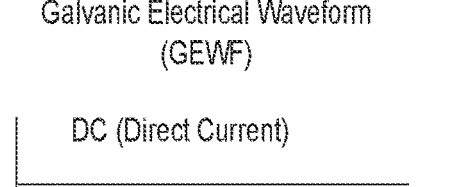
FIGS. 8A, 8B and 8C are schematic diagrams illustrating representative waveforms for application to a skin surface.
Figure 8B:
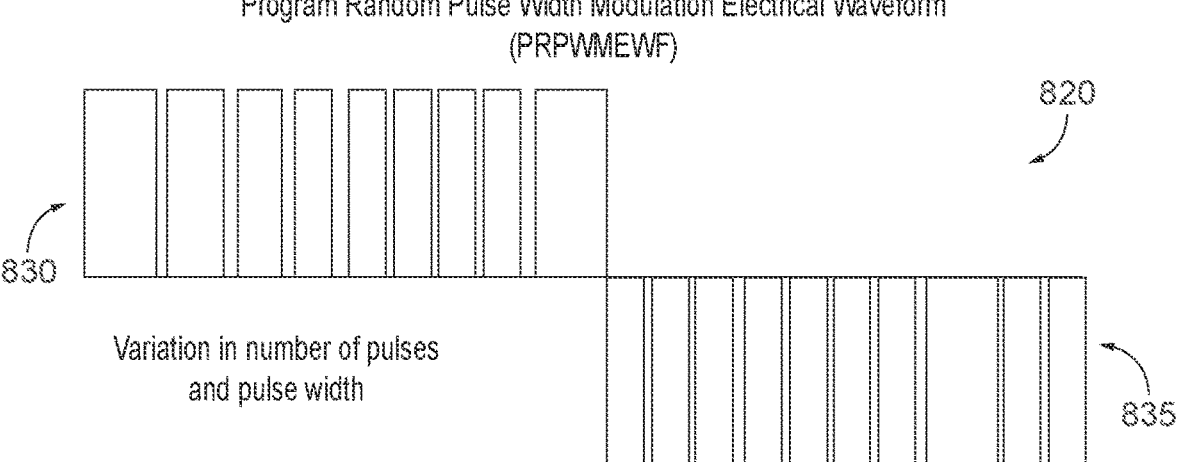
Figure 8C:
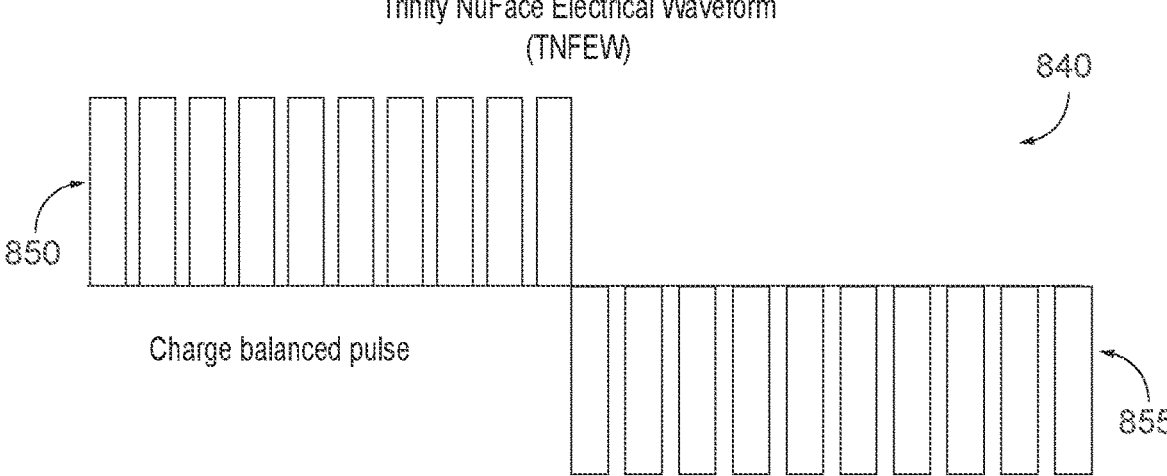

FIGS. 8A, 8B and 8C are schematic diagrams illustrating representative waveforms 810, 820, 830 for application to a skin surface. FIG. 8A illustrates a traditional DC or galvanic waveform, which is not charge balanced.

FIG. 8B illustrates a charge-balanced waveform 820 with a sequence of positive polarity pulses (or positive phase) 830 and a sequence of opposite (negative) polarity pulses (or negative phase) 835; e.g., a program random pulse with modulation electrical waveform (PRPWMEW), with variations in the number and/or width of the individual pulses in each phase 830, 835. The pulse heights or pulse widths may vary in a random or pseudo-random manner, while the integrated pulse heights can be selected or controlled to have the same or substantially similar value for each of the opposite polarity sequences or phases 830 and 835. As a result, the waveform is charge-balanced over the complete cycle time, including both the positive and negative sequences.

FIG. 8C illustrates a charge-balanced, symmetric waveform 840 with a sequence of positive pulses 850 and a sequence of opposite (negative) pulses 855; e.g., a charge-balanced, symmetric electrical waveform (CSW), with charge-balanced positive and negative phases 850, 855. The pulses are symmetric, having the same pulse heights, pulse widths, and number of pulses in each sequence. The pulse periods can also be symmetric, or they may vary. Suitable amplitudes range from about 100 μA or less to about 375 μA or more; that is, in the microcurrent range, typically an order of magnitude or more lower than other more traditional techniques, which apply currents in the milliamp (mA) range, or higher.

Round One Testing

Figure 9A:
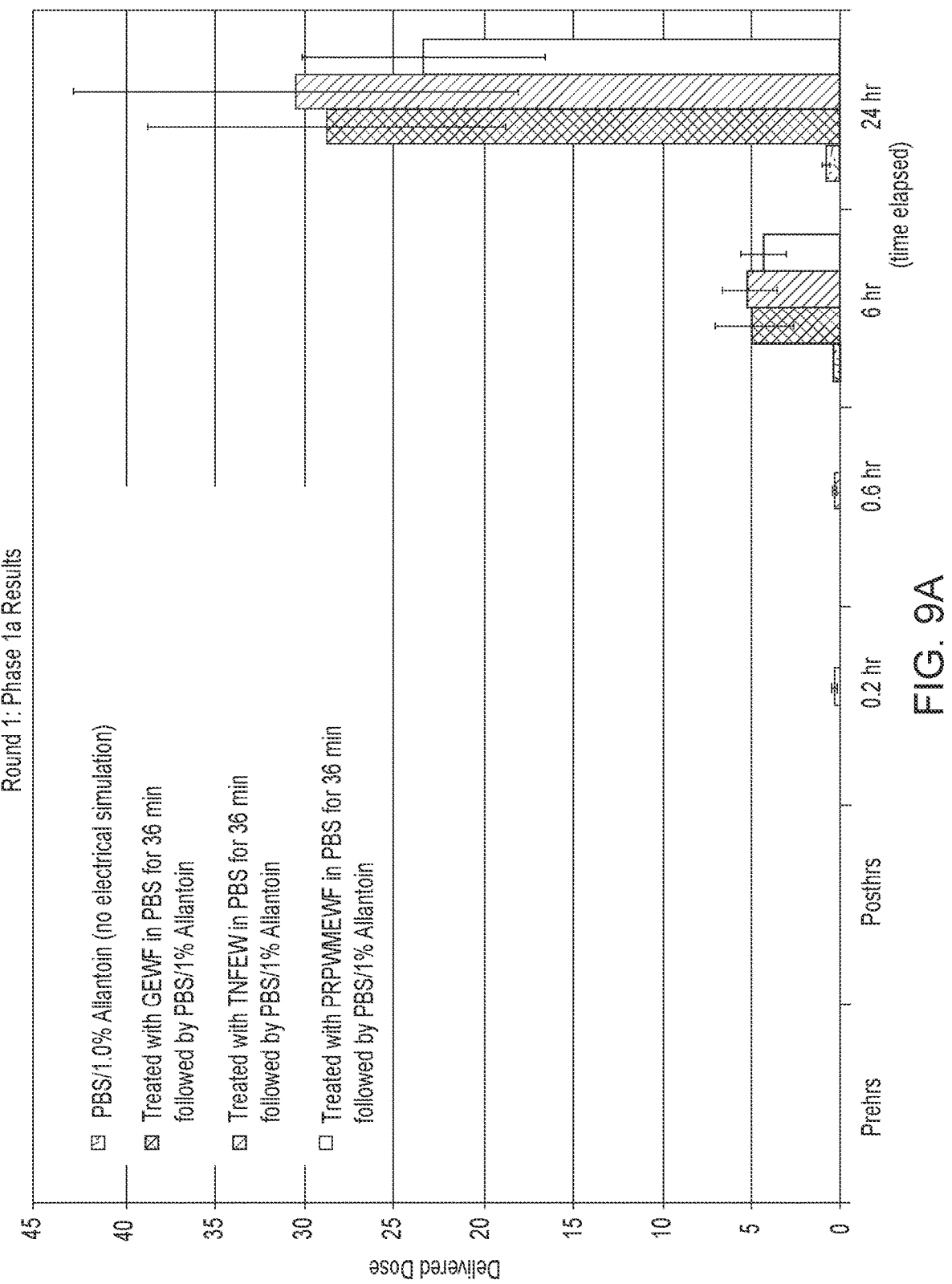
FIGS. 9A and 9B are bar charts illustrating transdermal permeability and retention for a 1.0% allantoin agent, following selected current treatments.
Figure 9B:
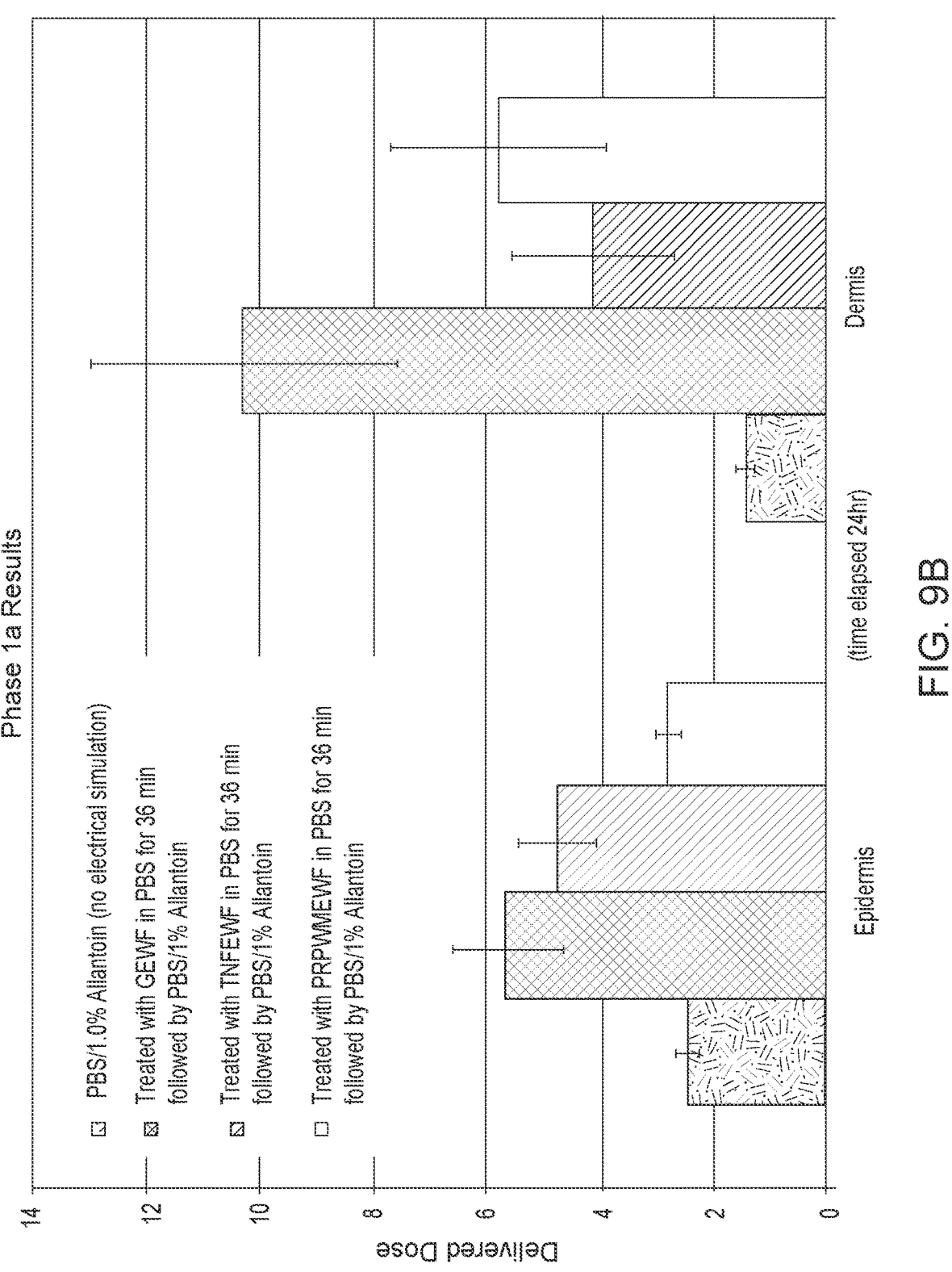

FIG. 9A is a bar chart illustrating transdermal permeability for a 1.0% allantoin agent, following selected current treatments. FIG. 9B is a bar chart illustrating allantoin retention in the epidermis and dermis, following application of the agent.

FIGS. 9A and 9B et seq. use the codes GEWF (galvanic electrical waveform), TNFEWF (CSW electrical waveform), PRPWMEWF (Program Random Pulse Width Modulation electrical waveform), and PBS/1.0% allantoin (phosphate buffered saline containing 1.0% allantoin). As shown in FIG. 9A, at six and twenty-four hours all three waveforms produced levels of allantoin penetration. In this particular example, there was a fivefold increase in transdermal penetration of allantoin with the three selected waveforms: galvanic, CSW and PRPWM, as applied as an electrical waveform in the pretreatment phase. Delivered doses are in arbitrary units, for example μg/cm², or other suitable, appropriate or convenient measure, as known in the art.

In the particular examples of FIGS. 9A and 9B, new body serum (NBS) v1.18 and body shaping gel (BSG) formulations were used, tracking representative marker components from the NBS and BSG agent compositions in Franz cell testing according to FIGS. 7A and 7B. Suitable BSG components for enhanced transmission, adsorption, absorption, permeability, flux and retention in various skin layers include, but are not limited to, *Laminaria digitata* extract, *Chrysanthellum indicum* extract, and *Theobroma cacao* (cocoa) extract (e.g., 0.1% caffeine).

Table 1 illustrates a range of these and other beneficial skin treatment components suitable for enhanced skin permeability following a microcurrent pretreatment, representative of the other topical agents, serums, gels and treatments described herein, as well as similar or related organic and inorganic compounds, proteins, amino acids, genetic material, and genetic markers, as known in the art. Additional testing components, parameters and study design procedures are described in Tables 1-6 and illustrated in FIGS. 7A-7B and 8A-8C, with results in FIGS. 9A-16C.

More specifically, Table 1 illustrates representative NBS v1.18 and BSG formula compositions using standard INCI (International Nomenclature Cosmetic Ingredient) quantifications (EU), including tracking markers from NBS and BSG agents used in the Franz cell experiments. The tracking marker components in these agent formulations are suitable for use in a broad range of Franz cell testing, and include allantoin (in an NBS agent), also known as 5-ureidohydantoin or glyoxyldiureide.

TABLE 1

| Representative Topical Agent Components | |
| --- | --- |
| INCI (EU) | % INCI |
| Aqua | 76.872650 |
| Glycerin | 7.482000 |
| Propanediol | 4.010000 |
| Pentylene glycol | 3.000000 |
| PEG-16 macadamia glycerides | 2.500000 |
| PEG-10 sunflower glycerides | 1.500000 |
| PEG-40 hydrogenated castor oil | 1.000000 |
| Water | 0.950000 |
| Carthamus Tinctorius seed oil | 0.862500 |
| Carbomer | 0.300000 |
| Hydroxyacetophenone | 0.300000 |
| Panthenol | 0.200000 |
| Sodium benzoate | 0.150000 |
| Xanthan gum | 0.150000 |
| *Camellia sinensis* leaf extract | 0.135000 |
| Arginine | 0.120000 |
| Allantoin | 0.100000 |
| Adenosine | 0.060000 |
| Caprylyl glycol | 0.050000 |
| Disodium EDTA | 0.050000 |
| Ethylhexylglycerin | 0.040000 |
| Tocopheryl acetate | 0.040000 |
| *Caesalpinia Spinosa* fruit extract | 0.023750 |
| Kappaphycus Alvarezii extract | 0.023750 |
| Sodium hydroxide | 0.017000 |
| Hydroxypropyl methylcellulose stearoxy ether | 0.010000 |
| Lotus Corniculatus flower extract | 0.010000 |
| Parfum | 0.010000 |
| Phenoxyethanol | 0.010000 |
| Sodium acetylated hyaluronate | 0.010000 |
| Sodium hyaluronate | 0.010000 |
| Benzotriazolyl dodecyl p-cresol | 0.001000 |
| Pentaerythrityl tetra-di-t-butyl hydroxyhydrocinnamate | 0.001000 |
| *Crithmum Maritimum* extract | 0.000500 |
| Tocopherol | 0.000500 |
| S-pea oligopeptide-1 SP | 0.000350 |
| Citric acid | 0.000000 |
| Total | 100.000000 |

Allantoin has been shown to exhibit anti-irritant and anti-oxidant function, and is also known for keratolytic effects (e.g., exfoliation), and used as an active ingredient in skin creams. Caffeine (BSG) is another suitable marker, also known as trimethylxanthine, an anti-oxidant and an anti-inflammatory active understood to stimulate vasodilation and induce fatty acid oxidation Round one testing was performed for three electrical waveforms with allantoin in PBS (phosphate buffered saline) or the NBS agent. The goal was to compare the three electrical waveforms for their capacity to deliver the one or more components in the NBS v1.18 agent. The delivery was tracked via allantoin measurement, used as a skin penetration tracking marker.

The study was conducted in two phases or parts. Round 1a (Round 1: Phase 1a) evaluated the penetration of 1.0% allantoin (an active) in PBS with a galvanic electrical waveform (GEWF), charge-balanced, symmetric electrical waveform (CSW), and a Program Random Pulse Width Modulation electrical waveform (PRPWMEWF), in a Franz cell model. Details of the testing process includes receptor well collection and processing (Table 2A), and the epidermal and dermal retention protocol to assess penetration of the tracking markers (Table 2B).

TABLE 2A

Receptor well collection and processing
Sampling Regimen & Details

| | |
|---|---|
| Receptor well samplings | Six (6); see study design for details |
| Volume to be extracted | 300 μL |
| Extract handling | Load in 96-well microtiter plate; store at 4-8° C. prior to analysis; analyze within 5 days of collection |
| Formulation reapplication | Arm 1: apply formulation after stimulation; see study design for details |

Samples and treatments included 1.0% allantoin in PBS, with no electrical stimulation. The skin sample was also pretreated with a GEWF (Galvanic Electrical waveform) in PBS for thirty-six minutes (36 m), followed by treatment with a PBS topical or agent containing 1.0% allantoin. Pretreatment was also applied with a charge-balanced, symmetric electrical waveform (CSW) in PBS for 36 m, followed by treatment with a PBS agent containing 1.0% allantoin, or treatment with a Program Random Pulse Width Modulation electrical waveform (PRPWMEWF) in PBS for 36 m followed by application of a PBS agent with 1.0% allantoin.

The microcurrent dosage delivered ranged up to 375 microampere (μA) for a twelve minute cycle, repeated for three cycles. Receptor fluid collection was measured at time t=0 (before and immediately after the topical sample treatment), at the end of waveform cycle 1 (t=12 min), at the end of waveform cycle 3 (t=36 m); and at 1 hour (1 h), 6 h and 24 h intervals post-pretreatment with the electrical waveform and treatment with the selected topical agents.

TABLE 2B

Epidermal and dermal retention protocol to assess tracking marker
Retention Sampling Details

| | |
|---|---|
| Procedure at final time point | Wash; tapestrip 3x & discard; separate epidermis & dermis |
| Skin surface wash details | 200 μL water-EtOH 50-50; contact for 5 minutes & remove with kim wipe |
| Skin piece weights: | -N/A- |
| Tapestrip details | -N/A- |
| Epidermis-dermis separation details | 60° C. hot plate for 1 minute (where necessary) |

As shown in FIG. 9B, at twenty-four hours, all three electrical waveforms GEWF, TNFEWF and PRPWMEWF produced allantoin epidermal and dermal retention. In this particular example, the GEWF (galvanic electrical waveform) treatment induced slightly more retention in the skin epidermis and dermis, as compared to the CSW (charge-balanced, symmetrical electrical waveform) and the PRPWMEWF (Program Random Pulse Width Modulation electrical waveform).

Figure 10A:
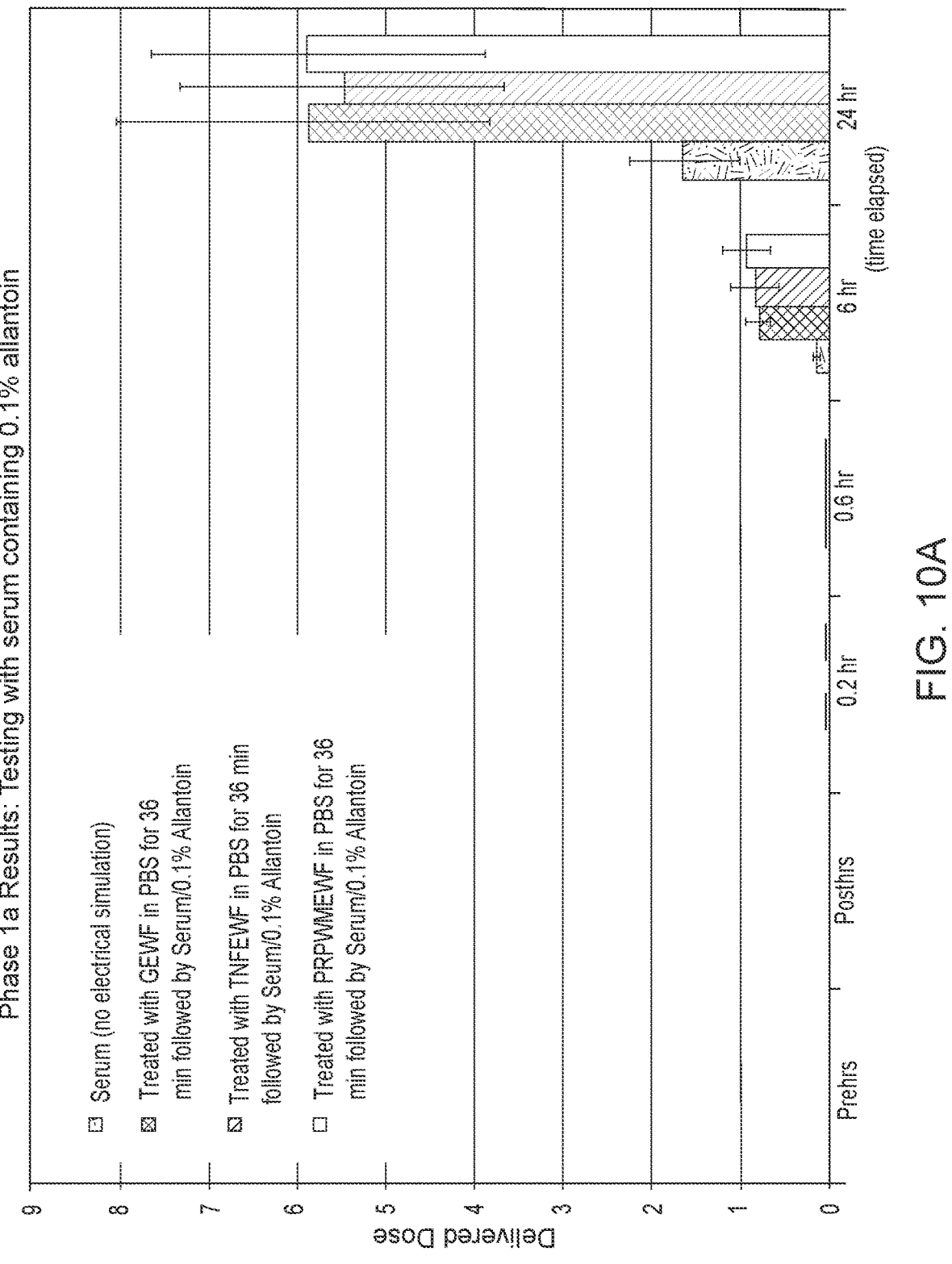
FIGS. 10A and 10B are bar charts illustrating transdermal permeability and retention for a 0.1% allantoin serum, following selected current treatments.
Figure 10B:
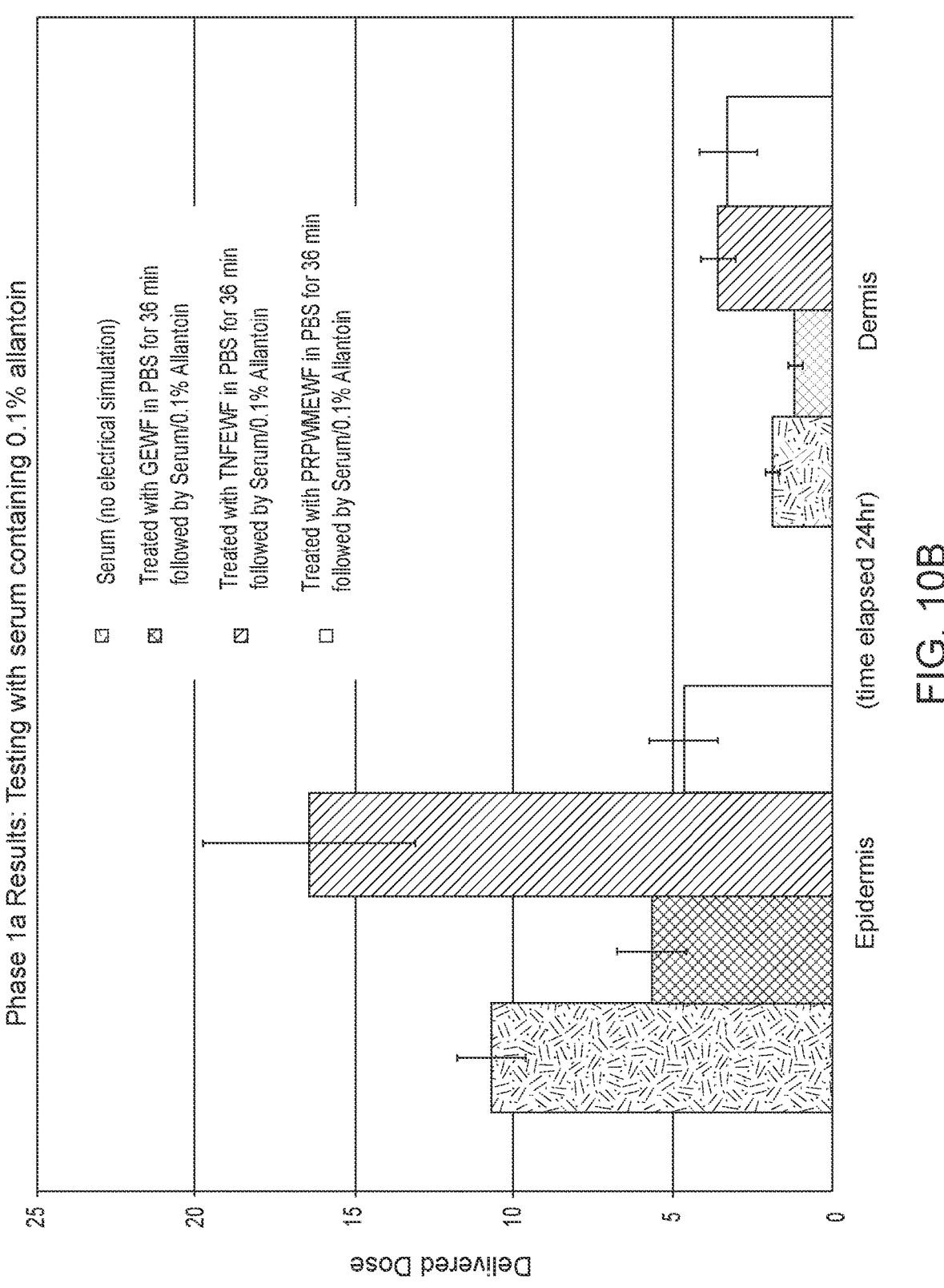

FIG. 10A is a bar chart illustrating transdermal permeability for a 0.1% allantoin serum, following the selected treatments (e.g., New Body Serum v1.18, available from Nu Skin Enterprises, Inc., of Provo, Utah). FIG. 10B is a bar chart illustrating allantoin retention in the epidermis and dermis, following application of the serum.

Round 1b (Round 1: Phase 1b) testing included evaluation of the NBS v1.18 agent with the GEWF (galvanic electrical waveform), CSW (charge-balanced, symmetric electrical waveform) and PRPWMEWF (Program Random Pulse Width Modulation electrical waveform), in a Franz cell model as described herein. Samples and treatments included the NBS v1.18 agent containing 0.1% allantoin, with no electrical stimulation.

The skin was also pretreated with the GEWF (galvanic electrical waveform) in PBS for thirty-six minutes, followed by treatment with NSB v1.18 agent containing 0.1% allantoin, the CSW (charge-balanced, symmetric electrical waveform) in PBS for 36 m followed by treatment with the NBS v1.18 agent containing 0.1% allantoin, and with the PRPWMEWF (Program Random Pulse Width Modulation electrical waveform) in PBS for 36 m followed by treatment with the NBS v1.18 agent containing 0.1% allantoin.

The microcurrent dosage ranged up top 375 μA per cycle (12 m), over three cycles (36 m). Receptor fluid collection was performed at time t=0 (before and immediately after topical sample treatment), at the end of waveform cycle one (12 m), at the end of waveform cycle three (36 m), and at 1 h, 6 h and 24 h intervals post pre-treatment with the electrical waveform, and treatment with the topical agent.

As shown in FIG. 10A, at 6 h and 24 h, all three waveforms produced a similar level of transdermal penetration of the NBS v1.18 agent. There was fivefold increase in transdermal penetration of the NBS v1.18 agent with the three waveforms, GEWF, TNFEWF and PRPWMEWF at 24 h post electrical pre-treatment, when compared to the NBS v1.18 agent where the skin was not stimulated with the microcurrent electrical pretreatment.

As shown in FIG. 10B, at 24 hours, the charge-balanced, symmetric electrical waveform (TNFEWF) produced higher NBS v1.18 agent epidermal and dermal retention, as compared to the GS and PRPWM waveform electrical pretreatments.

Round Two Testing

Round Two "Tioga" studies were also performed in two parts or phases. The Round 2a (Round 2: Phase 2a) treatment methodology included evaluation of the TNFEWF (CSW) electrical waveform) to stimulate delivery of PBS and the NBS v1.18 agent. Table 3 summarizes the electrical pretreatment (Ept), including PBS (Phosphate Buffer Saline) samples used as a dose agent for Ept-36E (electrical pretreatment with 36 m of microcurrent waveform application).

Figure 11A:
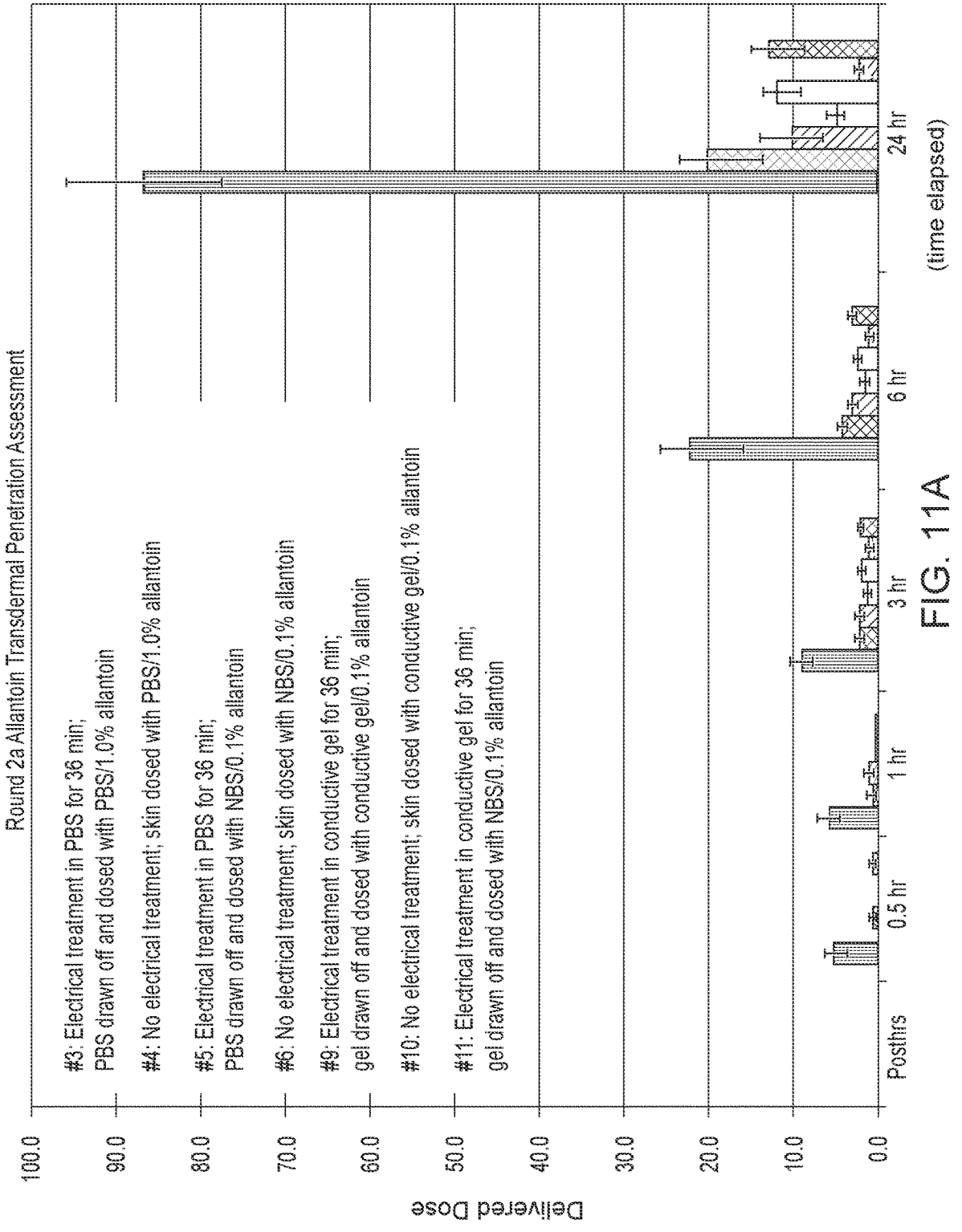
FIGS. 11A, 11B and 11C are bar charts illustrating transdermal allantoin penetration, retention and flux, following selected current treatments.
Figure 11B:
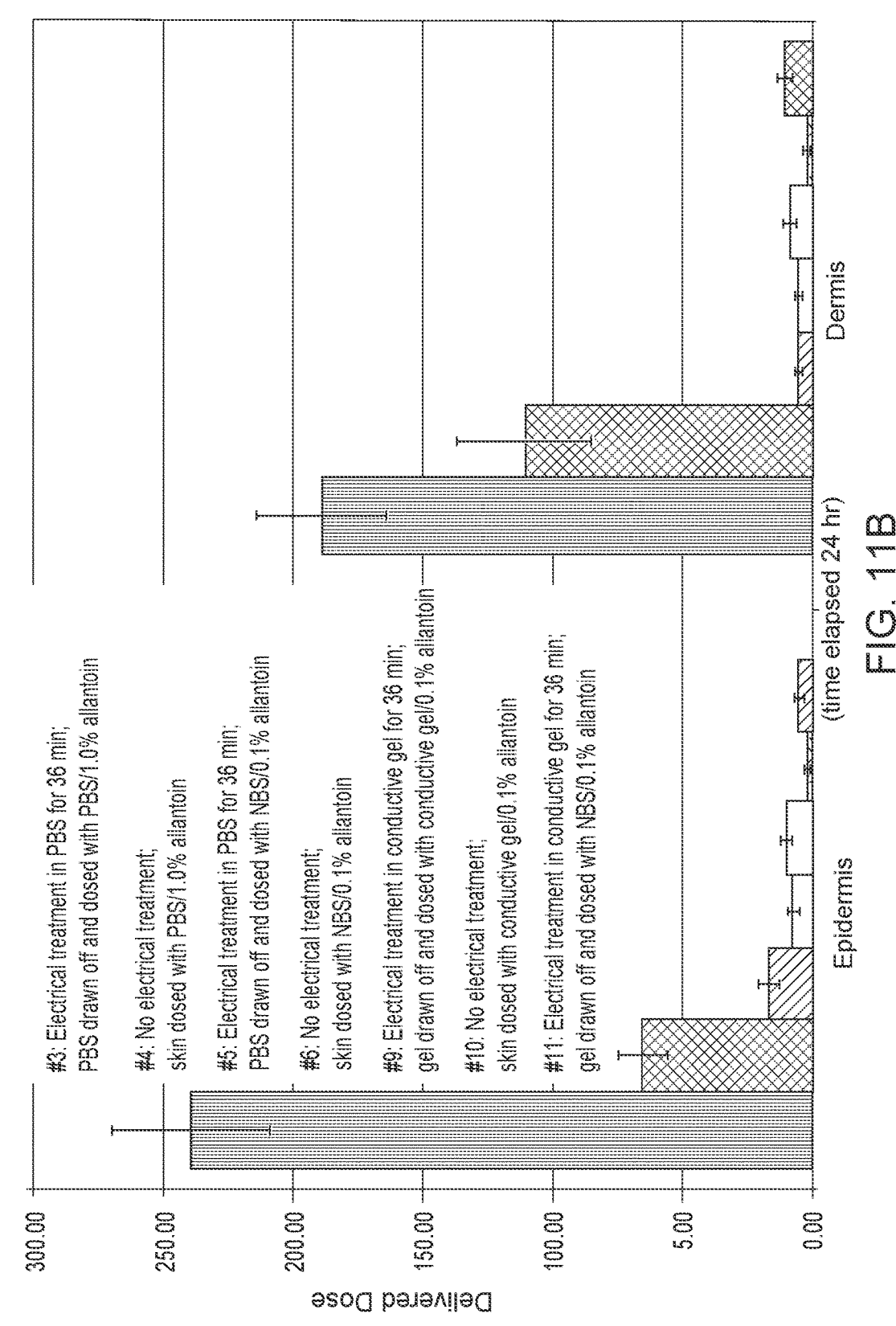
Figure 11C:
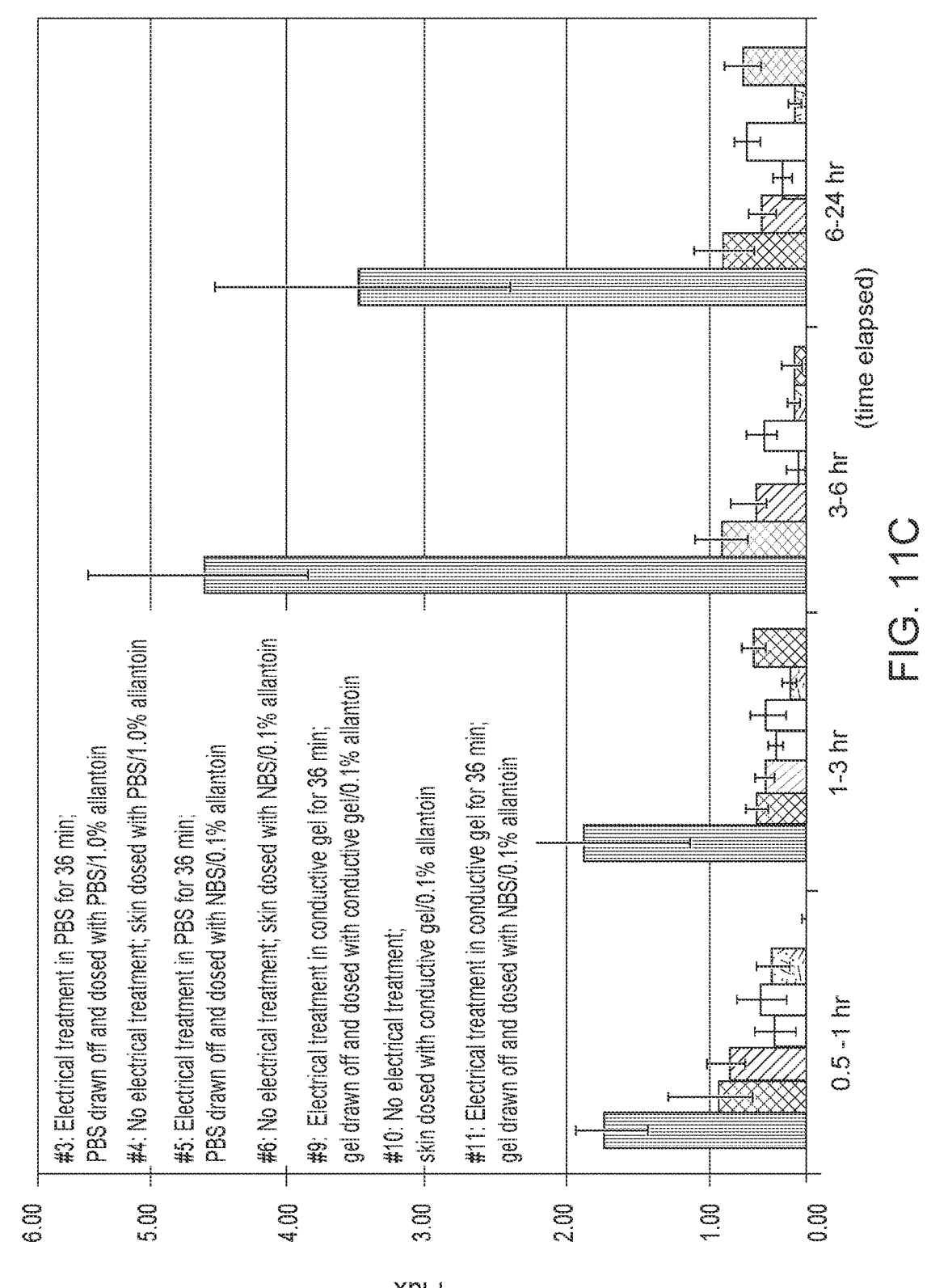

FIG. 11A is a bar chart illustrating transdermal allantoin penetration, following selected current treatments. FIG. 11B is a bar chart illustrating allantoin retention in the epidermis and dermis, following the selected treatments. FIG. 11C is a bar chart illustrating allantoin flux, following the selected treatments. The Flus is in arbitrary units, for example μg/cm²/hr, or other suitable, appropriate or convenient measure, as known in the art.

The data in FIGS. 11A and 11B were produced by testing delivered dosages through skin samples under a number of different conditions (e.g., in the arm region), ordered #3, #4, #5, #6, #9, #10 and #11 from left to right in the histogram plots (test # or "Arm #"). As shown in FIG. 11A, the test #3 and test #4 data (see legend for conditions) are consistent with data from Round 1 for the same experimental treatment design. Greater than fivefold (>5×) increase in penetration of allantoin was seen after electrical pre-treatment using PBS, as compared to a non-electrical pretreated skin sample with PBS.

TABLE 3

| Arms | All TN Electrical | Waveform | Sample drawn off | Doused with | Assayed for |
|------|-------------------|----------|------------------|-------------|-------------|
| | | Electrical pretreatment (Ept) | | | |
| 1 | PBS | Ept-36 min | PBS | PBS containing 1.0% caffeine | Caffeine |
| 2 | PBS w/1.0% caffeine | No electric treatment | | | Caffeine |
| 3 | PBS | Ept-36 min | PBS | PBS containing 1.0% allantoin | Allantoin |
| 4 | PBS w/1.0% allantoin | No electric treatment | | | Allantoin |
| 5 | PBS | Ept-36 min | PBS | NBS v1.18 containing 0.1% allantoin | Allantoin |
| 6 | NBS v1.18 | No electric treatment | | | Allantoin |
| 7 | Conductive gel | Ept-36 min | Conductive gel | Conductive gel containing 1.0% caffeine | Caffeine |
| 8 | Conductive gel w/1.0% caffeine | No electric treatment | | | Caffeine |
| 9 | Conductive gel | Ept-36 min | Conductive gel | Conductive gel containing 1.0% allantoin | Allantoin |
| 10 | Conductive gel w/1.0% allantoin | No electric treatment | | | Allantoin |
| 11 | Conductive gel | Ept-36 min | Conductive gel | NBS v1.18 containing 0.1% allantoin | Allantoin |
| 12 | Conductive gel | Ept-36min | Conductive gel | Body Shaping Gel containing 0.1% caffeine | Caffeine |

Test #5 and test #6 data showed >5× skin delivery of the NBS agent containing 0.1% allantoin, after electrical pretreatment using PBS as compared to the non-electrical waveform pretreatment sample, with an NBS agent containing 0.1% allantoin. Test #9 and test #11 data showed >5× delivery of allantoin after electrical pre-treatment using a conductive gel containing 1.0% allantoin, as compared to a non-electrical waveform pretreatment sample with conductive gel containing 1.0% allantoin (test #10). Note that the test #5, #6, #9, #10 and #11 data have lower doses of allantoin.

As shown in FIG. 11B, the test #3 and test #4 data are consistent with data from Round 1 for the same treatment design. Greater than fivefold increase in penetration of allantoin was seen upon electrical pre-treatment in both the epidermis and dermis, as compared to a non-electrically stimulated sample with PBS. Test #5 showed greater than two-fold (>2×) skin delivery of the NBS agent containing 0.1% allantoin in an electrically pretreated epidermis sample, as compared to a non-electrically stimulated NBS sample containing 0.1% allantoin (test #6). There was not necessarily a substantial difference in allantoin retention in the dermis.

The test #9 and test #11 data showed >5× skin allantoin delivery for an electrically treated conductive gel, as compared to a non-electrically stimulated sample with conductive gel (test #10), in the epidermis and dermis. Note that the overall skin penetration may be lower with the NBS agent, since the allantoin concentration is 0.1% in these samples.

As shown in FIG. 11C, the test #3 and test #4 data are consistent with data from Round 1 for the same treatment design. Greater than fivefold increase in penetration of allantoin was seen upon electrical pre-treatment in both the epidermis and dermis, as compared to a non-electrical pretreated sample with PBS.

Test #5 showed greater than twofold increased skin delivery of the NBS agent containing 0.1% allantoin in an electrically treated epidermis sample, as compared to a non-electrically stimulated sample with the NBS agent containing 0.1% allantoin (test #6). There was not necessarily a substantial difference in allantoin retention in the dermis.

The test #9 and test #11 data showed >5× increase in skin allantoin delivery in the electrical pre-treatment sample with a conductive gel agent, as compared to a non-electrically stimulated sample with conductive gel containing 0.1% allantoin (test #10) in the epidermis and dermis.

Note that the overall skin penetration may be lower, since the allantoin concentration is 0.1% in these samples. The overall skin penetration may also be lower with the NBS sample since the allantoin concentration is 0.1% in these samples.

Figure 12A:
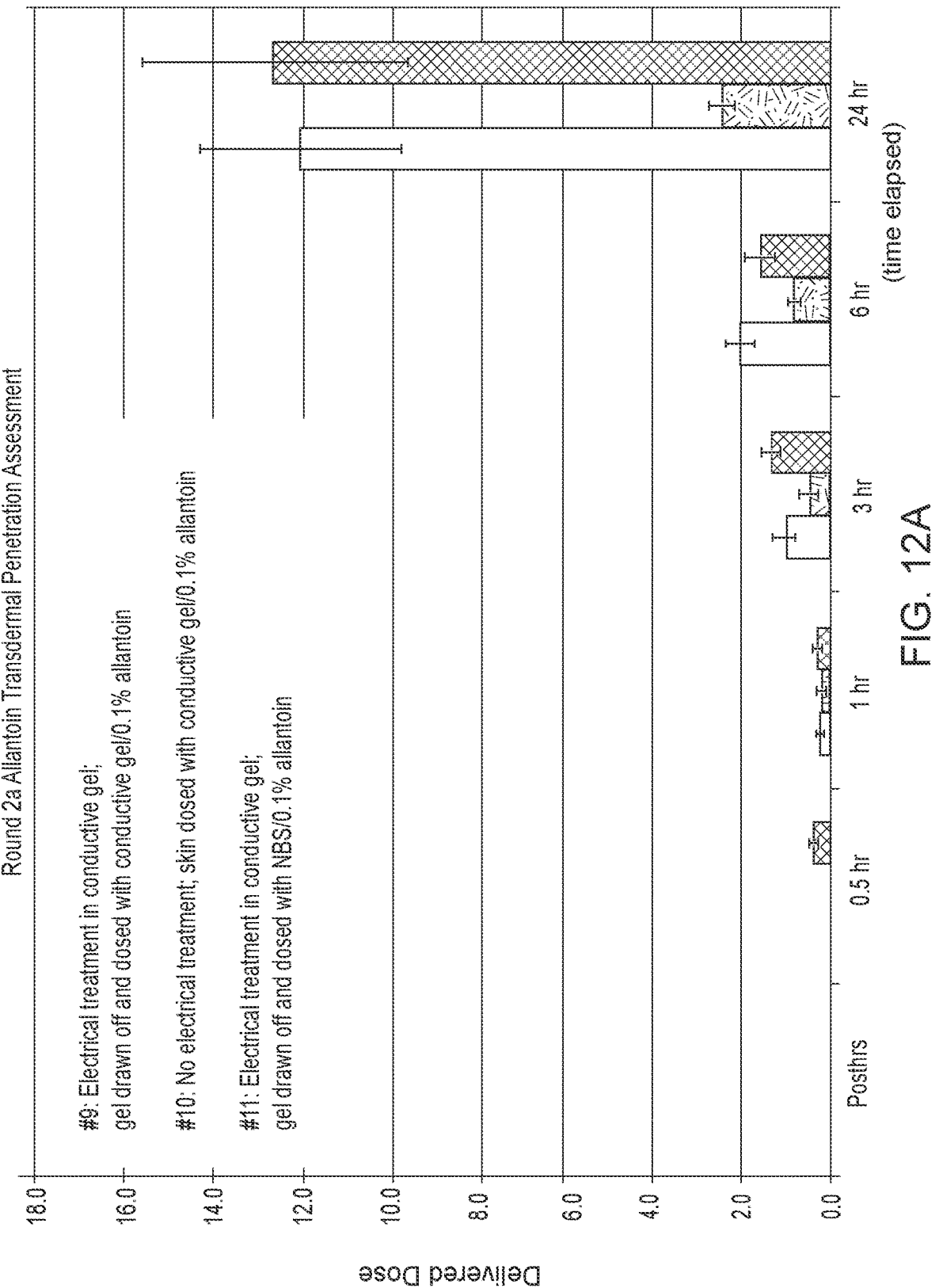
FIGS. 12A, 12B and 12C are bar charts illustrating transdermal allantoin penetration, retention and flux, following alternate current treatments.
Figure 12B:
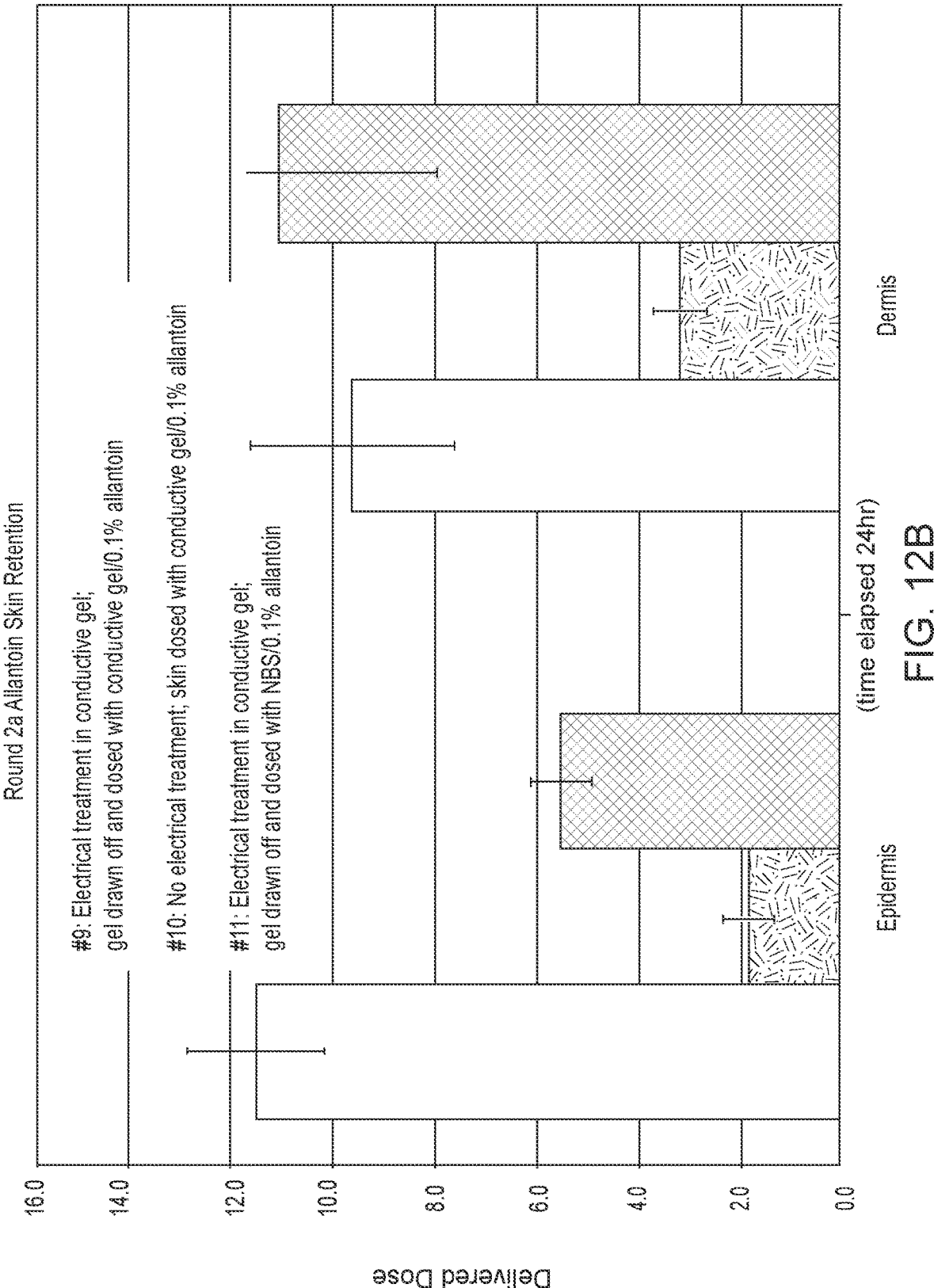
Figure 12C:
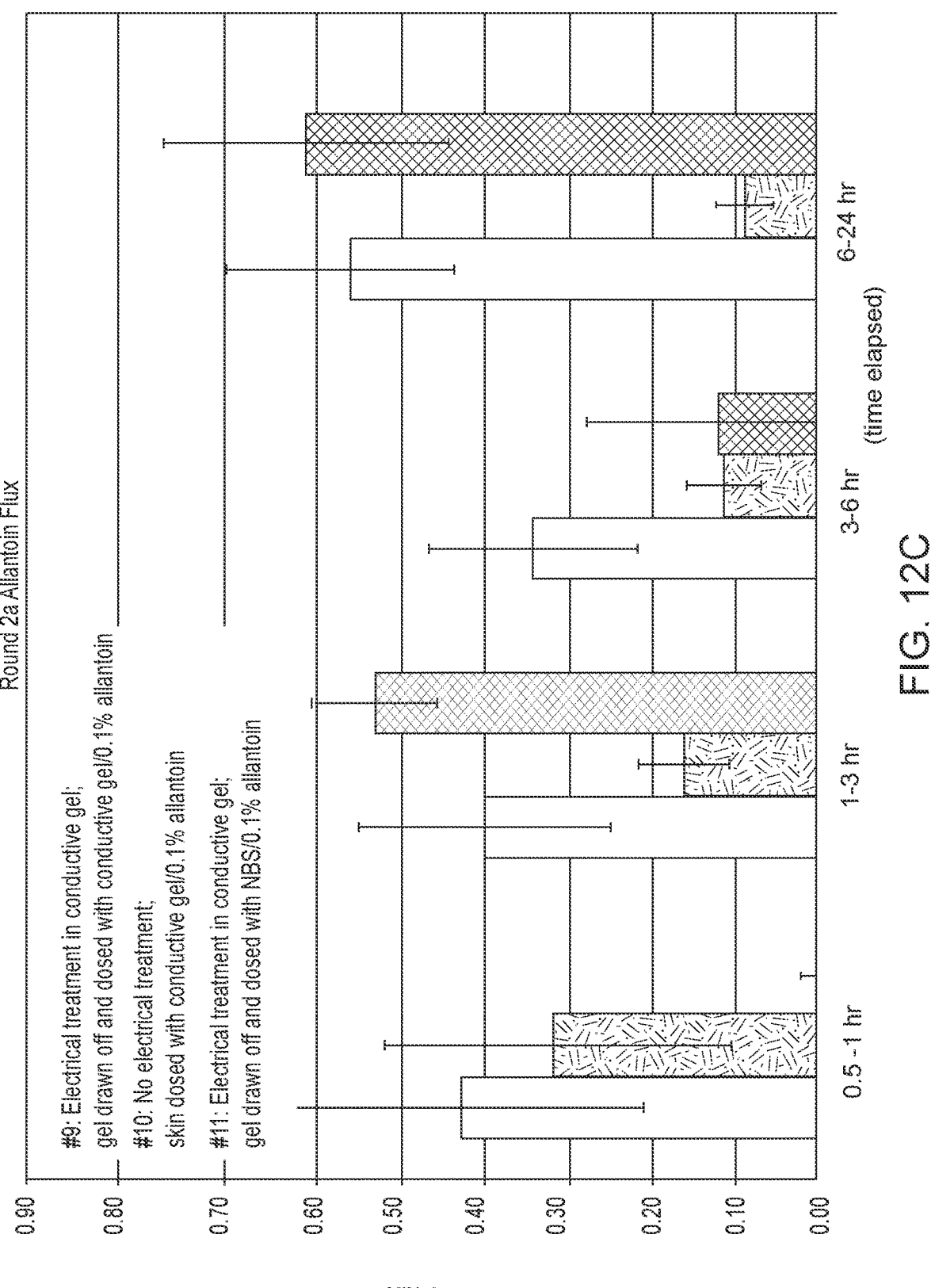

FIG. 12A is a bar chart illustrating transdermal allantoin penetration, following alternate current treatments. FIG. 12B is a bar chart illustrating allantoin retention in the epidermis and dermis, following the alternate treatments. FIG. 12C is a bar chart illustrating allantoin flux, following the alternate treatments.

FIG. 12A illustrates a TNEWF (CSW) waveform electrical pretreatment using an electrified Franz cell for stimulated delivery and transdermal penetration of conductive gel and NBS agent at 24 h following electrical pretreatment. The TNEWF (CSW) waveform pretreatment induced a fivefold increase in transdermal penetration with the conductive gel and NBS agent compared to the non-pulsed control sample (no pretreatment), at 24 h. The conductive gel data allows for the same efficacy of delivery of allantoin from the conductive gel or NBS serum.

FIG. 12B illustrates a TNEWF (CSW) electrical pre-treatment waveform using an electrified Franz cell for stimulated delivery, with a significant increase in retention of the conductive gel and NBS agent in the epidermis and dermis at 24 h following treatment. Allantoin in the conductive gel may be retained more in the epidermis as compared to allantoin in the NBS agent, whereas there was not necessarily a substantial difference in retention of the conductive gel and NBS treatment material in the dermis.

FIG. 12C illustrates a TNEWF (CSW) waveform electrical pretreatment using an electrified Franz cell for stimulated delivery, with a significant increase in conductive gel and NBS agent flux as assessed by allantoin accumulation at 0.5 h to 24 h.

Figure 13B:
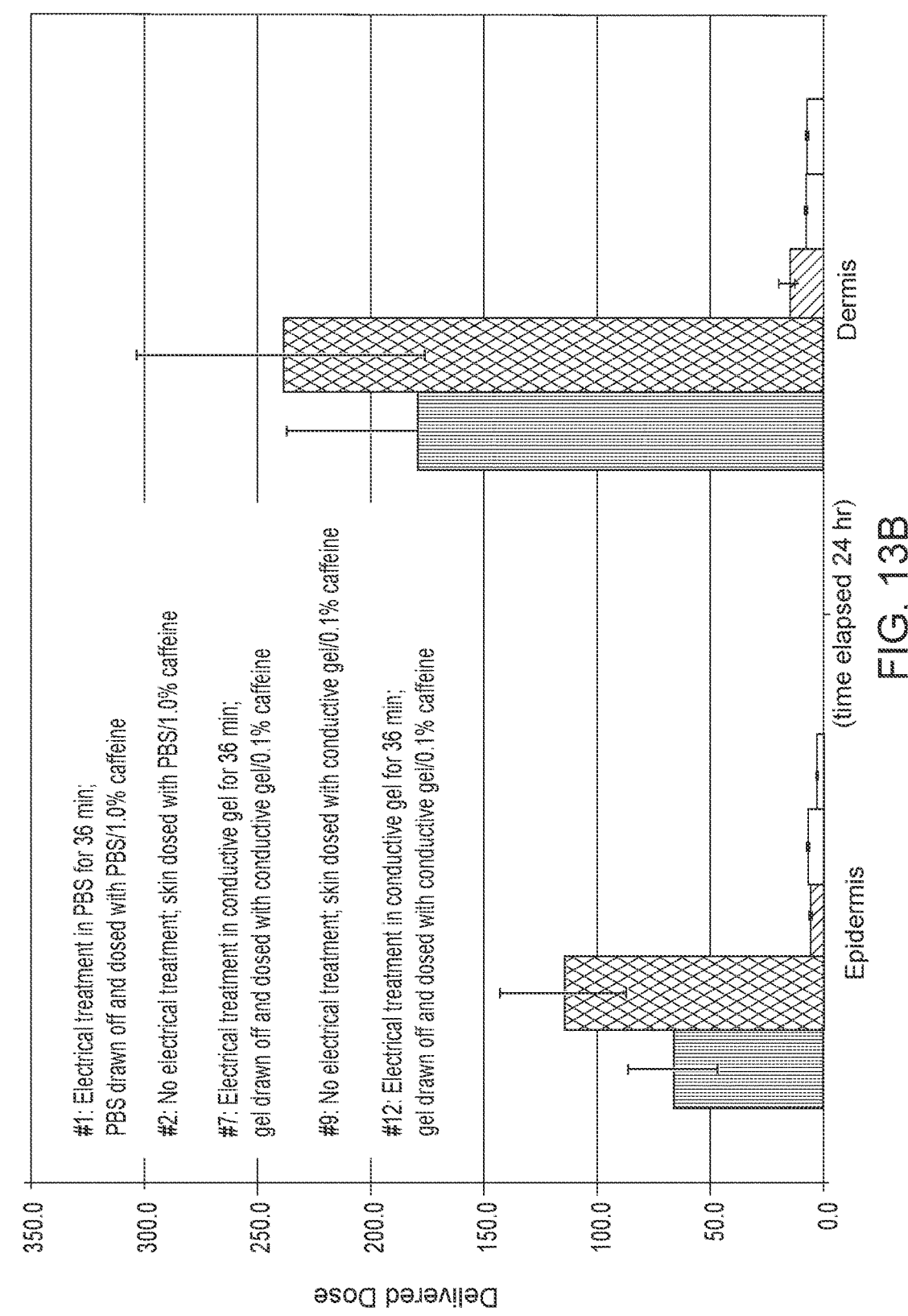
Figure 13C:
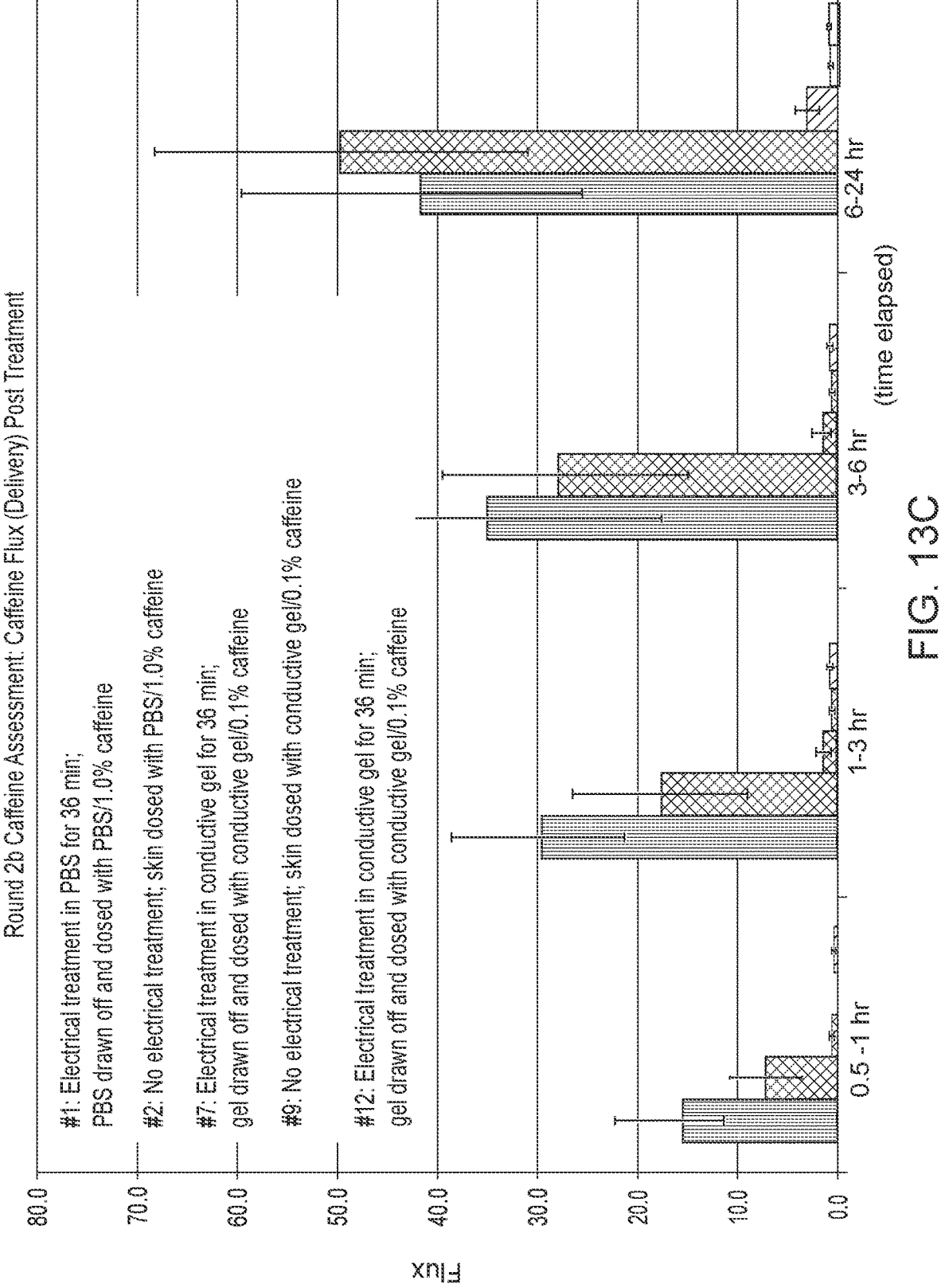

Round 2b (Round 2: Phase 2b) included a caffeine assessment. FIG. 13A is a bar chart illustrating transdermal caffeine penetration, following selected current treatments. FIG. 13B is a bar chart illustrating caffeine retention in the epidermis and dermis, following the selected treatments. FIG. 13C is a bar chart illustrating caffeine flux, following the selected treatments.

As shown in FIG. 13A, the test #1 and test #2 data are consistent with data from Round One for the same experimental treatment design. A greater than fivefold increase in penetration of allantoin was seen after electrical pre-treatment using PBS, as compared to a non-electrical waveform pretreatment sample with PBS using caffeine as a tracking marker. The test #7 showed data show a >5× increase in skin delivery of a conductive gel containing 0.1% allantoin after electrical pre-treatment, as compared to a non-electrical waveform pretreatment sample (test #8) with conductive gel containing 0.1% allantoin. Note that Arms 7, 8 and 12 have lower doses of allantoin.

As shown in FIG. 13B, the test #1 and test #2 data are consistent with data from Round One for the same treatment design. A greater than fivefold increase in penetration of allantoin was seen upon electrical pre-treatment in both the epidermis and dermis, as compared to a non-electrically stimulated sample with PBS. Test #7 showed slightly higher skin delivery for an electrically pre-treated sample with conductive gel containing 0.1% caffeine in the dermis, as compared to test #8, for a non-electrically treated sample with conductive gel containing 0.1% caffeine. There was not necessarily as substantial difference in caffeine retention in the epidermis and dermis between test #8, for a non-electrically pretreated sample with conductive gel containing 0.1% caffeine and test #12, for an electrical pretreatment with a conductive gel followed by a BSG agent containing 0.1% caffeine. Note that the overall skin penetration may be lower with the conductive gel and BSG agent since the caffeine concentration is 0.1% in these samples.

As shown in FIG. 13C, the test #1 and test #2 data are consistent with data from Round One for the same treatment design. A greater than fivefold increase in penetration of allantoin was seen upon electrical pre-treatment in both the epidermis and dermis, as compared to a non-electrical waveform pretreatment sample with PBS.

Test #7 showed >2× caffeine flux for conductive gel containing 0.1% caffeine in an electrically treated epidermis, as compared to a non-electrically stimulated sample with conductive gel containing 0.1% caffeine (test #8). There was not necessarily as substantial difference in caffeine flux between test #8, for a non-electrically pretreated sample with conductive gel containing 0.1% caffeine and test #12, for an electrical pre-treatment with conductive gel followed by a BSG agent containing 0.1% caffeine. Note that the overall caffeine flux may be lower with the conductive gel and NBS agent since the caffeine concentration is 0.1% in these samples.

Figure 14A:
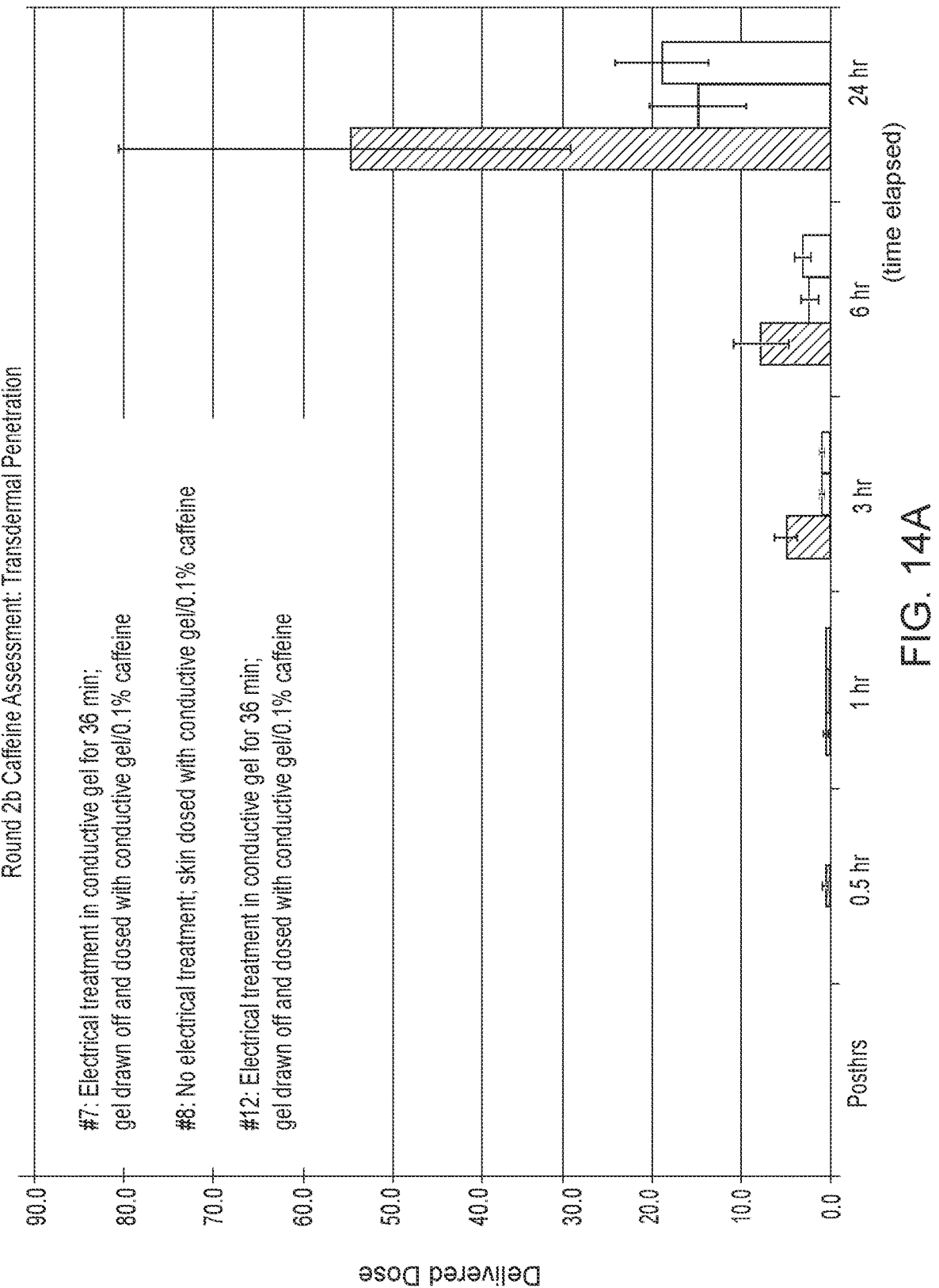
FIGS. 14A, 14B and 14C are bar charts illustrating transdermal caffeine penetration, retention and flux, following alternate current treatments.
Figure 14B:
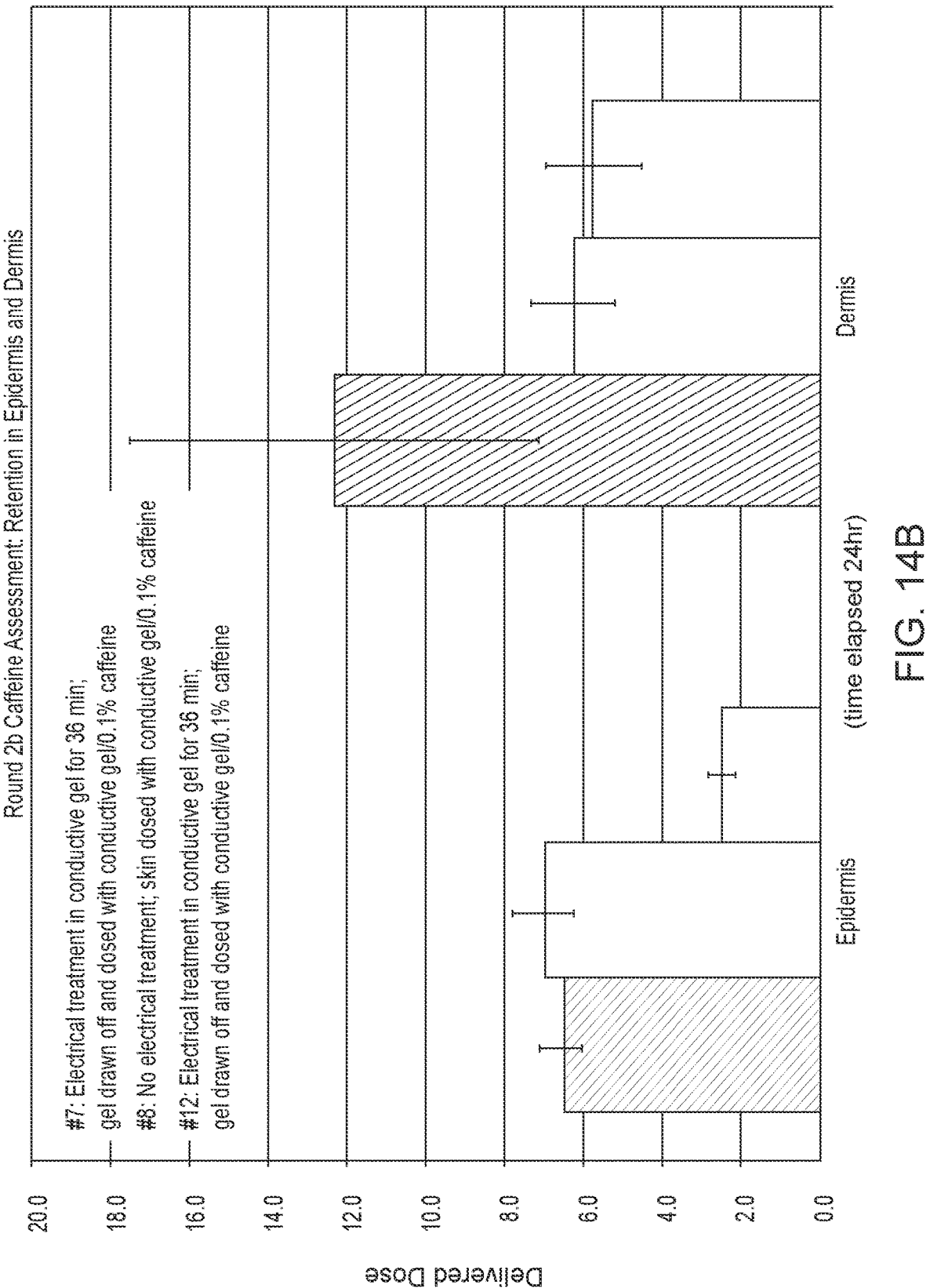
Figure 14C:
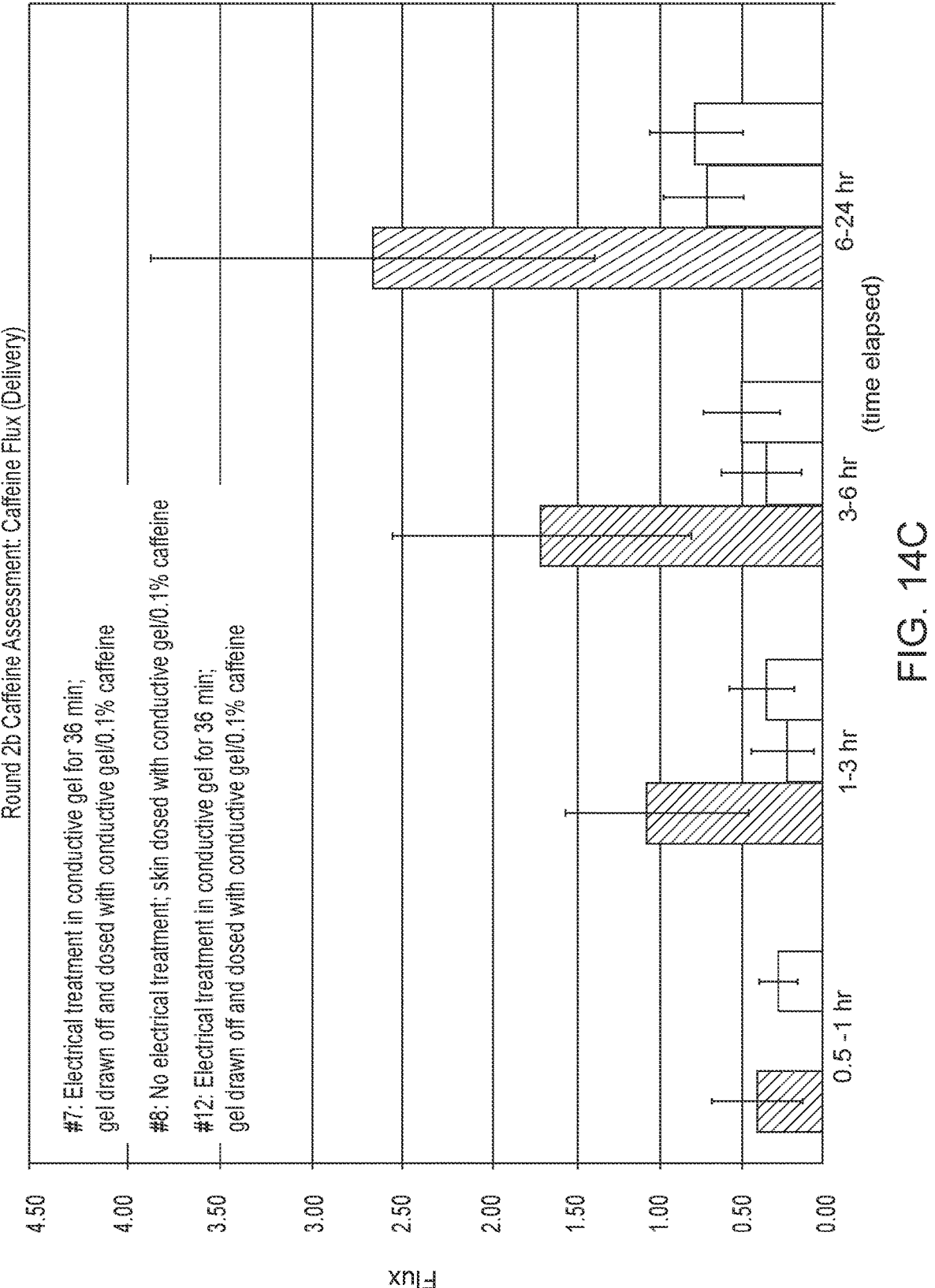

FIG. 14A is a bar chart illustrating transdermal caffeine penetration, following alternate current treatments. FIG. 14B is a bar chart illustrating caffeine retention in the epidermis and dermis, following the alternate treatments. FIG. 14C is a bar chart illustrating caffeine flux, following the alternate treatments.

FIG. 14A shows that a TNEWF (CSW) waveform pretreatment in an electrified Franz cell stimulated delivery with a fivefold increase in transdermal penetration of a conductive gel at 24 h, as compared to a BSG agent and a non-electrically treated control sample following such a treatment, assessed using caffeine as a tracking marker. There was minimal stimulation of BSG agent penetration when pre-treated with the TNEWF (CSW) waveform.

FIG. 14B illustrates a TNEWF (CSW) waveform pretreatment in an electrified Franz cell stimulated a significant increase in retention of conductive gel in the dermis at 24 h following treatment. There was not necessarily as substantial difference between an electrically pretreated and non-electrically pretreated sample for conductive gel retention in the dermis. The retention for an electrically treated sample with conductive gel was twofold less in the epidermis and similar in the dermis, as compared to a sample with no electrical waveform pretreatment and a conductive gel.

FIG. 14C shows that a TNEWF (CSW) waveform in an electrified Franz cell stimulated a significant increase in retention of conductive gel in the dermis at 24 h following treatment. There was not necessarily a substantial difference between an electrically pretreated and a non-electrically treated sample for conductive gel retention in the dermis. The retention for an electrically pretreated sample with conductive gel was twofold less in the epidermis and similar in the dermis, as compared to a sample with no electrical waveform pretreatment and conductive gel.

TABLE 4

Electrical characteristics of studied topical agents: pH and conductivity

| | TN Gel | Conductive Gel | Body Shaping Gel | NBS Shaping Gel 1.18 |
|---|---|---|---|---|
| pH at RT | 6.6 | 5.87 | 5.53 | 5.4 |
| Conductivity RT | 3150 μS | 1075 μS | 247 μS | 836 μS |
| Conductivity 37C | 4030 μS | 1434 μS | 308 μS | 1103 μS |
| Conductivity 42C | 4420 μS | 1618 μS | 355 μS | 1227 μS |

Table 4 illustrates electrical characteristics of representative studied topical agents, including pH and conductivity of topical agents used in the "Tioga" study. Conductivity is given in microsiemerts/cm (μS/cm or simply "μS"). The topical agents may have different pH and different conductivity but can perform equally well or substantially similarly in their capacity to penetrate skin, when pre-treated with selected electrical waveforms as described herein.

Conclusions from the Round One and Round Two testing include the following:

PBS followed by electrical pretreatment and dosing with PBS containing allantoin/caffeine is consistent with data from Round One for the same treatment design. A greater than fivefold increase in penetration of allantoin/caffeine was seen upon a pulsed microcurrent pretreatment, as compared to non-pulsed-microcurrent sample treated with PBS.

The TNEWF (CSW) waveform electrified (pulsed) Franz cell test induced increased delivery and penetration of conductive gel and NBS agent as assessed by the allantoin marker.

The TNEWF (CSW) electrical waveform Franz cell testing also induced twofold increased delivery and penetration of conductive gel, compared to the BSG agent as assessed by the caffeine marker.

The BSG agent penetrated better for an electrically pre-
treated sample than for a non-electrically pretreated
treated topical control sample.

Electrified topical agents (agent applied in a Franz cell
with electrical waveform pretreatment) were in general
delivered up to fivefold more effectively as compared
to non-electrified topical agents (topical agents applied
in a Franz cell without electrical waveform pretreat-
ment).

The data suggest that electrification pretreatment causes
changes to the skin properties resulting in substantially
or significantly increased penetration of post-applied
topical agents in the skin, as compared to topical
application alone, without pretreatment.

Round Three Testing

Round Three testing included a 1.0 wt % allantoin assess-
ment in PBS with a TNFEWF (CSW) electrical waveform.
Pretreatment with CSW electrical waveforms included vary-
ing the current (e.g., up to 375 µA, up to 250 µA, or up to
125 µA), varying the pretreatment time periods (e.g., up to
3 m, or up to 6 m), with allantoin 1.0 wt % in PBS.

Table 5 summarize the Round Three treatment method-
ology and experimental design. The number of Franz cell
replicates (Franz cells) per sample was n=3 for non-electri-
cal pretreated samples, and n=6 for pulsed electrical pre-
treatment samples. The number of Franz cell replicates may
also vary. The current flow (I) is given in microamperes
(µA), and the pulse time (PT) in minutes (mi) where zeros
indicate no electrical current, and no pulse time. In each
case, the next include the sample being drawn off (draw off),
and post pulse treatment/dosing with phosphate buffered
saline (PBS) containing 1.0% allantoin. Assessment times
were at post 0.5, 1.0, 6 and 24 hours (hr), assaying for
allantoin.

levels. FIG. 15B is a bar chart illustrating allantoin retention
in the epidermis and dermis for the treatment durations and
current levels. FIG. 15C is a bar chart illustrating allantoin
flux for the treatment durations and current levels.

The treatments were performed by administering the
waveform for three and six minute periods at microcurrent
levels of 375 µA, 250 µA, and 125 µA, respectively ordered
from (i) to (vi) in the drawings. The corresponding histo-
grams are arranged from left to right for each time interval.

Figure 15A:
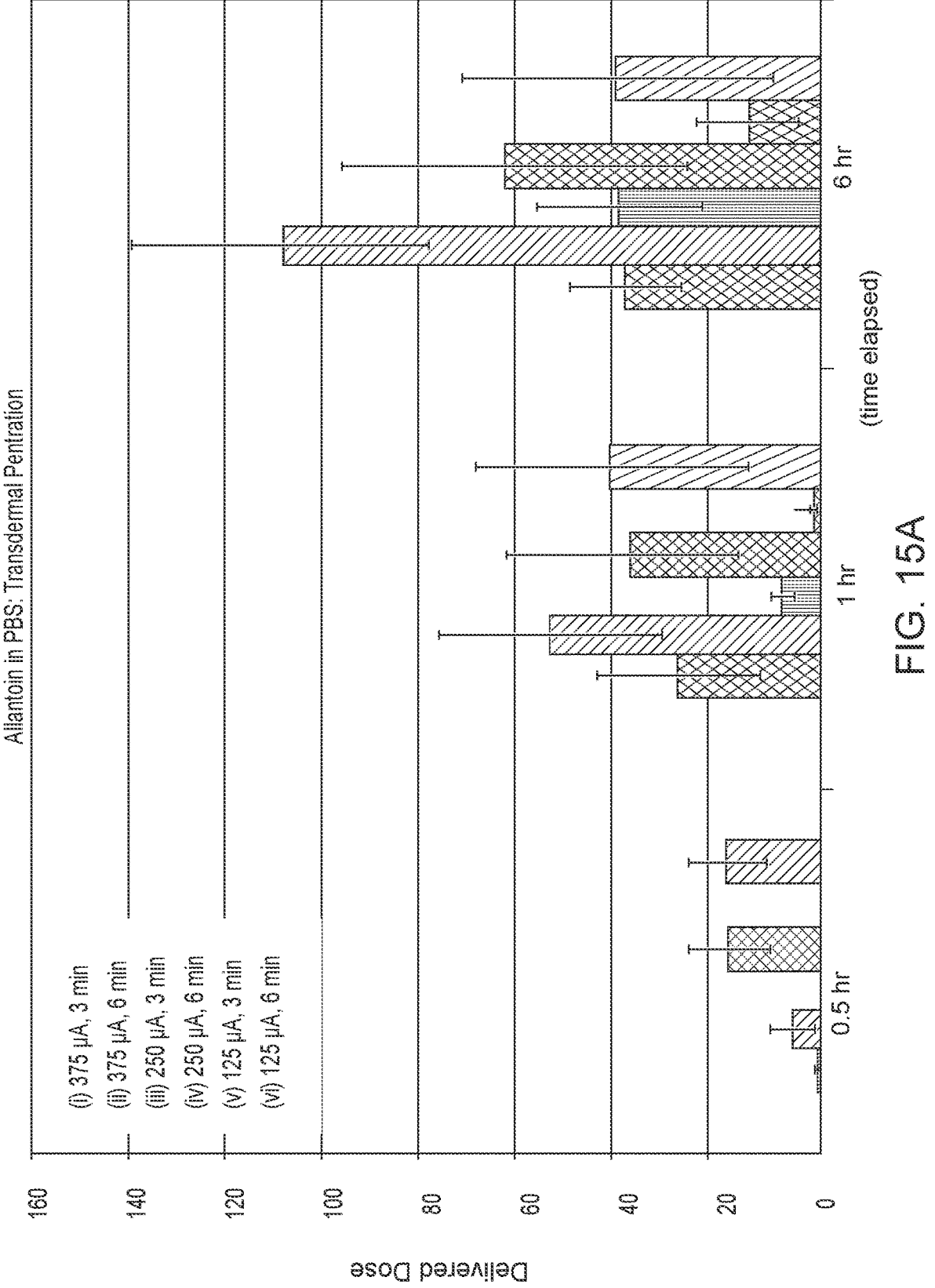
FIGS. 15A, 15B and 15C are bar charts illustrating transdermal allantoin penetration, retention and flux for selected three and six minute current treatment durations.
Figure 15B:
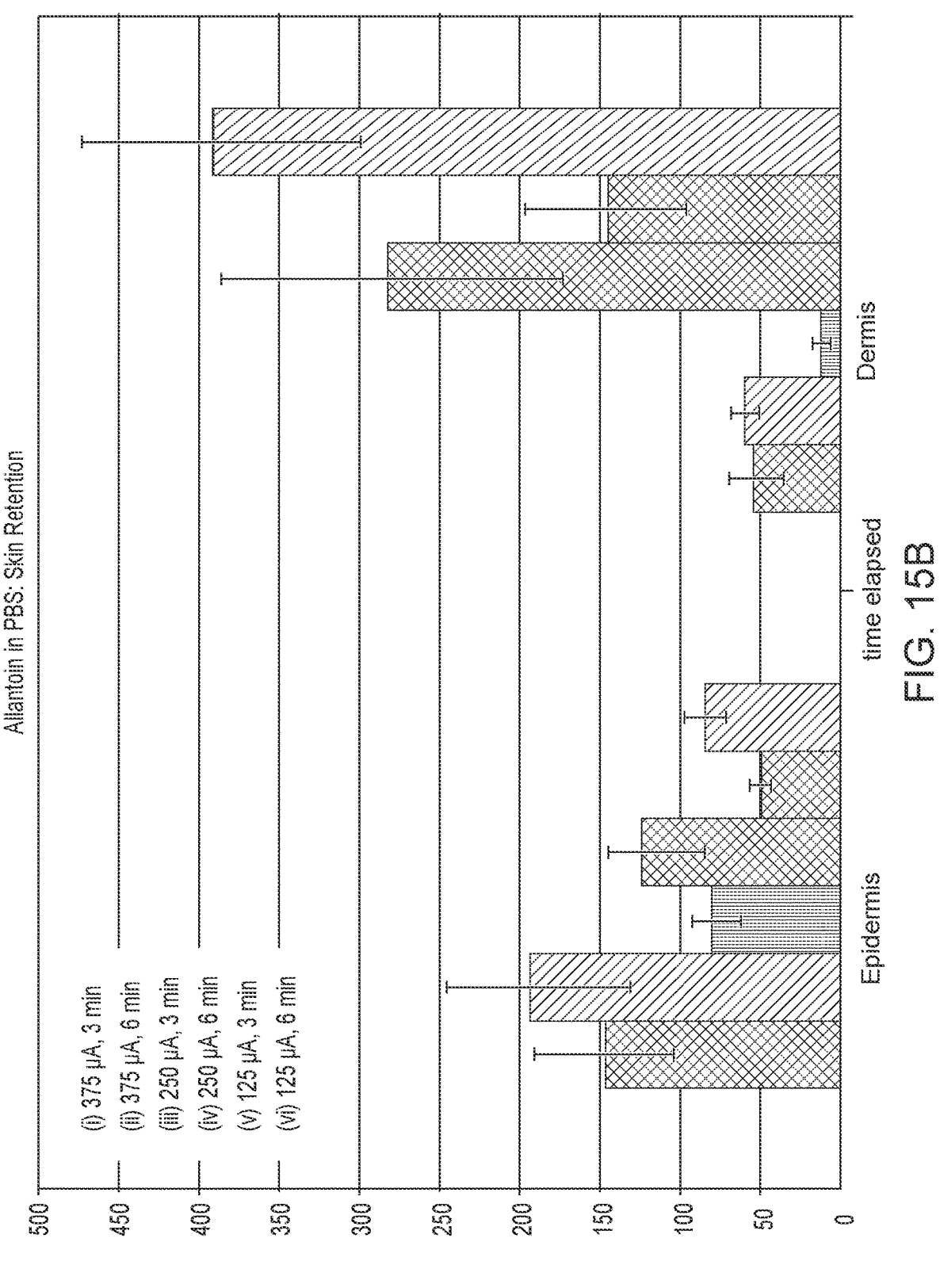
Figure 15C:
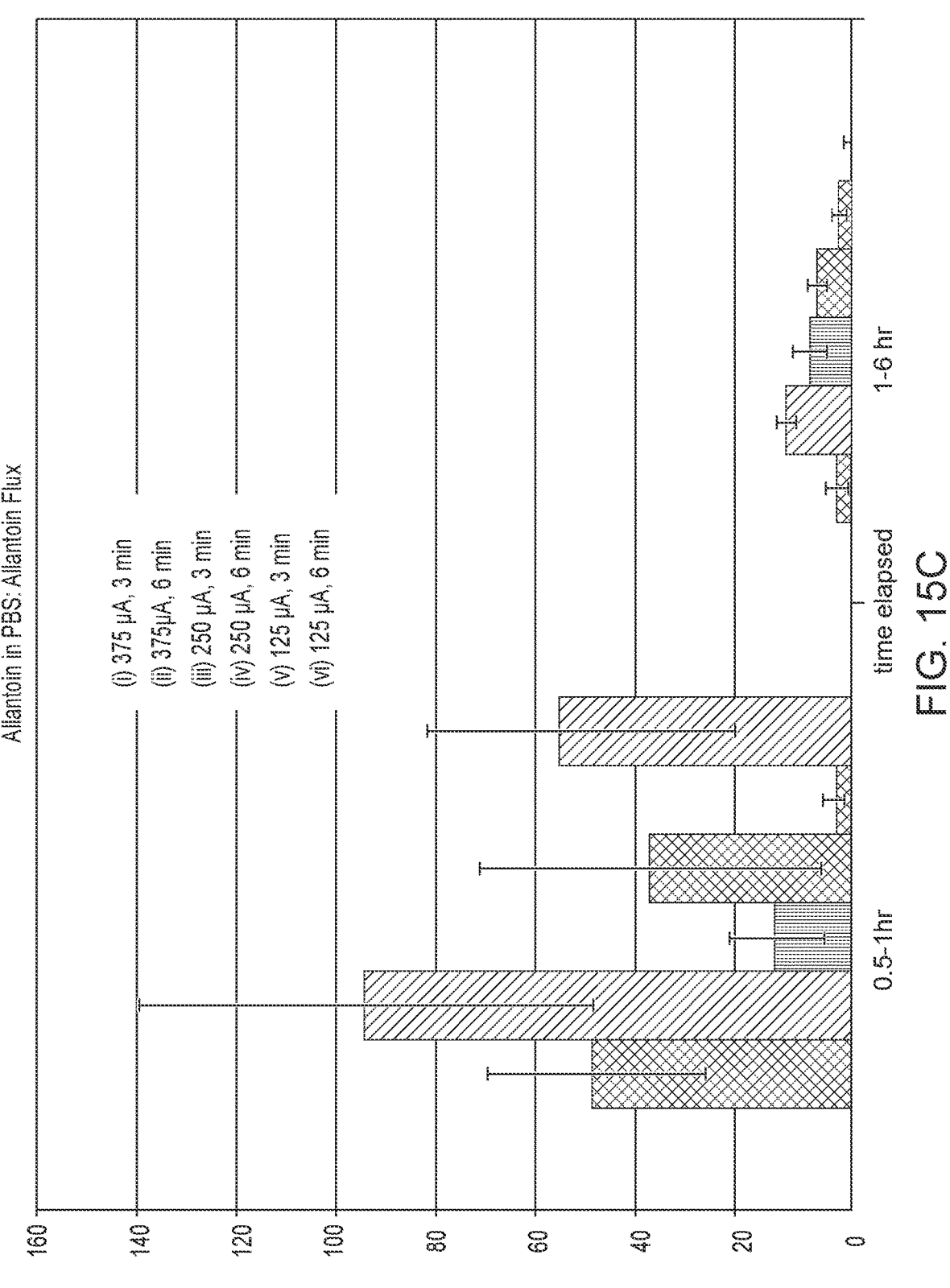

As shown in FIG. 15A, at all current levels there is
increased transdermal penetration of allantoin at six minutes
as compared to a three minute pretreatment. Generally,
higher current levels (e.g., up to 375 µA or more) an
higher/longer pretreatment times (up to six minutes or more)
tend to stimulate greater penetration than lower current
levels, at comparable treatment times (e.g., of up to three
minute or up to six minutes, respectively, or more or less).

FIG. 15B shows that a selected pretreatment current level
(e.g., up to 375 µA) appears to stimulate increased epidermal
retention for selected components of the topical agent.
Lower microcurrent levels (e.g., up to 250 µA, or up to 125
µA) may stimulate higher retention in the dermis. For all
microcurrent levels, a six minute pretreatment may stimulate
higher skin retention than a three minute pretreatment. Not
that the effect may be continuous with pretreatment time and
across the skin layers, reflecting changes in the correspond-
ing skin structure (e.g., skin cells migrate upward as they
age, and other related structural changes).

FIG. 15C shows that for all current levels there is
increased allantoin flux through selected layers of the skin
sample at an initial time point of 30 m to 1 h following
pretreatment, There may be substantially no flux at a later
time point of 1-6 h; e.g., because all of the agent has been
transmitted. In some application, the agent may be re-

TABLE 5

Round Three pretreatment methodology and experimental design (TNFEW)

| Franz cells | # | Sample | I (µA) | PT (min) | Next steps | Post-pulse/ dosing | Assessment time (hr) | Assay for |
|---|---|---|---|---|---|---|---|---|
| 3 | 1 | PBS | 0 | 0 | drawn off | PBS (1% allantoin) | Post 0.5, 1.0, 6 & 24 hr | allantoin |
| 6 | 2 | PBS | 375 | 3 | drawn off | PBS (1% allantoin) | Post 0.5, 1.0, 6 & 24 hr | allantoin |
| 6 | 3 | PBS | 375 | 6 | drawn off | PBS (1% allantoin) | Post 0.5, 1.0, 6 & 24 hr | allantoin |
| 6 | 5 | PBS | 375 | 12 | drawn off | PBS (1% allantoin) | Post 0.5, 1.0, 6 & 24 hr | allantoin |
| 6 | 6 | PBS | 375 | 36 | drawn off | PBS (1% allantoin) | Post 0.5, 1.0, 6 & 24 hr | allantoin |
| 6 | 7 | PBS | 250 | 3 | drawn off | PBS (1% allantoin) | Post 0.5, 1.0, 6 & 24 hr | allantoin |
| 6 | 8 | PBS | 250 | 6 | drawn off | PBS (1% allantoin) | Post 0.5, 1.0, 6 & 24 hr | allantoin |
| 6 | 9 | PBS | 250 | 12 | drawn off | PBS (1% allantoin) | Post 0.5, 1.0, 6 & 24 hr | allantoin |
| 6 | 10 | PBS | 250 | 36 | drawn off | PBS (1% allantoin) | Post 0.5, 1.0, 6 & 24 hr | allantoin |
| 6 | 11 | PBS | 125 | 3 | drawn off | PBS (1% allantoin) | Post 0.5, 1.0, 6 & 24 hr | allantoin |
| 6 | 12 | PBS | 125 | 6 | drawn off | PBS (1% allantoin) | Post 0.5, 1.0, 6 & 24 hr | allantoin |
| 6 | 13 | PBS | 125 | 12 | drawn off | PBS (1% allantoin) | Post 0.5, 1.0, 6 & 24 hr | allantoin |
| 6 | 14 | PBS | 125 | 36 | drawn off | PBS (1% allantoin) | Post 0.5, 1.0, 6 & 24 hr | allantoin |

FIG. 15A is a bar chart illustrating transdermal allantoin
penetration for selected electrical waveform pretreatment
durations of three and six minutes, at various microcurrent
applied to increase the gradient of the selected component
concentration across selected skin layers, for further
enhanced transmission.

The Round Three testing summary includes the following:

At all current levels there is increased transdermal penetration of allantoin for a six minute pretreatment as compared to a three minute pretreatment. Higher current (e.g., 375 μA or more) and longer pretreatment times (up to six minutes or more) may stimulate greater skin penetration for selected components of the topical agent, than lower current levels (e.g., less than 375 μA), at comparable treatment times of six minutes and three minutes, respectively.

A current level of about 375 μA stimulated increased epidermal retention. Lower microcurrent treatment levels (e.g., about 250 μA or about 125 μA) stimulated higher retention in the dermis. In all microcurrent treatments, a six minute pretreatment stimulated higher skin retention than a three minute pretreatment.

At all current levels there is increased allantoin flux at an initial time point of 30 m to 1 h following treatment, and there may be little or substantially no flux at a later time point of 1-6 h.

Round Four Testing

Round Four testing included an assessment for a NBS agent containing allantoin 0.1 wt % with a TNFEWF (CSW) electrical waveform. The pretreatment was applied with varying CSW electrical waveform current levels (e.g., up to 375 μA, up to 250 μA, or up to 125 μA) and varying pretreatment times (e.g., up to three minutes or more, or up to six minutes or more) with an NBS agent containing allantoin 0.1 wt %.

Table 6 summarizes the Round Four treatment methodology and experimental design, analogous to Table 5 for Round Three (above). In Round Four, New Body Serum (NBS) samples containing with 0.1% allantoin were used. The samples were left on (not drawn off), and there was no pulse treatment or dosing.

Figure 16A:
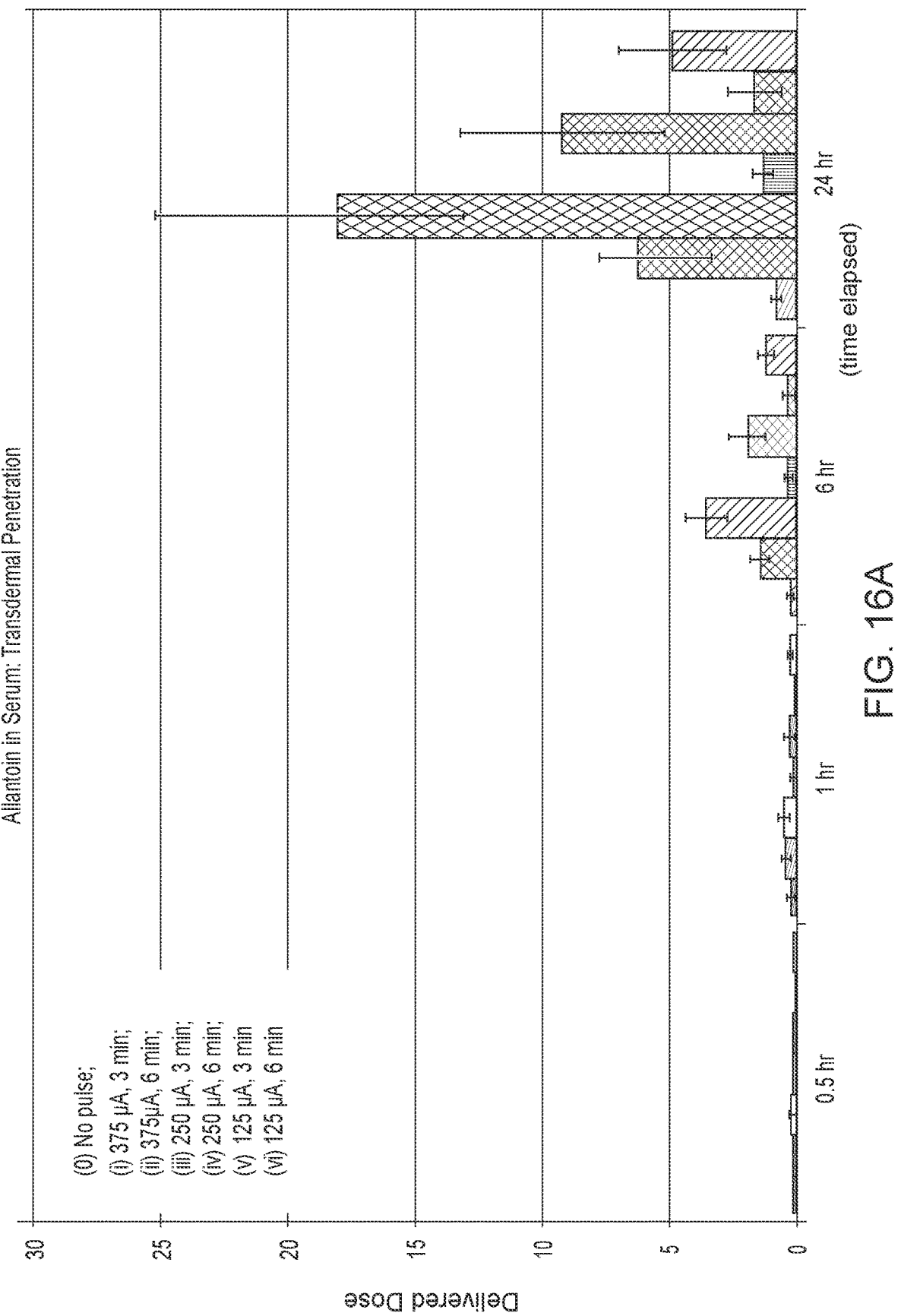
FIGS. 16A, 16B and 16C are bar charts illustrating transdermal penetration, retention and flux for a 0.1% allantoin serum, with selected electrical waveform pretreatment durations of three and six minutes.
Figure 16B:
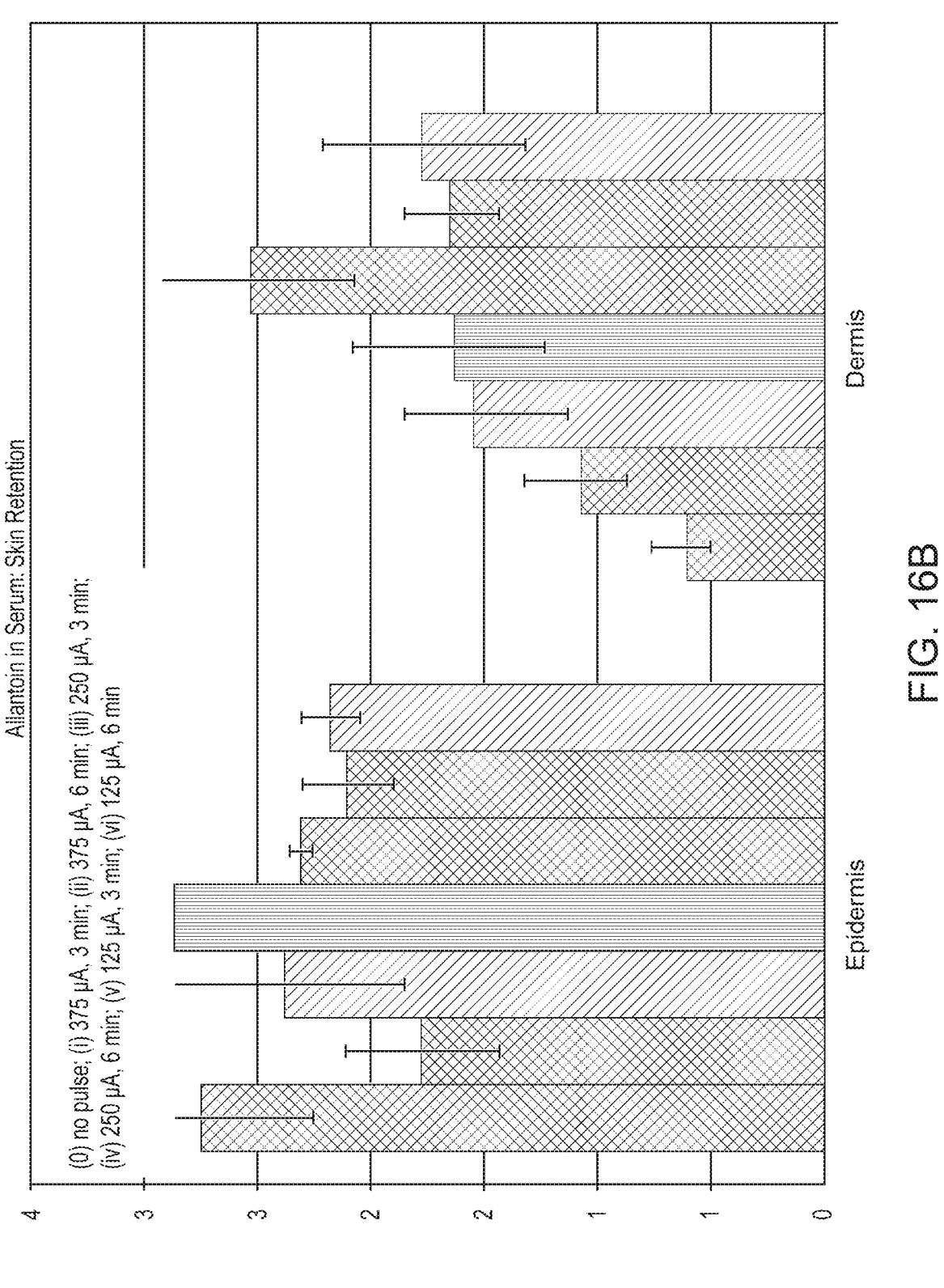
Figure 16C:
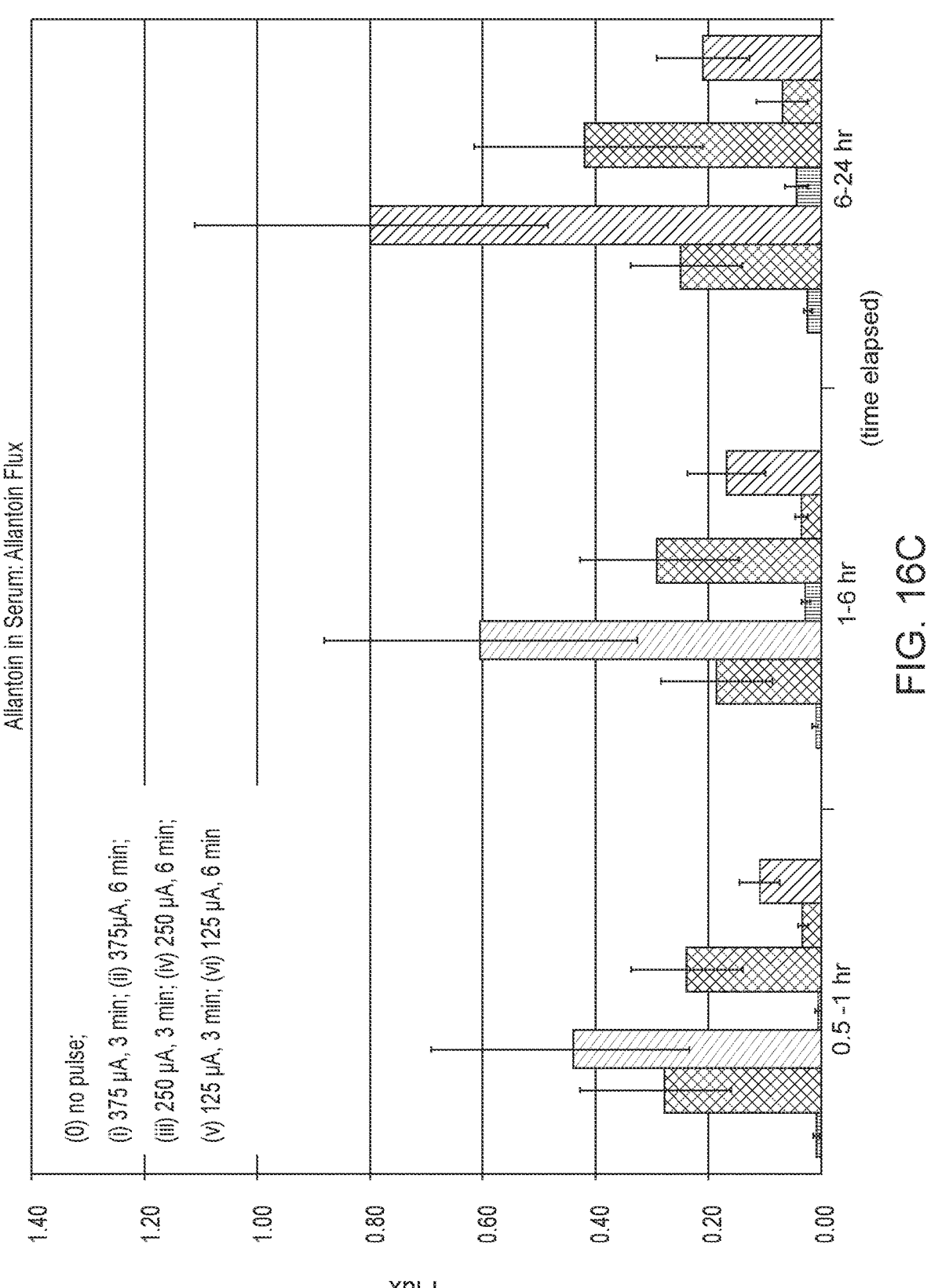

FIG. 16A is a bar chart illustrating transdermal penetration for a 0.1% allantoin serum, for no pulse (no waveform), and selected electrical waveform pretreatment durations of three and six minutes, at various current levels. FIG. 16B is a bar chart illustrating allantoin retention for the 0.1% allantoin serum, with the selected treatments. FIG. 16C is a bar chart illustrating allantoin flux for the 0.1% allantoin serum, with the selected treatments. The treatments are ordered sequentially from (i) to (vi), respectively, and the histogram date ordered accordingly, starting with (0) for no pulse.

As shown in FIG. 16A, at all current levels there is increased transdermal penetration of allantoin for a six minute pretreatment as compared to a three minute pretreatment. Higher current level (e.g., up to 375 μA or more) at higher times (e.g., up to six minutes or more) appear to stimulate greater penetration than lower current levels at comparable treatment times (e.g., of up to six minutes, or up to three minutes, respectively).

TABLE 6

Round Four treatment methodology and
experimental design (TNFEW)

| Franz Cells | # | Sample | I (μA) | PT (min) | Next steps | Post-pulse/ dosing | Assessment time (hr) | Assay for |
|---|---|---|---|---|---|---|---|---|
| 3 | 1 | NBS (0.1%) | 0 | 0 | Not drawn off | None | Post 0.5, 1.0, 6 & 24 hr | allantoin |

TABLE 6-continued

Round Four treatment methodology and
experimental design (TNFEW)

| Franz Cells | # | Sample | I (μA) | PT (min) | Next steps | Post-pulse/ dosing | Assessment time (hr) | Assay for |
|---|---|---|---|---|---|---|---|---|
| 6 | 2 | NBS (0.1%) | 375 | 3 | Not drawn off | None | Post 0.5, 1.0, 6 & 24 hr | allantoin |
| 6 | 3 | NBS (0.1%) | 375 | 6 | Not drawn off | None | Post 0.5, 1.0, 6 & 24 hr | allantoin |
| 6 | 5 | NBS (0.1%) | 375 | 12 | Not drawn off | None | Post 0.5, 1.0, 6 & 24 hr | allantoin |
| 6 | 6 | NBS (0.1%) | 375 | 36 | Not drawn off | None | Post 0.5, 1.0, 6 & 24 hr | allantoin |
| 6 | 7 | NBS (0.1%) | 250 | 3 | Not drawn off | None | Post 0.5, 1.0, 6 & 24 hr | allantoin |
| 6 | 8 | NBS (0.1%) | 250 | 6 | Not drawn off | None | Post 0.5, 1.0, 6 & 24 hr | allantoin |
| 6 | 9 | NBS (0.1%) | 250 | 12 | Not drawn off | None | Post 0.5, 1.0, 6 & 24 hr | allantoin |
| 6 | 10 | NBS (0.1%) | 250 | 36 | Not drawn off | None | Post 0.5, 1.0, 6 & 24 hr | allantoin |
| 6 | 11 | NBS (0.1%) | 125 | 3 | Not drawn off | None | Post 0.5, 1.0, 6 & 24 hr | allantoin |
| 6 | 12 | NBS (0.1%) | 125 | 6 | Not drawn off | None | Post 0.5, 1.0, 6 & 24 hr | allantoin |
| 6 | 13 | NBS (0.1%) | 125 | 12 | Not drawn off | None | Post 0.5, 1.0, 6 & 24 hr | allantoin |
| 6 | 14 | NBS (0.1%) | 125 | 36 | Not drawn off | None | Post 0.5, 1.0, 6 & 24 hr | allantoin |

As shown in FIG. 16B, a current level of about 375 μA and six minute pretreatment time seem to stimulate increased epidermal and dermal retention of allantoin as compared to a three minute pretreatment. At a current level of about 250 μA, a three minute pretreatment appears to stimulate allantoin retention in the epidermis, and a six minute pretreatment appears to stimulate additional allantoin retention in the dermis. At a current level of about 125 μA, three minute and six minute electrical waveform pretreatments both seem to stimulate comparable allantoin retention.

As shown in FIG. 16C, at all current levels (e.g., up to 375 μA, up to 250 μA, and up to 125 μA), from 0.5 h to 24 h after pretreatment, a six minute pretreatment induces higher allantoin flux as compared to a three minute electrical pretreatment.

The Round Four summary includes:

Higher current and longer pretreatment times seem to be better in stimulating transdermal penetration, skin retention and allantoin flux.

A current level of about 375 μA and six minute pretreatment stimulates better NBS agent (allantoin 1.0 wt %) transdermal penetration, skin retention and allantoin flux, as compared to three minute pretreatment.

Clinical Assessment

Clinical assessment has been performed for low level microcurrent (substantially less than one milliamp; e.g., ≤0.5 mA) of short duration (substantially less than ten minutes; e.g., ≤5 m), and for related treatment systems, applicable in enhancing allantoin penetration and improving the appearance of skin cellulite, radiance, texture, and firmness. Assessment data are included in FIGS. 17A-20B.

One object of the trial was to assess a treatment system using low level microcurrent of short duration in enhancing the improvement of the appearance of skin cellulite, radiance, texture, and firmness. Another object was to assess a treatment system using low level microcurrent of short duration in enhancing the penetration of an active ingredient in a topical body serum by tracking allantoin penetration in skin.

Low level DC microcurrent can used to enable electrically driven drug delivery in skin wounds and ulcerations (see S. Zhao, A. S. Mehta and M. Zhao, "Biomedical applications of electrical stimulation. Cell. Mol. Life Sci., Jan. 23, 2020, which is incorporated by reference herein, in the entirety and for all purposes). However, it is not clear from the literature whether a system comprising very low-level DC microcurrent of short-term duration can improve the penetration of topical actives through skin and also improve skin appearance, for example the characteristics of cellulite, radiance, texture and firmness.

Thirty-one female subjects were enrolled in a single site twelve-week study. The study involved treatment of either the left upper arm and left upper thigh, or the right upper arm and right upper thigh, randomized for each subject, with a microcurrent device and a topical body serum followed by post-device treatment application of a moisturizing body lotion. The topical body serum contained an ingredient, allantoin, with anti-inflammatory, cell turnover, collagen stimulating and hydration functions. The post-device treatment moisturizing body lotion contained actives including *Camellia sinensis* leaf extract (or green tea extract), with anti-adipogenic function, and sodium hyaluronate, palmitoyl hexapeptide-12, as actives for moisturizing and barrier strengthening functional activity.

The subjects treated a targeted area of the (randomly selected) upper arm and upper thigh with a microcurrent device set at a low microcurrent dose of 375 microampere (μA) with topical body serum for five minutes, once a day, three days a week (every other day), followed by application of a post-device treatment moisturizing body lotion twice daily, for a period of twelve weeks. Each subject's upper arm was assessed for texture, firmness and radiance and upper thigh assessed for cellulite texture, firmness and radiance during clinic visits at baseline, post-application, week one, two, four, eight and twelve with expert grading and subject self-perception using a five-point ordinal scale.

Cellulite was further evaluated by measuring circumference of upper thigh during each visit. At the end of study completion at twelve weeks, twenty tape strips were removed from the treated upper thigh area of five subjects chosen based on visible improvement in skin attributes and five control strips were obtained from an untreated site on the upper thigh. Tape strips from treated and control (untreated) sites were assessed for penetration of allantoin from the topical body serum using Liquid chromatography coupled to mass spectrophotometer (LC-MS) system.

The twelve-week study was conducted in the thirty-one female subjects using a system including a non-invasive negative DC microcurrent device with a topical body serum containing allantoin as the active ingredient followed by treatment with post-device moisturizing lotion. Consistent areas on the upper thigh and upper arm were evaluated visually by expert graders and subject self-assessment using the five-point ordinal scale for improvement in skin cellulite, radiance, texture, and firmness at baseline, post-application, and weeks one, two, four, eight, and twelve, following application.

In addition, the circumference of each subject's upper thigh was measured during each visit as an indicator for improvement in slimming and firmness (see M. H. Gold, K. A. Khatri, K. Hails, R. A. Weiss and N. Fournier, "Reduction in thigh circumference and improvement in appearance of cellulite," J. of Cosmetic and Laser Therapy 13, February 2011, which is incorporated by reference herein, in the entirety and for all purposes). At the end of study, the twenty tape strips were collected from the treated upper thigh area, and from an untreated upper thigh area from five randomly chosen subjects. Five tape strips from both treated and untreated areas of upper thigh were evaluated for accumulation of allantoin using LC-MS spectroscopy.

The expert grader analysis and subject self-perception assessment also showed significant improvement in the appearance of cellulite, radiance, texture and firmness at twelve weeks following treatment, when compared to baseline. Further, the amount of allantoin recovered by the tape stripping method increased over the background skin allantoin level in the early tape strips (one through five) but tended to decrease as the tape strips were removed from deeper epidermis tissue. The low level DC microcurrent of short duration treatment system was shown to enhance the skin appearance benefit of the topically applied body serum containing allantoin.

Figure 17A:
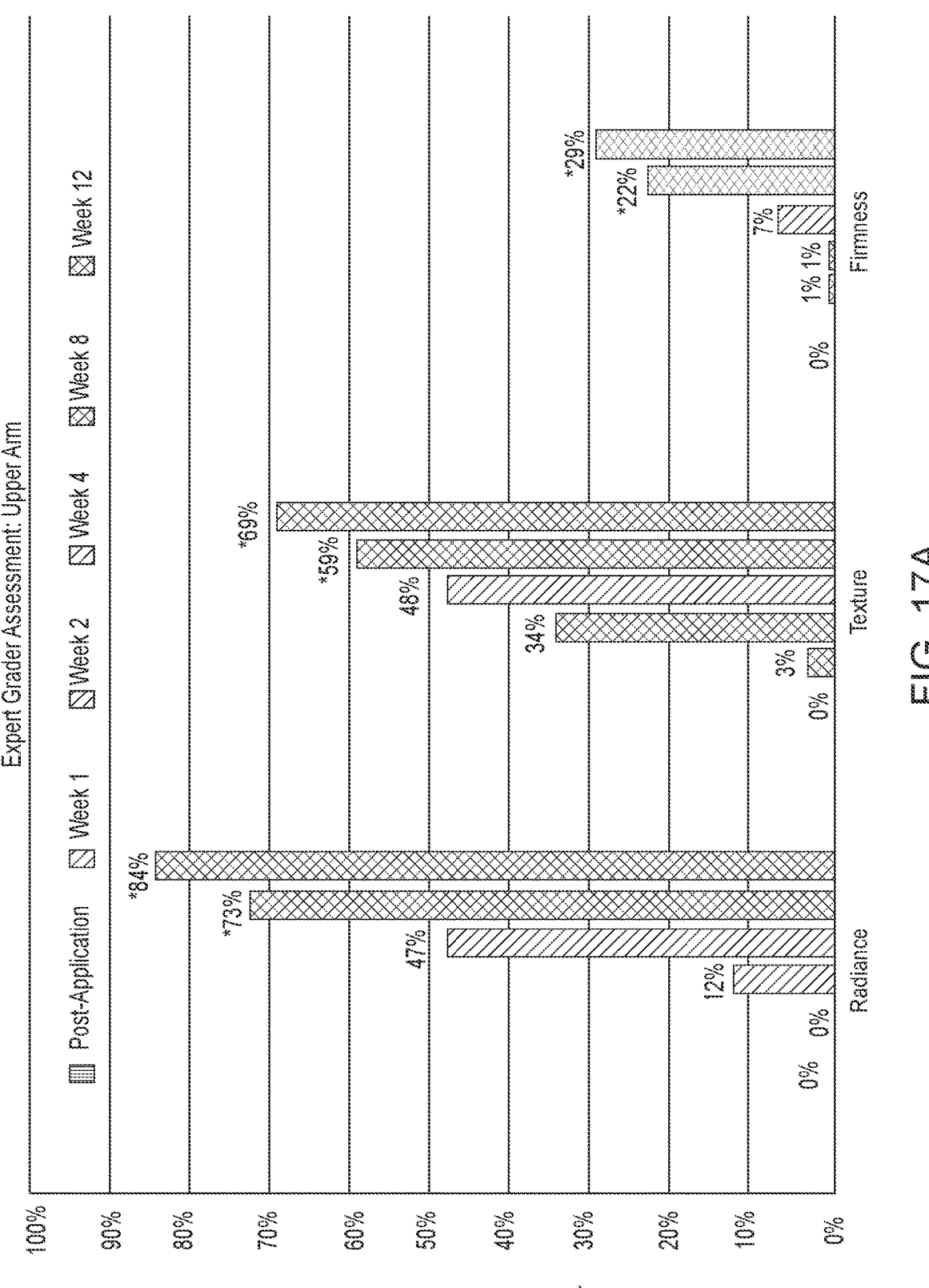
FIGS. 17A and 17B are histograms illustrating expert grader assessments of skin radiance, texture and firmness for treated upper arm and upper thigh areas, and for cellulite appearance in the upper thigh.
Figure 17B:
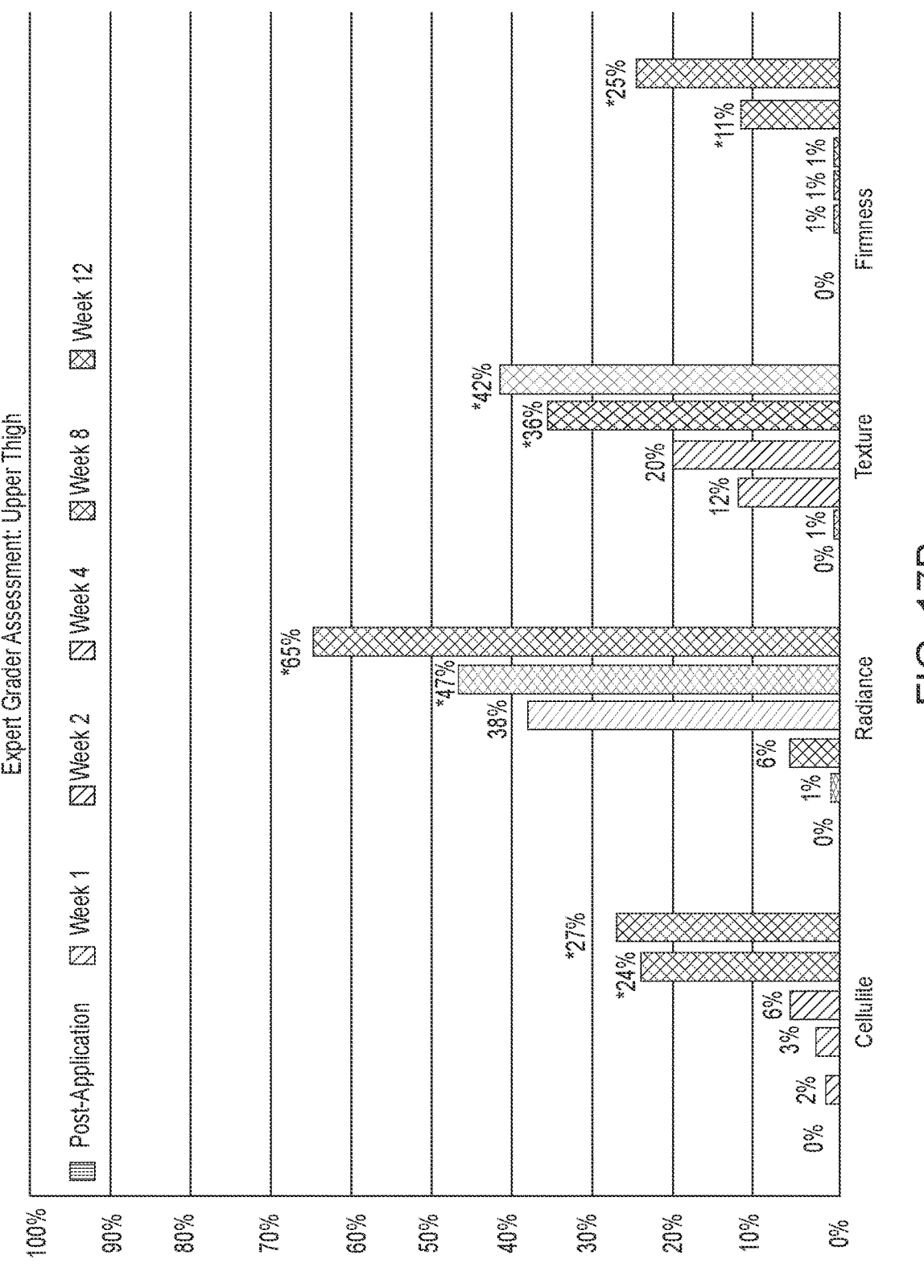

FIGS. 17A and 17B are histograms illustrating expert grader assessments of skin radiance, texture and firmness, for treated upper arm and upper thigh areas. Cellulite appearance is also included for the upper thigh.

The expert grader results are shown on the vertical scale, in relative (percentage) improvement over the defined baseline (e.g., pre-treatment), for post-application, and at weeks one, two, four, eight and twelve of the trial. The expert grader assessments followed application of a low level microcurrent treatment with topical body serum, and a "post-device" treatment lotion, after application of the microcurrent treatment.

The figures show significantly improved skin radiance, texture and firmness on the upper arm area (FIG. 17A), and on the upper thigh area (FIG. 17B) from baseline, from post-application to weeks one, two, four, eight and twelve, displayed as histogram data arranged accordingly from left to right. Cellulite appearance also improved in the upper thigh from baseline, post-application at weeks one to twelve of the treatment (FIG. 17B). Percentages in highlighted text ("*") indicate statistical significance over baseline, exhibited at weeks eight and twelve for radiance, texture, and firmness in the upper arm data (FIG. 17A), and for the corresponding upper thigh data (FIG. 17B).

Comfort and tolerance results were also considered. There were no reports of skin discomfort by any of the study subjects who used the microcurrent treatment device with the topical body gel.

Figure 18:
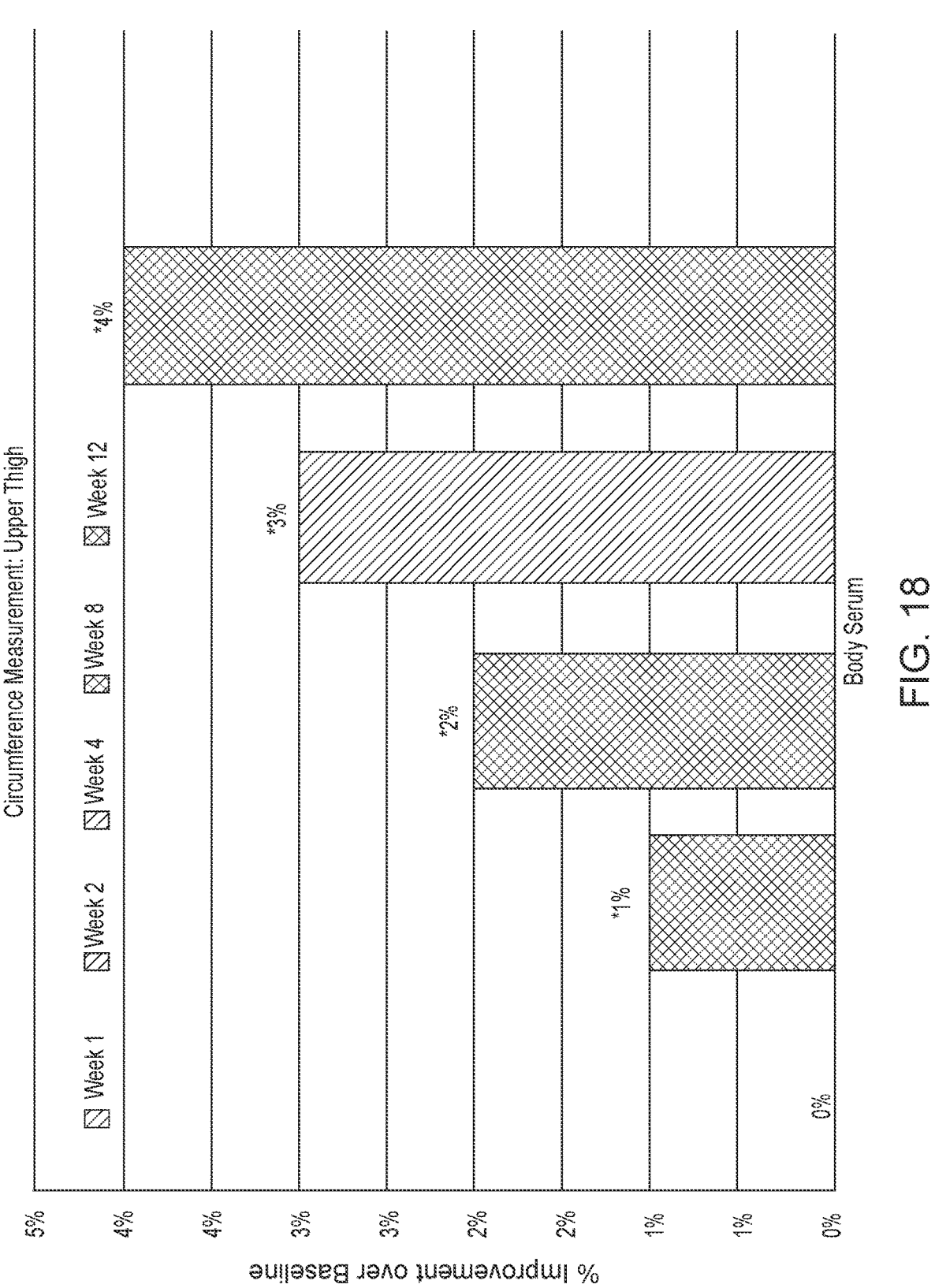
FIG. 18 is a histogram illustrating upper thigh area circumference measurements.

FIG. 18 is a histogram illustrating circumference measurements of the upper thigh area. Relative (percentage) improvement is show on the vertical scale, for measurements taken at weeks one, two, four, eight and twelve of the trial. Percentages in highlighted text ("*") indicate statistical significance over the baseline, at two, four, eight and twelve weeks. The measurements of thigh circumference showed improvement of about 4% following twelve weeks of treatment, over the baseline.

Figure 19A:
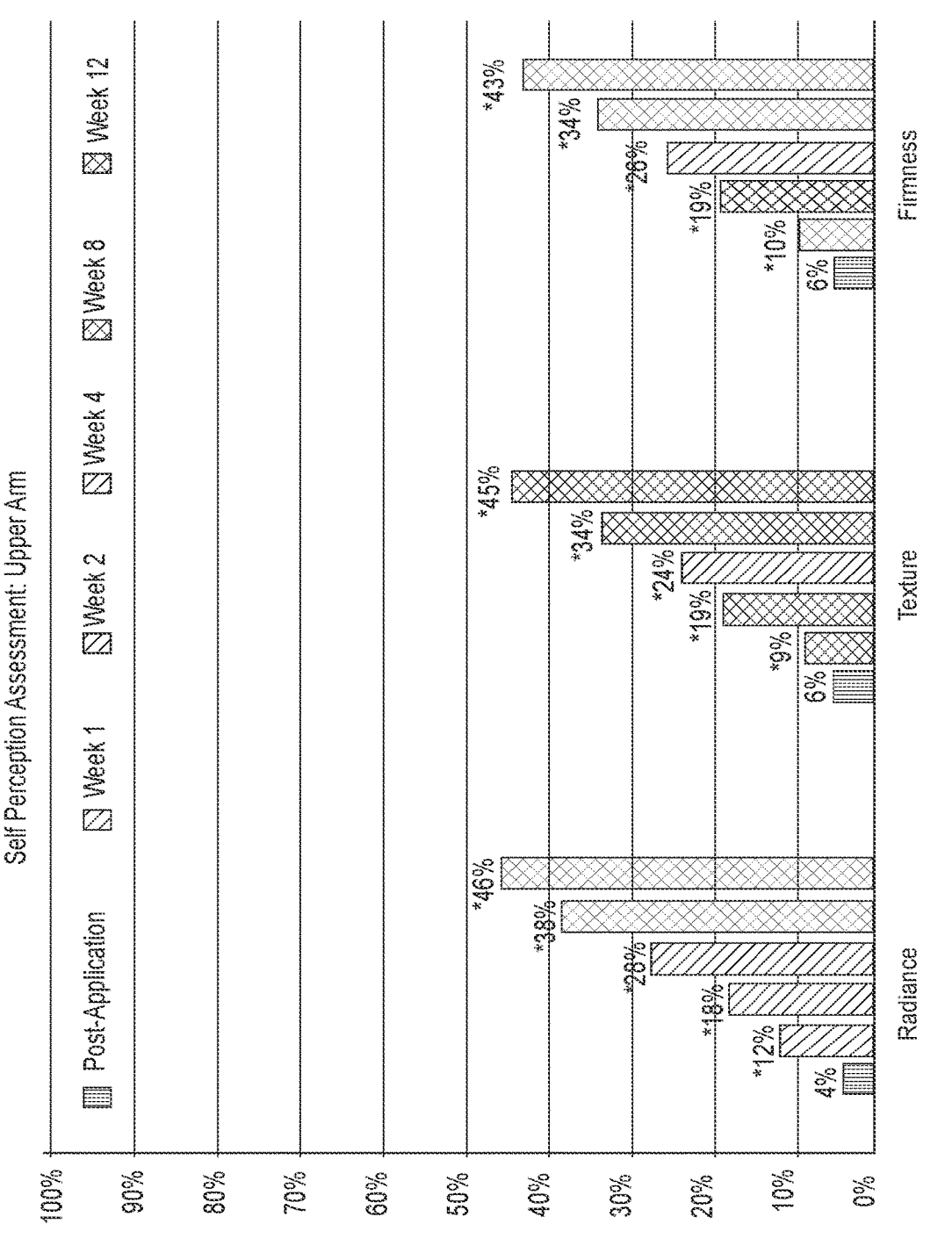
FIGS. 19A and 19B are histograms illustrating self-perception assessments of skin radiance, texture and firmness for treated upper arm and upper thigh areas, and for cellulite appearance in the upper thigh.
Figure 19B:
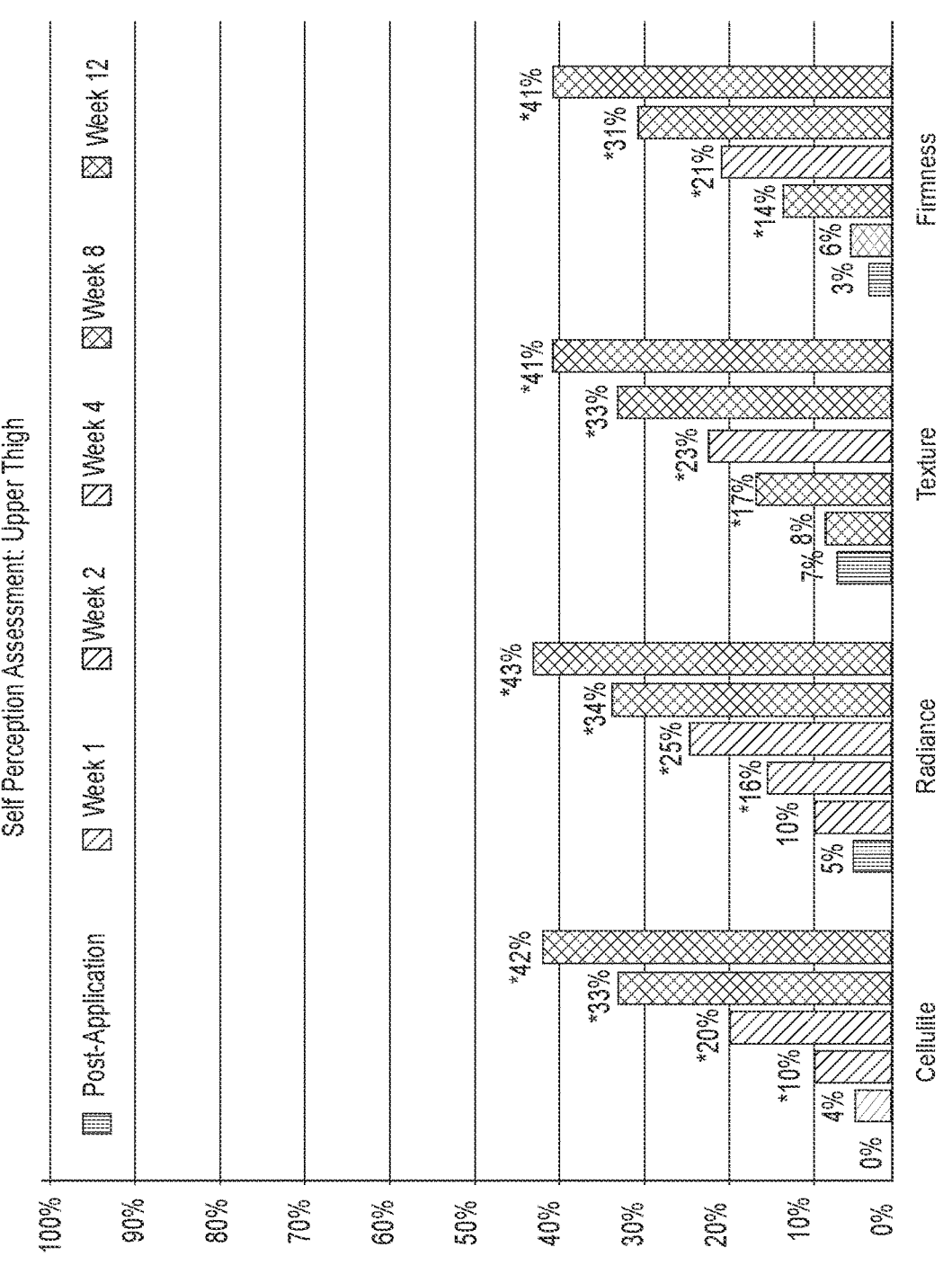

FIGS. 19A and 19B are histograms illustrating self-perception assessments of skin radiance, texture and firmness for treated upper arm and upper thigh areas. Cellulite appearance is also included for the upper thigh.

The self-perception assessment results are shown on the vertical scale, in relative (percentage) improvement over the defined baseline (e.g., pre-treatment), for post-application, and at weeks one, two, four, eight and twelve of the study. The subject self-perception assessments generally match with the expert grader assessments, indicating significant improvement in skin radiance, texture and firmness in the treated upper arm area (FIG. 19A), and for cellulite appearance, skin radiance, texture and firmness in the upper thigh (FIG. 19B), over baseline and up to twelve weeks of treatment. Percentage in bold or highlighted (red) test indicate statistical significance over the baseline, at one, two, three, four, eight and twelve weeks for the upper arm (FIG. 19A), and at four, eight and twelve weeks for the upper thigh (FIG. 19B).

Figures 20A, 20B:
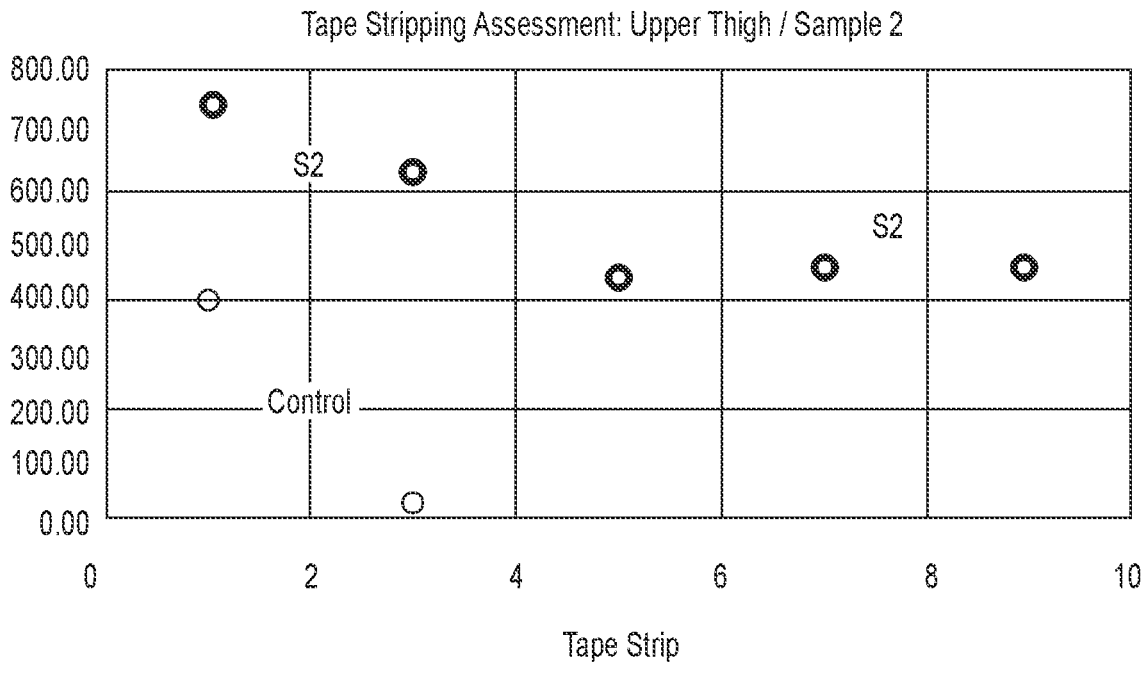
FIGS. 20A and 20B are scatter plots illustrating a tape stripping assessment for allantoin recovery in the upper thigh.

FIGS. 20A and 20B are scatter plots illustrating a tape stripping assessment for allantoin recovery in the upper thigh. The results include representative, anonymous, arbitrarily-labeled samples (S2 and S4), as compared to corresponding controls. The allantoin recovery level appears on the vertical axis, in arbitrary units, with tape strip index on the horizontal.

The representative subjects in FIGS. 20A and 20B were selected from a group of five, showing successful allantoin recovery with the tape strip sampling method. The amount of allantoin recovered from the low-level microcurrent treated skin areas was increased over the background allantoin level (controls; lower dots), in the early epidermal tape strips (strips one to five). The level tended to decrease, as expected, from tape strips removed from deeper epidermis tissue. These levels are noted by samples S2 and S4 (upper dots).

Generally, the clinical trial data demonstrate that a system for low level microcurrent treatment of short duration (as little as five minutes) with a topical body serum, and post-device treatment with body lotion on the skin, enhanced skin penetration of the topical as demonstrated by accumulation of allantoin, an active in selected body serum topicals. Expert grading and self-perception assessments showed substantial or significant improvement in several skin attributes over baseline, from post-application, and over weeks one to twelve of the clinical assessment. In addition, a 4.0% improvement in thigh circumference was observed at week twelve, over the defined baseline, consistent with improved skin firmness and slimming effect, and consistent with overall improvement of cellulite appearance. Further, the system for low level microcurrent treatment with the selected topical agents was well tolerated by all subjects, with no reported adverse events during the twelve-week trial treatment period.

EXAMPLES

In any of the various examples and embodiments described herein, the method can be used for cosmetic skin treatment, as opposed to medical procedures, as may be employed in other examples and embodiments, subject to applicable regulations. A device for implementing the method is also encompassed.

In some examples and embodiments, the method includes pretreating a skin surface of a subject by applying a voltage or current signal surface via one or more electrodes; e.g., where power is output to the skin surface, and modulating the voltage or current signal; e.g., where the power output is selected to enhance or increase permeability of the skin surface. Depending on application, the method may also include treating the skin surface by applying an agent thereto; e.g., where permeability of the skin to one or more components of the agent is enhanced or increased, responsive to the modulated power output while pretreating the skin surface, absent further voltage or current signal applied to the skin surface via the one or more electrodes.

In any of these examples and embodiments, the method can include generating the voltage or current signal as a DC, pulsed DC, microcurrent, or pulsed microcurrent waveform. The power output to the skin may be charge balanced, or a polarity of the power output to the skin may be alternated at periodic or aperiodic intervals.

In any of these examples and embodiments, the method the agent can be applied to the skin surface before or during pretreating the skin surface, or after pretreating the skin surface; e.g., where no further voltage or current signal is applied following application of the agent.

In any of these examples and embodiments, modulating the voltage or current signal can comprise adjusting an amplitude of the signal such that the power output is selected for user comfort or efficacy of the enhancement or increase in permeability, or both; e.g., as compared to said power output absent modulating the voltage or current signal. The modulated power output can be selected for the enhanced or increased permeability to include enhanced or increased absorption, adsorption, diffusion or transmissibility of the one or more components of the agent into or through one or more of layers of the skin surface during the treatment period; e.g., as compared to said absorption, adsorption, diffusion or transmissibility absent applying the voltage or current signal to the skin surface.

In any of these examples and embodiments, the one or more layers of the skin surface may comprise a stratum corneum, outer epidermis, lower epidermis, or dermis, or wherein the one or more layers of the skin surface comprise vasculature or fibroblasts. The treatment period can extend at least one to two hours after application of the voltage or current signal, or more, at least two to four hours after application of the voltage or current signal, or more, at least four to eight hours after application of the voltage or current signal, or more, at least six to twelve hours after application of the voltage or current signal, or more, at least twelve to twenty-four hours after application of the voltage or current signal, or more, or at least twenty-four hours after application of the voltage or current signal, or more.

In any of these examples and embodiments, the method can include defining a latency period following pretreating the skin surface; e.g., where no further voltage or current signal is applied to the skin surface via the one or more electrodes during the latency period. The agent can be applied to the skin surface following the latency period, and/or the agent can be re-applied to the skin surface or applied a plurality of times to the skin surface at different times during or after the latency period, or a plurality of different agents can be applied to the skin surface; e.g., at the same or different times during or after the latency period.

In any of these examples and embodiments, the latency period may extend for at least one to two minutes following application of the voltage or current signal, at least two to five minutes following application of the voltage or current signal, at least five to ten minutes following application of the voltage or current signal, at least ten to thirty minutes following application of the voltage or current signal, at least thirty minutes to an hour following application of the voltage or current signal, or at least one hour following application of the voltage or current signal, or more. For example, the latency period may extend for at least one to two hours following application of the voltage or current signal, at least two to four hours following application of the voltage or current signal, at least four to eight hours following application of the voltage or current signal, at least six to twelve hours following application of the voltage or current signal, at least twelve to twenty-four hours following application of the voltage or current signal, or at least twenty four hours following application of the voltage or current signal, or more.

In any of these examples and embodiments, the method can include modulating the power output to the skin surface based on a feedback signal responsive to change in the applied voltage or current signal, and one or more of sensing the voltage or current signal proximate one or more of the electrodes; e.g., where the change is based at least in part on the sensed voltage or current signal, and/or defining a response curve for the power output; e.g., where the response curve modulates the power output between predetermined minimum and maximum power levels, based on the feedback signal.

In any of these examples and embodiments, the method can include one or more of defining a threshold for change in the feedback signal, reducing the power output or lowering the response curve to or toward the predetermined minimum power level; e.g., based on a change in the feedback signal meeting or exceeding the threshold, and/or increasing the power output or raising the response curve to or toward the predetermined maximum power level; e.g., based on an absence of change in the feedback signal meeting or exceeding the threshold.

In any of these examples and embodiments, the method can include generating a waveform for applying the voltage or current signal to the skin surface, wherein the waveform comprises alternating sequences of positive and negative polarity. Modulating the power output may comprise controlling a pulse width, period or amplitude of the waveform based on an impedance between two of the electrodes; e.g., as determined by the feedback circuit.

In any of these examples and embodiments, the method modulating the power output may be performed with a three-terminal device having a first terminal coupled to a voltage sensor adjacent one or more of the electrodes, a second terminal coupled to the feedback signal, and a gate adapted to control the power output.

In any of these examples and embodiments, the alternating sequences of positive and negative polarity may be symmetric, aperiodic, or have randomized or pseudorandom pulse width, pulse height or period. The positive and negative components of the waveform may be charge balanced over a period of about 0.1-0.2 s, or less, a period of about 0.2-0.5 s, or less, a period of about 0.5-1.0 s, or less, a period of about 1.0-1.5 s, or less, or a period of about 1.4 s, or a combination thereof. The voltage or current signal applied to the skin surface can include voltage or current pulses having amplitudes of about 100 µA or less, about 100-150 µA, or less, about 150-200 µA, or less, about 200-250 µA, or less, or about 250 µA or less.

In any of these examples and embodiments, the voltage or current signals applied to the skin surface may comprise voltage or current pulses have individual pulse widths between about 1-10 ms, or less, between about 10-20 ms, or less, between about 20-50 ms, or less, between about 50-100 ms, or less, or about 100 ms or less. The voltage or current signals applied to the skin surface may comprise alternating sequences of voltage or current pulses; e.g., with the alternating sequences each comprising between two and six individual pulses, or less, between five and ten individual pulses, or less, between six and twelve individual pulses, or less, between ten and twenty individual pulses, or less, between twenty and fifty individual pulses, or less, or fifty individual pulses or less.

In any of these examples and embodiments, applying the voltage or current signal and modulating the power output to the skin surface may be performed for a pretreatment period selected to achieve the enhanced or increased permeability of the skin upon application of the agent. The pretreatment period can be selected for enhanced or increased absorption, adsorption, diffusion or transmissibility of the one or more components of the agent into or through one or more of layers of the skin surface during the treatment period; e.g., as compared to said absorption, adsorption, diffusion or transmissibility absent applying the voltage or current signal to the skin surface. The pretreatment period may range be between about one to two minutes, or less, between about two to three minutes, or less, between about three to five minutes, or less, between about five to ten minutes, or less, or about ten minutes or less.

In any of these examples and embodiments, the one or more components of the agent for which the permeability is enhanced or increased may comprise ions or ionic or polar molecules. The one or more components of the agent for which the permeability is enhanced or increased may also comprise nonionic or nonpolar molecules, or proteins, amino acids, genetic material, genetic markers, allantoin, or caffeine.

In any of these examples and embodiments, the method can include applying a topical to the skin surface; e.g., where the topical is applied before applying the voltage or current signal, or while applying the voltage or current signal. The topical can include a conducting gel, a serum, a moisturizer, or a base component of a skin treatment product, or wherein the topical forms an electrically conducting path for the voltage or current signal between one or more of the electrodes and the skin surface.

In any of these examples and embodiments, the method can be applied for cosmetic skin treatment. The examples and embodiments can be performed in any order or combination. A non-transitory computer-readable medium can also be provided with program code stored thereon, where the program code is executable on a computer processor or controller to perform a skin treatment method according to these examples and embodiments, in any order or combination.

A skin treatment system can include one or more electrodes configured or adapted to apply a voltage or current signal according to any of these examples and embodiments, or any combination thereof. A voltage or current source can be configured or adapted to generate the voltage or current signal, and control circuitry can be configured or adapted to modulate the power output to the skin surface, as described herein. For example, the one or more electrodes may comprise one or more pairs of electrodes having an elongated, lobed structure, and/or the voltage or current signal can be applied with opposite polarity to the electrodes in each pair.

In various examples and embodiments, the method includes placing at least two electrodes adjacent a skin area, providing a microcurrent pretreatment to the skin area via a voltage or current waveform applied to the electrodes, and modulating a power output of the microcurrent pretreatment to enhance or increase permeability of the skin area for a selected treatment substance. The method may also include one or more of removing the electrodes from adjacent the skin area, and/or applying the selected treatment substance to the skin area; e.g., where the permeability of the skin area to the selected treatment substance is increased following removal of the electrodes.

In any of these examples and embodiments, modulating the power output can comprise regulating the power output between minimum and maximum power levels selected to enhance or increase the permeability of the skin surface to the selected treatment substance in the treatment phase; e.g., as compared to such a skin surface absent application of the microcurrent pretreatment in the pretreatment phase. The minimum and maximum power levels may be further selected to maintain user comfort, as compared to application of the microcurrent pretreatment absent modulating the power output.

In any of these examples and embodiments, the waveform can have a DC, pulsed DC, microcurrent, or charge-balanced microcurrent functional form; e.g., as defined over a period for modulating the power output. The period may rage from of at least 100 microseconds to at least 1 millisecond, at least 10 milliseconds, at least 100 milliseconds, at least one second, or at least two seconds, and the period may also range from less than two seconds, or less than one second.

In any of these examples and embodiments, or any combination thereof, the method may be performed for a cosmetic skin treatment. For example, the microcurrent pretreatment may be applied for a period of at least ten seconds, at least thirty seconds, at least one minute, at least two minutes, at least five minutes, at least ten minutes, or less than ten minutes, or less than five minutes. The selected treatment substance may comprise ions, ionic or polar molecules, nonionic or nonpolar molecules, proteins, amino acids, genetic material, genetic markers, allantoin, or caffeine.

In various examples and embodiments, a method for cosmetic skin treatment includes a pretreatment phase; e.g., including disposing at least two electrodes adjacent a skin surface; e.g., with an area of the skin surface therebetween, and providing a microcurrent pretreatment to the area of the skin surface via electrical waveform applied to the electrodes; e.g., where the electrical waveform comprises one or more pulses with the same or opposite polarity. A treatment phase may follow the pretreatment phase; e.g., including applying a treatment substance to the area of the skin surface, where permeability of the skin surface to the treatment substance is enhanced or increased responsive to the microcurrent pretreatment in the area between the electrodes, absent further application of the electrical waveform during the treatment phase.

In any of these examples and embodiments, the electrical waveform may have a DC, pulsed DC, microcurrent, or charge-balanced microcurrent functional form. The method may also include regulating or modulating a power output of the electrical waveform in the pretreatment phase; e.g., where the power output is selected to enhance or increase the permeability of the skin surface to the treatment substance in the treatment phase, or to enhance or increase user comfort during the pretreatment phase, or both, as compared to application of the microcurrent pretreatment absent regulating or modulating the power output in the pretreatment phase.

Any of these examples and embodiments can include a latency phase defined between the pretreatment phase and the treatment phase; e.g., where the latency phase extends for a period of at least five minutes, at least ten minutes, at least thirty minutes, at least one hour, at least two hours, at least four hours, at least eight hours, at least twelve hours, or at least twenty-four hours. The treatment phase can extend for a period of at least five minutes, at least ten minutes, at least thirty minutes, at least one hour, at least two hours, at least four hours, at least eight hours, at least twelve hours, at least twenty-four hours, or at least forty-eight hours; e.g., during which the permeability of the skin surface to the treatment substance is increased or enhances, as compared to permeability of such a skin surface absent the pretreatment phase.

In any of these examples and embodiments may include applying a conducting gel or fluid to the skin surface prior to or during the pretreatment phase. For example, the conducting gel or fluid can be selected to form a conducting path between the electrodes and the skin surface, or for modulating a current density of the microcurrent pretreatment along the area of the skin surface between the electrodes, or both.

A method of cosmetic skin treatment can be performed according to any of these examples and embodiment, in any order or combination. A device can be configured or adapted to perform a method of cosmetic skin treatment according to any of these examples and embodiment, in any order or combination. A non-transitory computer-readable medium can be provided with program code stored thereon, where the program code is executable on a computer processor or controller to perform a cosmetic skin treatment method according to any of these examples and embodiments, in any order or combination.

This disclosure has been made with respect to representative examples and embodiments. Each and every example embodiment of the invention disclosed here can be used either alone or in combination with any other embodiment or example that is described or illustrated herein, and each may incorporate additional modifications, changes, equivalents, and alternatives that fall within the breadth of disclosure, as read and understood by a person of ordinary skill, and without departing from practice of the invention as claimed. These various examples and embodiments are provided by way of illustration, and should not be construed to limit the scope of the invention, nor to limit the meets and bounds of coverage as defined by the plain language of the claims.

The invention claimed is:

1. A method comprising:

pretreating a skin surface of a subject by applying a voltage or current signal to the skin surface via one or more electrodes, wherein power is output to the skin surface, and modulating the voltage or current signal, wherein the power output is selected to enhance or increase permeability of the skin surface; and treating the skin surface by applying an agent thereto;

wherein permeability of the skin to one or more components of the agent is enhanced or increased, responsive to the modulated power output while pretreating the skin surface, absent further voltage or current signal applied to the skin surface via the one or more electrodes; and generating a feedback signal responsive to change in the applied voltage or current signal, wherein the change is based at least in part on sensing the voltage or current signal proximate one or more of the electrodes;

defining a response curve for modulating the power output between predetermined minimum and maximum power levels, based on the feedback signal; and reducing the power output by lowering the response curve to or toward the predetermined minimum power level, based on a change in the feedback signal meeting or exceeding a threshold, or increasing the power output by raising the response curve to or toward the predetermined maximum power level, based on an absence of change in the feedback signal meeting or exceeding the threshold.

2. The method of claim 1, further comprising:

generating the voltage or current signal as a DC, pulsed DC, microcurrent, or pulsed microcurrent waveform; wherein the power output to the skin is charge balanced.

3. The method of claim 1, wherein:

the modulated power output is selected for enhanced or increased absorption, adsorption, diffusion or transmissibility of the one or more components of the agent into or through one or more of layers of the skin surface during the treatment period, as compared to said absorption, adsorption, diffusion or transmissibility absent applying the voltage or current signal to the skin surface; and the one or more layers of the skin surface comprise a stratum corneum, outer epidermis, lower epidermis, or dermis, or wherein the one or more layers of the skin surface comprise vasculature or fibroblasts.

4. The method of claim 1, wherein the treatment period extends at least one to two hours after application of the voltage or current signal, or at least twelve to twenty-four hours after application of the voltage or current signal.

5. The method of claim 1, further comprising defining a latency period following pretreating the skin surface, wherein no further voltage or current signal is applied to the skin surface via the one or more electrodes during the latency period, wherein:

the agent is applied to the skin surface following the latency period; and the latency period extends for at least one to two minutes following application of the voltage or current signal, at least one hour following application of the voltage or current signal, or at least six to twelve hours following application of the voltage or current signal.

6. The method of claim 1, further comprising generating a waveform for applying the voltage or current signal to the skin surface, wherein the waveform comprises alternating sequences of positive and negative polarity.

7. The method of claim 6, wherein the alternating sequences of positive and negative polarity are symmetric or aperiodic, or have randomized or pseudorandom pulse width, pulse height or period.

8. The method of claim 1, wherein the voltage or current signal applied to the skin surface comprises:

voltage or current pulses having amplitudes of 100 μA or less, or between 100 and 250 μA; and voltage or current pulses having individual pulse widths between 1 and 10 ms or less, or between 10 and 100 ms.

9. The method of claim 1, wherein applying the voltage or current signal and modulating the power output to the skin surface are performed for a pretreatment period selected to achieve the enhanced or increased permeability of the skin upon application of the agent, and:

wherein the pretreatment period is selected for enhanced or increased absorption, adsorption, diffusion or transmissibility of the one or more components of the agent into or through one or more of layers of the skin surface during the treatment period, as compared to said absorption, adsorption, diffusion or transmissibility absent applying the voltage or current signal to the skin surface; or wherein the pretreatment period is between one and two minutes, or between two and ten minutes.

10. The method of claim 1, wherein the one or more components of the agent for which the permeability is enhanced or increased comprise one or more ions or ionic or polar molecules, proteins or amino acids, or genetic material, genetic markers, allantoin, or caffeine.

11. The method of claim 1, further comprising applying a topical to the skin surface, wherein the topical is applied before applying the voltage or current signal, or while applying the voltage or current signal, wherein the topical comprises a conducting gel, a serum, a moisturizer, or a base component of a skin treatment product, or wherein the topical forms an electrically conducting path for the voltage or current signal between one or more of the electrodes and the skin surface.

12. A non-transitory computer-readable medium with program code stored thereon, the program code executable on a computer processor or controller to perform a skin treatment method according to claim 1.

13. A method comprising:

placing at least two electrodes adjacent a skin area;

providing a microcurrent pretreatment to the skin area via a voltage or current waveform applied to the electrodes;

modulating a power output of the microcurrent pretreatment to enhance or increase permeability of the skin area for a selected treatment substance;

removing the electrodes from adjacent the skin area; and applying the selected treatment substance to the skin area, wherein the permeability of the skin area to the selected treatment substance is enhanced or increased following removal of the electrodes;

wherein modulating the power output comprises regulating the power output between predetermined minimum and maximum power levels selected to enhance or increase the permeability of the skin surface to the selected treatment substance in the treatment phase, as compared to such a skin surface absent application of the microcurrent pretreatment in the pretreatment phase; and generating a feedback signal responsive to change in the voltage or current waveform, wherein the change is based at least in part on sensing the voltage or current waveform proximate one or more of the electrodes;

defining a response curve for modulating the power output between the predetermined minimum and maximum power levels, based on the feedback signal; and reducing the power output by lowering the response curve to or toward the predetermined minimum power level, based on a change in the feedback signal meeting or exceeding a threshold, or increasing the power output by raising the response curve to or toward the predetermined maximum power level, based on an absence of change in the feedback signal meeting or exceeding the threshold.

14. The method of claim 13, wherein:

the waveform has charge-balanced microcurrent functional form, as defined over a period for modulating the power output of at least 100 microseconds, at least 100 milliseconds, or at least one second.

15. A method for cosmetic treatment of a skin surface comprising a skin area according to claim 13, and further comprising:

a pretreatment phase, comprising:

disposing the at least two electrodes adjacent the skin surface, with the skin area of the skin surface therebetween, and providing a microcurrent pretreatment to the skin area of the skin surface via the waveform applied to the electrodes, wherein the waveform comprises one or more pulses with a same or opposite polarity; and a treatment phase following the pretreatment phase, comprising:

applying a treatment substance to the skin area of the skin surface, wherein permeability of the skin surface to the treatment substance is enhanced or increased responsive to the microcurrent pretreatment in the skin area between the electrodes, absent further application of the electrical waveform during the treatment phase;

wherein the waveform has a charge-balanced microcurrent functional form, and further comprising:

regulating or modulating a power output of the waveform in the pretreatment phase, wherein the power output is selected to enhance or increase the permeability of the skin surface in the skin area between the electrodes to the treatment substance in the treatment phase, and to enhance or increase user comfort during the pretreatment phase, as compared to application of the microcurrent pretreatment absent regulating or modulating the power output in the pretreatment phase.

16. The method of claim 15, further comprising a latency phase defined between the pretreatment phase and the treatment phase, wherein:

the latency phase extends for a period of at least five minutes; and the treatment phase extends for a period of at least five minutes, during which the permeability of the skin surface to the treatment substance is increased or enhanced in the skin area between the electrodes, as compared to permeability of such a skin surface absent the pretreatment phase.

17. The method of claim 15, further comprising applying a conducting gel or fluid to the skin surface prior to or during the pretreatment phase, wherein the conducting gel or fluid is selected to form a conducting path between the electrodes and the skin area of skin surface between the electrodes, and for modulating a current density of the microcurrent pretreatment along the skin area of the skin surface between the electrodes.

18. A method for treating the skin surface on a subject according to claim 15, further comprising:

pretreating the skin surface of the subject by applying a voltage or current signal comprising the waveform via one or more of the electrodes, wherein power is output to the skin surface, modulating the voltage or current signal, wherein the power output is selected to enhance or increase the permeability of the skin surface; and treating the skin surface by applying an agent comprising the selected treatment substance thereto, wherein permeability of the skin surface to one or more components of the agent is enhanced or increased, responsive to the modulated power output while pretreating the skin surface, absent further voltage or current signal applied to the skin surface via the one or more electrodes;

and further comprising generating the voltage or current signal as a DC, pulsed DC, microcurrent, or pulsed microcurrent waveform, wherein:

a polarity of the power output to the skin is alternated at periodic or aperiodic intervals.

19. The method of claim 18, wherein:

modulating the voltage or current signal comprises adjusting an amplitude of the signal such that the power output is selected for user comfort or efficacy of the enhancement or increase in permeability, or both, as compared to said power output absent modulating the voltage or current signal; or the modulated power output is selected for the enhanced or increased permeability to include enhanced or increased absorption, adsorption, diffusion or transmissibility of the one or more components of the agent into or through one or more of layers of the skin surface during the treatment period, as compared to said absorption, adsorption, diffusion or transmissibility absent applying the voltage or current signal to the skin surface.

20. The method of claim 18, wherein:

the one or more layers of the skin surface comprise a stratum corneum, outer epidermis, lower epidermis, or dermis, or wherein the one or more layers of the skin surface comprise vasculature or fibroblasts, and the treatment period extends at least one to two hours after application of the voltage or current signal, or at least twenty-four hours after application of the voltage or current signal;

and further comprising defining a latency period following pretreating the skin surface, wherein no further voltage or current signal is applied to the skin surface via the one or more electrodes during the latency period, wherein:

the agent is applied to the skin surface following the latency period, wherein the latency period extends for at least one to two minutes following application of the voltage or current signal, or for at least one to two hours following application of the voltage or current signal.

21. The method of claim 18, further comprising generating the waveform for applying the voltage or current signal to the skin surface, wherein the waveform comprises alternating sequences of positive and negative polarity, and:

wherein the alternating sequences of positive and negative polarity are symmetric or aperiodic, or have randomized or pseudorandom pulse width, pulse height or period; and wherein positive and negative components of the waveform are charge balanced over a period of 0.1-0.2 s, 0.2-1.0 s, or 1.0-1.5 s.

22. The method of claim 18, wherein the voltage or current signal applied to the skin surface comprises:

voltage or current pulses having amplitudes of 100 μA or less, or between 100 and 250 μA; or voltage or current pulses having individual pulse widths between 1 and 10 ms or less, or between 10 and 100 ms.

23. The method of claim 18, wherein applying the voltage or current signal and modulating the power output to the skin surface are performed for a pretreatment period selected to achieve the enhanced or increased permeability of the skin surface upon application of the agent, wherein:

the pretreatment period is selected for enhanced or increased absorption, adsorption, diffusion or transmissibility of the one or more components of the agent into or through one or more of layers of the skin surface during the treatment period, as compared to said absorption, adsorption, diffusion or transmissibility absent applying the voltage or current signal to the skin surface; and the pretreatment period is between about one and two minutes or less, or between two and ten minutes.

24. The method of claim 23, further comprising applying a topical to the skin surface, wherein the topical is applied before applying the voltage or current signal or while applying the voltage or current signal, wherein the topical comprises a conducting gel, a serum, a moisturizer, or a base component of a skin treatment product, and wherein the topical forms an electrically conducting path for the voltage or current signal between one or more of the electrodes and the skin surface.

25. A skin treatment system comprising:

a voltage or current source adapted to generate a voltage or current signal;

one or more electrodes adapted for applying the voltage or current signal to a skin surface of a subject, wherein power is output to the skin surface during a pretreatment phase; and control circuitry adapted to modulate the power output to the skin surface during the pretreatment phase, wherein the power output is selected to enhance or increase permeability of the skin surface to one or more components of an agent applied to the skin surface during a treatment phase, following the pretreatment phase;

wherein the enhanced or increased permeability of the skin surface is responsive to the modulated power output in the pretreatment phase, absent further voltage or current signal applied to the skin surface via the one or more electrodes in the treatment phase; and a voltage or current sensor configured for sensing the voltage or current signal proximate one or more of the electrodes; and a feedback circuit configured for generating a feedback signal responsive to change in the sensed voltage or current signal, based at least in part on impedance of or through the skin surface;

wherein the control circuitry is configured to define a response curve for the power output to the skin surface; and to:

lower the response curve to or toward a predetermined minimum level, based on a change in the feedback signal, or raise the response curve to or toward a predetermined maximum level, based on an absence of said change in the feedback signal.

26. The skin treatment system of claim 25, wherein the voltage or current signal comprises a microcurrent signal selected for a cosmetic treatment of the skin surface and the one or more electrodes comprise one or more pairs of electrodes having an elongated or lobed structure, wherein the voltage or current signal is applied with opposite polarity to said electrodes in each pair.

27. The skin treatment system of claim 25, wherein:

wherein the minimum and maximum power levels are selected to maintain user comfort, as compared to application of the voltage or current signal absent modulating the power output during the pretreatment phase; and wherein the waveform has a charge-balanced microcurrent functional form, as defined over a period for modulating the power output of at least 100 microseconds, at least 100 milliseconds, or at least one second.

28. The skin treatment system of claim 25, wherein:

the agent comprises ions, ionic or polar molecules, nonionic or nonpolar molecules, proteins, amino acids, genetic material, genetic markers, allantoin, or caffeine, and the microcurrent pretreatment is applied for a period of at least ten seconds, at least one minute, or at least two minutes; and further comprising a latency phase defined between the pretreatment phase and the treatment phase, wherein the latency phase extends for a period of at least five minutes, at least one hour, or at least twelve hours, wherein the treatment phase extends for a period of at least five minutes, at least one hour, or at least twelve hours, during which the permeability of the skin surface to the treatment substance is increased or enhanced, as compared to permeability of such a skin surface absent the pretreatment phase.

29. The skin treatment system of claim 25, wherein the agent comprises a conducting gel or fluid applied the skin surface prior to or during the pretreatment phase, and:

wherein the conducting gel or fluid is selected to form a conducting path between one or more of the electrodes and the skin surface; or wherein the conducting gel or fluid is selected for modulating a current density of the voltage or current signal applied to an area of the skin surface between the electrodes.

30. The skin treatment system of claim 25, further comprising a three-terminal device having a first terminal operatively coupled to the voltage sensor, a second terminal operatively coupled to the feedback circuit, and a gate operatively coupled to the control circuitry to define the response curve based at least in part on the sensed voltage or current and the feedback signal.

31. The method of claim 6, wherein modulating the power output comprises controlling a pulse width, period or amplitude of the waveform based on an impedance between two of the electrodes, as determined at least in part from the feedback signal.

32. The method of claim 1, wherein modulating the power output is performed with a three-terminal device having a first terminal operatively coupled to a sensor configured for sensing the voltage or current waveform proximate the one or more electrodes, a second terminal operatively coupled to the feedback signal, and a gate adapted to define the response curve.

33. The method of claim 13, wherein the selected treatment substance comprises one or more ions, ionic or polar molecules, proteins or amino acids, or genetic material, genetic markers, allantoin, or caffeine.

34. The method of claim 13, wherein modulating the power output comprises controlling a pulse width, period or amplitude of the voltage or current waveform based on an impedance between two of the electrodes, as determined at least in part from the feedback signal.

\* \* \* \* \*